(12) United States Patent
Bavik et al.

(10) Patent No.: US 9,957,224 B2
(45) Date of Patent: May 1, 2018

(54) METHODS FOR THE TREATMENT OF DIABETIC RETINOPATHY AND OTHER OPHTHALMIC DISEASES

(71) Applicant: Acucela Inc., Seattle, WA (US)

(72) Inventors: Claes Olof Bavik, Lake Forest Park, WA (US); Susan Hayes Henry, Kirkland, WA (US); Ryo Kubota, Seattle, WA (US); Vladimir A. Kuksa, Bothell, WA (US)

(73) Assignee: ACUCELA INC, Seattle, WA (US)

( * ) Notice: Subject to any disclaimer, the term of this patent is extended or adjusted under 35 U.S.C. 154(b) by 0 days. days.

(21) Appl. No.: 13/887,243

(22) Filed: May 3, 2013

(65) Prior Publication Data

US 2014/0039048 A1 Feb. 6, 2014

Related U.S. Application Data

(60) Provisional application No. 61/643,051, filed on May 4, 2012, provisional application No. 61/643,058, filed on May 4, 2012, provisional application No. 61/643,178, filed on May 4, 2012, provisional application No. 61/781,907, filed on Mar. 14, 2013.

(51) Int. Cl.
| | |
|---|---|
| *A61K 31/137* | (2006.01) |
| *A61K 31/138* | (2006.01) |
| *A61K 31/35* | (2006.01) |
| *A61K 31/765* | (2006.01) |
| *A61K 45/06* | (2006.01) |
| *C07C 215/08* | (2006.01) |
| *C07C 211/27* | (2006.01) |
| *C07C 217/20* | (2006.01) |
| *C07C 323/32* | (2006.01) |
| *C07D 309/06* | (2006.01) |

(52) U.S. Cl.
CPC .......... *C07C 215/08* (2013.01); *A61K 31/137* (2013.01); *A61K 31/138* (2013.01); *A61K 31/35* (2013.01); *A61K 31/765* (2013.01); *A61K 45/06* (2013.01); *C07C 211/27* (2013.01); *C07C 217/20* (2013.01); *C07C 323/32* (2013.01); *C07D 309/06* (2013.01)

(58) Field of Classification Search
CPC .... A61K 31/137; A61K 31/138; A61K 31/35; A61K 31/765; A61K 45/06; C07C 211/27; C07C 215/08; C07C 217/20; C07C 323/32; C07D 309/06
See application file for complete search history.

(56) References Cited

U.S. PATENT DOCUMENTS

| | | | |
|---|---|---|---|
| 5,391,377 A | 2/1995 | Barnwell | |
| 2003/0181531 A1* | 9/2003 | Sherris et al. | 514/720 |
| 2007/0249713 A1* | 10/2007 | Larsen | A61K 31/05 514/559 |
| 2008/0131484 A1* | 6/2008 | Robinson et al. | 424/428 |
| 2009/0170841 A1 | 7/2009 | Scott et al. | |
| 2010/0113539 A1 | 5/2010 | Scott et al. | |
| 2011/0003895 A1 | 1/2011 | Kubota et al. | |

FOREIGN PATENT DOCUMENTS

| | | |
|---|---|---|
| WO | WO2008/131368 | 10/2008 |
| WO | WO2009/005794 | 1/2009 |
| WO | WO2009/045479 | 4/2009 |
| WO | WO2009/058216 | 5/2009 |
| WO | WO2010/028088 | 3/2010 |
| WO | WO2010/048332 | 4/2010 |

OTHER PUBLICATIONS

Akimba. A Novel Murine Model for Diabetic Retinopathy (www.Bio-link.com) (2010).
Akula et al. The oscillatory potentials of the dark-adapted electroretinogram in retinopathy of prematurity. Invest. Ophthalmol. Vis. Sci., (2007) 48:5788-97.
Akula et al. Rod photoreceptor function predicts blood vessel abnormality in retinopathy of prematurity. Invest Ophthalmol Vis Sci. 2007; 48(9):4351-9.
Anonymous Argon laser photocoagulation for neovascular maculopathy. Three-year results from randomized clinical trials. Macular Photocoagulation Study Group. Ophthalmol. 104(5):694-701 (1986).
Arden et al. Spare the rode and spol the eye. Br. J. Opthalmol., 2005; 89(6):764-769.
Barnaby et al. Development of scotopic visual thresholds in retinopathy of prematurity. Invest. Ophthalmol. Vis. Sci., (2007). 48:4854-60.
Berge. Pharmaceutical Salts. Journal of Pharmaceutical Sciences. 1997; 66:1-19.
Bundgard. Design of Prodrugs. Elsevier, Amsterdam. 1985; pp. 7-9, 21-24.
Chan et al. Differential expression of pro- and antiangiogenic factors in mouse strain-dependent hypoxia-induced retinal neovascularization. Lab. Invest. 2005; 85(6):721733.
Connor et al. Quantification of oxygen-induced retinopathy in the mouse: a model of vessel loss, vessel regrowth and pathological angiogenesis. Nat. Protoc. 2009; 4(100):1565-1573.
Dembinska et al. Graded contribution of retinal maturation to the development of oxygen-induced retinopathy in rats. Invest. Ophthalmol. Vis. Sci. (2001); 42:1111-1118.

(Continued)

Primary Examiner — Sahar Javanmard
(74) Attorney, Agent, or Firm — Wilson, Sonsini, Goodrich & Rosati

(57) ABSTRACT

Methods are provided herein for the treatment of ophthalmic diseases or conditions such as an ophthalmic disease or disorder associated with diabetes in a patient. Also provided herein are methods of treating retinopathy of prematurity in a patient. Further, provided herein are methods for treating wet age-related macular degeneration in a patient. The methods comprise administration of compounds disclosed herein to a patient in need thereof that inhibit or slow one or more signs or symptoms of such conditions.

5 Claims, 27 Drawing Sheets

(56) References Cited

OTHER PUBLICATIONS

Dembinska et al. Evidence for a brief period of enhanced oxygen susceptibility in the rat model of oxygen-induced retinopathy. Invest Ophthalmol Vis Sci. 2002; 43(7):2481-90.
Deng et al. Diabetic Retinopathy in Experimental Animal Models—An Update. International Journal of Diabetes, vol. 6 (issue 1), 1998 (18 pgs).
Engerman et al. Retinopathy in galactosemic dogs continues to progress after cessation of galactosemia. Arch Ophthalmol. 1995; 113(3):355-358.
Feit-Leichman et al. 2005. Vascular damage in a mouse model of diabetic retinopathy: relation to neuronal and glial changes. Investigative Ophthalmology & Visual Science 46(11):4281-4287.
Fix. 1996. Oral controlled release technology for peptides: status and future prospects. Pharm Res. 13:1760-1764.
Fulton et al. The rod photoreceptors in retinopathy of prematurity: an electroretinographic study. Arch. Ophthalmol., (2001); 119:499-505.
Fulton et al. Rod photoreceptors in infant rats with a history of oxygen exposure. Invest. Ophthalmol. Vis. Sci. (1999) 40:168-174.
Fulton et al. Retinal degenerative and hypoxic ischemic disease. Doc Ophthalmol.(2009) 118(1):55-61.
Fulton et al. The rhodopsin content of human eyes. Invest. Ophthalmol. Vis. Sci. (1999) 40:1878-1883.
Fulton et al. The cone electroretinogram in retinopathy of prematurity. Invest. Ophthalmol. Vis. Sci. 49(2):814-9 (2008).
Gariano et al. Expression of angiogenesis-related genes during retinal development. Gene Expression Patterns. (2006) 6:187-192.
Gelman et al. Diagnosis of plus disease in retinopathy of prematurity using Retinal Image multiScale Analysis. Invest. Ophthalmol. Vis. Sci. (2005) 46(12):4734-4738.
Hagins et al. Transduction heats in retinal rods: tests of the role of cGMP by pyroelectric calorimetry. Proc Natl Acad Sci USA (1989) 86:1224-1228.
Hansen et al. Retinal degeneration in children: dark adapted visual threshold and arteriolar diameter. Vision Research. 48(3):325-31 (2008).
Henson et al. Feline models of type 2 diabetes mellitus. ILAR Journal. 47(3):234-242.
Hood et al. Rod phototransduction in retinitis pigmentosa: estimation and interpretation of parameters derived from the rod a-wave. Invest. Ophthalmol. Vis. Sci. (1994) 35:2948-2961.
Kador et al. Prevention of retinal vessel changes associated with diabetic retinopathy in galactose-fed dogs by aldose reductase inhibitors. Arch Ophthalmol. 1990; 108(9):1301-1309.
Kato et al. 2003. Long-term treatment with fidarestat suppresses the development of diabetic retinopathy in STZ-induced diabetic rats. Journal of Diabetes and Its Complications. 17(6):374-379.
Kern et al. A mouse model of diabetic retinopathy. Arch Ophthalmol. 1996; 114(8):986-990.
Kim et al. Retinopathy in monkeys with spontaneous type 2 diabetes. Invest Ophthalmol Vis Sci. 2004; 45:4543-4553.
Kubota et at. Safety and effect on rod function of ACU-4429, a novel small-molecule visual cycle modulator. Retina, 2012; 32(1):183-188.
Lamb et al. A quantitative account of the activation steps involved in phototransduction in amphibian photoreceptors. J. Physiol. (Lond). (1992) 449:719-758.
Liu et al. The retinal vasculature and function of the neural retina in a rat model of retinopathy of prematurity. Invest. Ophthalmol. Vis. Sci. (2006) 47:2639-47.
Liu et al. Development of the Electroretinographic Oscillatory Potentials in Normal and Rop Rats. Invest. Ophthalmol. Vis. Sci., (2006) 47:5447-52.
Lu et al. Retinal changes in Otsuka long-evans Tokushima Fatty rats (spontaneously diabetic rat)—possibility of a new experimental model for diabetic retinopathy. Journal of Ophthalmology. 47(1):28-35, 2003.
Lutty et al. Proceedings of the Third International Symposium on Retinopathy of Prematurity: an update on ROP from the lab to the nursery (Nov. 2003, Anaheim, California). Mol Vis (2006) 12:532-580.
Mansour et al. Reduction of Basement Membrane Thickening in Diabetc Cat Retina by Sulindac. Investigative Ophthalmology & Visual Science. 31(3):457-463. Mar. 1990.
Marinez-Perez et al. Retinal vascular tree morphology: a semi-automatic quantification. Trans. Biomed. Eng. (2002) 49:912-917.
Moiseyev et al. RPE65 is the isomerohydrolase in the retinoid visual cycle. Proc Natl Acad Sci USA (2005) 102:12413-12418.
Moskowitz et al. Early ametropia and rod photoreceptor function in retinopathy of prematurity. Optometry & Vision Science. (2005) 82:307-317.
Palmer et al. Incidence and early course of retinopathy of prematurity. The Cryotherapy for Retinopathy of Prematurity Cooperative Group. Ophthalmology. (1991) 98:1628-1640.
PCT/US2013/039562 International Search Report and Written Opinion dated Dec. 5, 2013.
Penn et al. The range of PaO2 variation determines the severity of oxygen-induced retinopathy in newborn rats. Invest. Ophthalmol. Vis. Sci. 1995. 36:2063-2070.
Pugh et al. Amplification and kinetics of the activation steps in phototransduction. Biochim. Biophys. Acta. 1993. 1141:111-149.
Pugh et al. Handbook of biological physics. vol. 3 (2000), Elsevier Science. p. 183-255.
Rando. The Biochemistry of the Visual Cycle. Chem Rev (2001) 101:1881-1896.
Reynaud et al. Extraretinal neovascularization induced by hypoxic episodes in the neonatal rat. Invest Ophthalmol Vis Sci (1994) 35:3169-3177.
Reynaud et al. Effect of prior oxygen exposure on the electroretinographic responses of infant rats. Invest. Ophthalmol. Vis. Sci. (1995) 36:2071-2079.
Ricci et al. Early assessment of visual function in full term newborns. Early Hum Dev. Feb. 2008; 84(2):107-13.
Ricci et al. Cortical visual function in preterm infants in the first year. J Pediatr. Apr. 2010; 156(4):550-5.
Roche. Bioreversible Carriers in Drug Design, American Pharmaceutical Association and Pergamon Press, 1987.
Samanen et al. 1996. Chemical approaches to improve the oral bioavailability of peptidergic molecules. J. Pharm. Pharmacol. 48:119-135.
Seeliger et al. In vivo confocal imaging of the retina in animal models using scanning laser ophthalmoscopy. Vision Res. (2005) 45:3512-9.
Sima et al. The BB Wistar rat: an experimental model for the study of diabetic retinopathy. Metabolism, 32(7, Suppl. 1):136-140, Jul. 1983.
Sima et al. The BB-rat—an authentic model of human diabetic retinopathy. Current Eye Research. 1985. 4(10):1087-1092.
Singh et al. Encyclopedia of Pharmaceutical Technology, 2nd Ed., pp. 754-757 (2002).
Sparrow et al. A2E, a byproduct of the visual cycle. Vision Res. 2003. 43(28):29832990.
Steinberg. Monitoring Communications Between Photoreceptors and Pigment Epithelial Cells: Effects of "Mild" Systemic Hypoxia. Invest. Ophthalmol. Vis. Sci. (1987) 28:1888-1903.
Travis et al. Diseases Caused by Defects in the Visual Cycle: Retinoids as Potential Therapeutic Agents. Ann. Rev. Pharmacol. Toxicol. 2007; 47:469-512.
Wellard et al. Photoreceptors in the rat retina are specifically vulnerable to both hypoxia and hyperoxia. Vis Neurosci (2005) 22:501-507.
Yoshida et al. Digoxin inhibits retinal ischemia-induced HIF-1alpha expression and ocular neovascularization. FASEB J. 2010; 24(6):1759-1767.
Young. The renewal of photoreceptor cell outer segments. J Cell Biol (1967) 33:61-72.
Henry et al. Visual Cycle Modulators (VCMs) as Inhibitors of Retinal Neovascularization. ARVO Annual Meeting Abstract (6 pgs) (2012).

(56) References Cited

OTHER PUBLICATIONS

Acucela, Inc. Experimental Eye Research Journal 2010 (7 pgs) (w/translation).
UMEDA. Medical development. 156(13):1017-1020 (1991) (w/translation).

* cited by examiner

METHODS FOR THE TREATMENT OF DIABETIC RETINOPATHY AND OTHER OPHTHALMIC DISEASES

CROSS REFERENCE

This application claims the benefit of U.S. Provisional Application No. 61/781,907, filed Mar. 14, 2013, U.S. Provisional Application No. 61/643,178, filed May 4, 2012, U.S. Provisional Application No. 61/643,051, filed May 4, 2012, U.S. Provisional Application No. 61/643,058, filed May 4, 2012, which are incorporated herein by reference in their entirety.

BACKGROUND OF THE INVENTION

Diabetic Retinopathy is a common and specific micro vascular complication of diabetes, and is the leading cause of preventable blindness in working-age people. It is identified in a third of people with diabetes and is associated with increased risk of life-threatening systemic vascular complications, including stroke, coronary heart disease, and heart failure. Optimum control of blood glucose, blood pressure, and possibly blood lipids remains the foundation for reduction of risk of retinopathy development and progression.

Retinopathy of prematurity (ROP) blinds between about 400-800 babies annually in the United States, and reduces vision in many thousands more world-wide. It is a growing problem in the developing world because while steady improvements in neonatal intensive care have led to an increase in the survival rate of very low birth weight infants, these are the very patients at greatest risk for ROP.

The retina contains photoreceptors that transduce light into a neural signal, and also has an extensive vascular supply. The clinical hallmark of ROP is abnormal retinal vasculature, which appears at the pre-term ages. This abnormal vasculature is insufficient to supply oxygen during the maturation of the rod photoreceptors, cells that are the most demanding of oxygen of any cells in the body. In the most severe ROP cases, vision loss results from retinal detachment instigated by leaky retinal blood vessels. However, milder cases of ROP, the retinal vascular abnormalities usually resolve without treatment, but the patients nevertheless suffer a range of lifelong visual impairments even with optimal optical correction.

Age-related macular degeneration (AMD) is the major cause of severe visual loss in the United States for individuals over the age of 55. AMD occurs in either an atrophic or (less commonly) an exudative form. In exudative AMD, blood vessels grow from the choriocapillaris through defects in Bruch's membrane, and in some cases the underlying retinal pigment epithelium (choroidal neovascularization or angiogenesis). Organization of serous or hemorrhagic exudates escaping from these vessels results in fibrovascular scarring of the macular region with attendant degeneration of the neuroretina, detachment and tears of the retinal pigment epithelium, vitreous hemorrhage and permanent loss of central vision. This process is responsible for more than 80% of cases of significant visual loss in patients with AMD.

Choroidal neovascularization (CNV) has proven recalcitrant to treatment in most cases. Laser treatment can ablate CNV and help to preserve vision in selected cases not involving the center of the retina, but this is limited to only about 10% of the cases. Unfortunately, even with successful laser photocoagulation, the neovascularization recurs in about 50-70% of eyes (50% over 3 years and >60% at 5 years). (Macular Photocoagulation Study Group, Arch. Ophthalmol. 204:694-701 (1986)). In addition, many patients who develop CNV are not good candidates for laser therapy because the CNV is too large for laser treatment, or the location cannot be determined so that the physician cannot accurately aim the laser.

Retinal neovascularization (RNV) develops in numerous retinopathies associated with retinal ischemia, such as sickle cell retinopathy, Eales disease, ocular ischemic syndrome, carotid cavernous fistula, familial exudative vitreoretinopathy, hyperviscosity syndrome, idiopathic occlusive arteriolitis, radiation retinopathy, retinal vein occlusion, retinal artery occlusion, retinal embolism. Retinal neovascularization can also occur with inflammatory diseases (birdshot retinochoroidopathy, retinal vasculitis, sarcoidosis, toxoplasmosis, and uveitis), choroidal melanoma, chronic retinal detachment, incontinentia pigmenti, and rarely in retinitis pigmentosa.

A factor common to almost all RNV is retinal ischemia, which releases diffusible angiogenic factors (such as VEGF). The neovascularization begins within the retina and then breaches the retinal internal limiting membrane. The new vessels grow on the inner retina and the posterior surface of the vitreous after it has detached (vitreous detachment). Neovascularization may erupt from the surface of the optic disk or the retina. RNV commonly progresses to vitreoretinal neovascularization. Iris neovascularization often follow retinal neovascularization.

SUMMARY OF THE INVENTION

Provided herein are methods for treating various ophthalmic diseases or conditions such as an ophthalmic disease or disorder associated with diabetes in a patient. Also provided herein is a method of treating retinopathy of prematurity in a patient. Further, provided herein is a method for treating wet age-related macular degeneration in a patient.

In one aspect, herein is a method of treating retinopathy of prematurity in an immature eye by administering a Visual Cycle Modulation (VCM) compound to a patient in need thereof. The methods described herein relate to the administration of compounds described herein that are visual cycle modulators (VCM) that reduce or suppress energy-demanding processes in rod photoreceptors. In one embodiment, the VCM compound is administered orally.

In another aspect, described herein is a method of improving rod-mediated retinal function by administering a VCM compound to a patient with an immature retina. The methods described herein reduce rod energy demand in the developing retina, whereby rod-mediated retinal function is improved upon retinal maturity relative to a patient not treated with the agent.

In another aspect, described herein is a method of modulating the visual cycle by administering to a patient in need thereof a composition comprising a compound described herein, where modulation of the visual cycle treats retinopathy of prematurity.

Also described herein is a method for improving function and/or suppressing the visual cycle in a developing rod cell, by contacting the cell with a VCM compound that suppresses energy demand in the rod cell. In one embodiment of such methods, the treatment is administered locally to the eye. In another embodiment such methods, the treatment is administered at a site distant from the eye or systemically.

In one embodiment, a patient to be treated with a compound described herein is administered one or more additional compounds or treatments. For example, in one embodiment, the patient is treated with supplemental oxygen.

In a further aspect is a method for treating wet age-related macular degeneration in a patient comprising administering to the patient a therapeutically effective amount of a Visual Cycle Modulation (VCM) compound.

Patients to be treated include humans as well as non-humans (e.g., domestic or wild animals)

In one embodiment, the composition of the VCM compound is administered orally. Compositions may be administered one or more times. Administration may occur more than once per day, once per day, every other day, every week, or every month.

In such methods, treatment results in improvement of one or more symptoms of the patient. Symptoms that may be improved by such methods include, but are not limited to, bleeding, leaking, scarring, damage to the photoreceptors, vision loss, or a combination thereof.

In one embodiment is a method for reducing or inhibiting vascularization (e.g., neovascularization) in a patient comprising administering to the patient a therapeutically effective amount of a Visual Cycle Modulation (VCM) compound. In one embodiment, the vascularization is associated with choroidal neovascularization. In one embodiment, the vascularization is associated with retinal neovascularization. The inhibition or reduction in vascularization can be, for example, at least about 1%, 2%, 5%, 10%, 15%, 20%, 25%, 30%, 35%, 40%, 45%, 50%, 55%, 60%, 65%, 70%, 75%, 80%, 85%, 90%, 95%, or 100%.

In one embodiment is a method for treating choroidal neovascularization in a patient comprising administering to the patient a therapeutically effective amount of a Visual Cycle Modulation (VCM) compound.

One embodiment described herein is a method for protecting an eye during medical procedures requiring exposure of the eye to bright light, to laser light, procedures resulting in prolonged and/or excessive dilation of the pupil, or that otherwise sensitize the eye to light, the method comprising administration of a composition comprising a compound described herein to a patient in need thereof. The compounds described herein, at sufficient dosages, inhibit the visual cycle by at least 50%. Thus, in some embodiments, an effective dose inhibits the visual cycle in the eye of the subject undergoing the medical procedure by at least 50%, by at least 75%, or by at least 90%. Furthermore, the duration of the inhibition also depends on the dose. Thus, in one embodiment, the inhibition continues for at least one hour, for at least 2 hours, for at least 4 hours, for at least 8 hours, for at least 12 hours, for at least 24 hours, or for at least 48 hours. Finally, the compounds herein are reversible inhibitors of the visual cycle, and thus the subjects visual cycle returns to normal within 3 half-lives. In one embodiment, the compound used with such aforementioned medical procedures is emixustat.

In another aspect are dosing schedules (e.g., number of administrations per day) for the treatment of the ophthalmic diseases and conditions described herein. In one embodiment, the compound is administered once daily (which includes multiple sub-doses of the compound administered at approximately the same time); in another embodiment, the compound is administered once every two days (which includes multiple sub-doses of the compound administered at approximately the same time); and in another embodiment, the compound is administered once every three days or more (which includes multiple sub-doses of the compound administered at approximately the same time).

In another aspect are dosing schedules (e.g., variations between dose amounts of subsequent administrations) for the treatment of the ophthalmic diseases and conditions described herein. In one embodiment, the compound is administered on day 1 at a dose level higher than that administered on following days (e.g., a loading dose). In another embodiment, the compound is administered on day 1 at a dose level two times that administered on following days. In another embodiment, the compound is administered on day 1 at a dose level three times that administered on following days.

In another aspect are dosing schedules (e.g., time of day when compound is administered) for the treatment of the ophthalmic diseases and conditions described herein. In one embodiment, the compound is administered in the morning; in another embodiment, the compound is administered in the evening; in another embodiment, the compound is administered upon waking; and in another embodiment, the compound is administered prior to going to sleep. In one embodiment, the compound is administered as a controlled release formulation in the evening. In another embodiment, the compound is administered prior to eating, or alternatively during a meal, or alternatively, subsequent to a meal. In some embodiments, such a meal is breakfast; in other embodiments, such a meal is lunch; in yet other embodiments, such a meal is dinner/supper.

In one aspect the daily dose of (R)-3-amino-1-(3-(cyclohexylmethoxy)phenyl)propan-1-ol is about 4 mg to about 100 mg. In another aspect the daily dose of (R)-3-amino-1-(3-(cyclohexylmethoxy)phenyl)propan-1-ol is about 2 mg; about 5 mg; about 7 mg; about 10 mg; about 15 mg; about 20 mg; about 40 mg; about 60 mg; about 75 mg; or about 100 mg.

Inhibition of the visual cycle is determined, in some embodiments, by an ERG. Information regarding doses of the compounds described herein, sufficient to inhibit the visual cycle to at least 50%, as well as methods for determining visual cycle inhibition in a subject (including ERG) are described in US Patent Application Publication US 2011/0003895, which incorporated herein by reference for such disclosure.

In one embodiment, the composition is administered orally prior to the medical procedure. In one embodiment, the composition is administered 24 hours and/or 48 hours after the medical procedure.

In one embodiment, the composition of the VCM compound is administered orally. Compositions may be administered one or more times. Administration may occur more than once per day, once per day, every other day, every week, or every month.

In such methods, treatment results in improvement of one or more symptoms of the patient. Symptoms that may be improved by such methods include, but are not limited to, defects in Bruch's membrane, increases in amount of ocular vascular endothelial growth factor (VEGF), myopia, myopic degeneration, deterioration of central vision, metamorphopsia, color disturbances, hemorrhaging of blood vessels, or a combination thereof.

In one embodiment is a method for treating retinal neovascularization in a patient comprising administering to the patient a therapeutically effective amount of a Visual Cycle Modulation (VCM) compound.

In one embodiment, the retinal neovascularization is associated with one or more retinopathies including, but not limited to, sickle cell retinopathy, Eales disease, ocular ischemic syndrome, carotid cavernous fistula, familial exudative vitreoretinopathy, hyperviscosity syndrome, idiopathic occlusive arteriolitis, radiation retinopathy, retinal vein occlusion, retinal artery occlusion, retinal embolism, birdshot retinochoroidopathy, retinal vasculitis, sarcoidosis, toxoplasmosis, uveitis, choroidal melanoma, chronic retinal detachment, incontinentia pigmenti, and retinitis pigmentosa.

In another aspect is a method for treating an ophthalmic disease or disorder associated with diabetes in a patient; treating or preventing retinopathy of prematurity in a patient; or treating an ophthalmic disease or disorder associated with neovascularization in the eye of a patient, comprising administering to the patient a therapeutically effective amount of a composition comprising a compound of Formula (A), or tautomer, stereoisomer, geometric isomer, N-oxide or a pharmaceutically acceptable salt thereof:

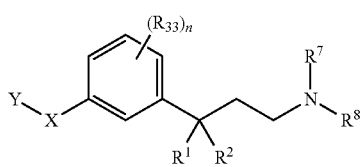

Formula (A)

wherein,
X is selected from —C($R^9$)=C($R^9$)—, —C≡C—, —C($R^9$)$_2$—O—, —C($R^9$)$_2$—C($R^9$)$_2$—, —C($R^9$)$_2$—S—, —C($R^9$)$_2$—S(O)$_2$—, or —C($R^9$)$_2$—NR$^9$—;
Y is selected from:
  a) substituted or unsubstituted carbocyclyl, optionally substituted with $C_1$-$C_4$ alkyl, halogen, —OH, or $C_1$-$C_4$ alkoxy;
  b) substituted or unsubstituted carbocyclylalkyl, optionally substituted with $C_1$-$C_4$ alkyl, halogen, —OH, or $C_1$-$C_4$ alkoxy;
  c) substituted or unsubstituted aralkyl, optionally substituted with $C_1$-$C_4$ alkyl, halogen, —OH, or $C_1$-$C_4$ alkoxy; or
  d) substituted or unsubstituted $C_3$-$C_{10}$ alkyl, optionally substituted with halogen, —OH, or $C_1$-$C_4$ alkoxy;
$R^1$ is hydrogen and $R^2$ is hydroxyl; or $R^1$ and $R^2$ form an oxo;
$R^7$ is hydrogen;
$R^8$ is hydrogen or $CH_3$;
each $R^9$ independently hydrogen, or substituted or unsubstituted $C_1$-$C_4$ alkyl;
each $R^{33}$ is independently selected from halogen or substituted or unsubstituted $C_1$-$C_4$ alkyl, and n is 0, 1, 2, 3, or 4.

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein n is 0, 1, or 2.

Another embodiment provides the method wherein X is —C($R^9$)=C($R^9$)—. Another embodiment provides the method wherein X is —C≡C—. Another embodiment provides the method wherein X is —C($R^9$)$_2$—O—. Another embodiment provides the method wherein X is —C($R^9$)$_2$—C($R^9$)$_2$—. Another embodiment provides the method wherein X is —C($R^9$)$_2$—S—. Another embodiment provides the method wherein X is —C($R^9$)$_2$—S(O)$_2$—. Another embodiment provides the method wherein X is —C($R^9$)$_2$—NR$^9$—.

Another embodiment provides the method wherein Y is substituted or unsubstituted carbocyclyl, or substituted or unsubstituted $C_3$-$C_{10}$ alkyl. Another embodiment provides the method wherein Y is substituted or unsubstituted carbocyclyl. Another embodiment provides the method wherein the substituted or unsubstituted carbocyclyl is a substituted or unsubstituted 4-, 5-, 6-, or 7-membered ring. Another embodiment provides the method wherein the substituted or unsubstituted carbocyclyl is a 6-membered ring. Another embodiment provides the method wherein the substituted or unsubstituted 6-membered ring is a substituted or unsubstituted cyclohexyl. Another embodiment provides the method wherein the substituted or unsubstituted 6-membered ring is a substituted or unsubstituted cyclohexyl and X is —C($R^9$)$_2$—O—.

Another embodiment provides the method wherein Y is substituted or unsubstituted $C_3$-$C_{10}$ alkyl. Another embodiment provides the method wherein the substituted or unsubstituted $C_3$-$C_{10}$ alkyl is a substituted or unsubstituted $C_3$-$C_6$ alkyl. Another embodiment provides the method wherein the substituted $C_3$-$C_6$ alkyl is substituted with an $C_1$-$C_2$ alkoxy group. Another embodiment provides the method wherein the substituted $C_3$-$C_6$ alkyl is —$CH_2CH_2CH_2OCH_3$.

Another embodiment provides the method wherein $R^1$ is hydrogen and $R^2$ is hydroxyl. Another embodiment provides the method wherein $R^1$ and $R^2$ form an oxo. Another embodiment provides the method wherein $R^8$ is hydrogen. Another embodiment provides the method wherein $R^8$ is methyl. Another embodiment provides the method wherein $R^1$ is hydrogen, $R^2$ is hydroxyl and X is —C($R^9$)$_2$—O—.

One embodiment provides a method for treating an ophthalmic disease or disorder associated with diabetes in a patient; treating or preventing retinopathy of prematurity in a patient; or treating an ophthalmic disease or disorder associated with neovascularization in the eye of a patient comprising administering to the patient a therapeutically effective amount of a composition comprising a compound, or tautomer, stereoisomer, geometric isomer, N-oxide or a pharmaceutically acceptable salt thereof, selected from:

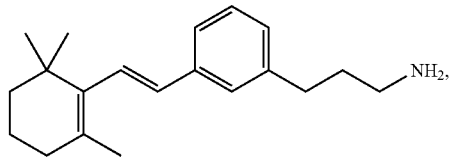

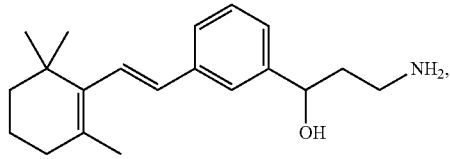

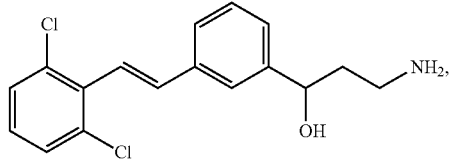

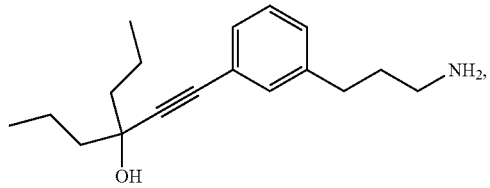

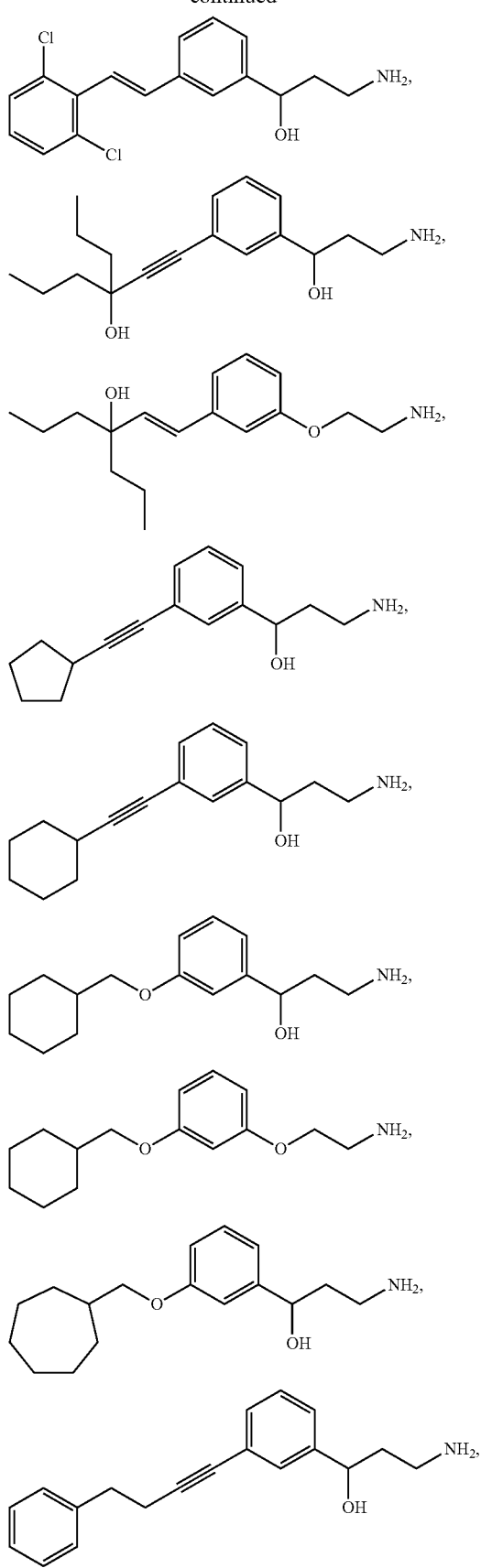
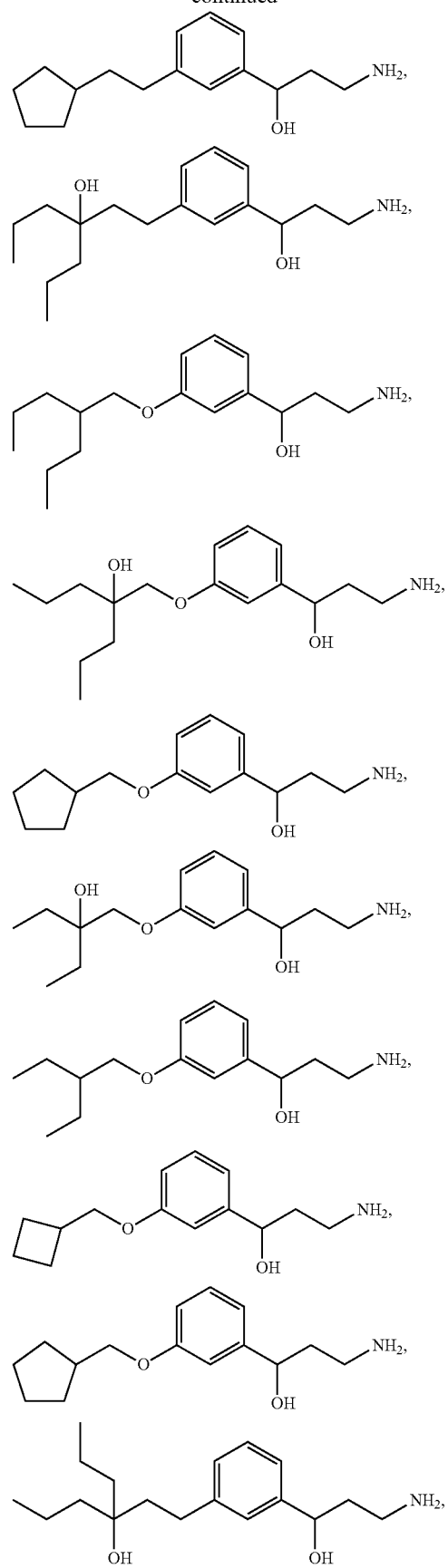

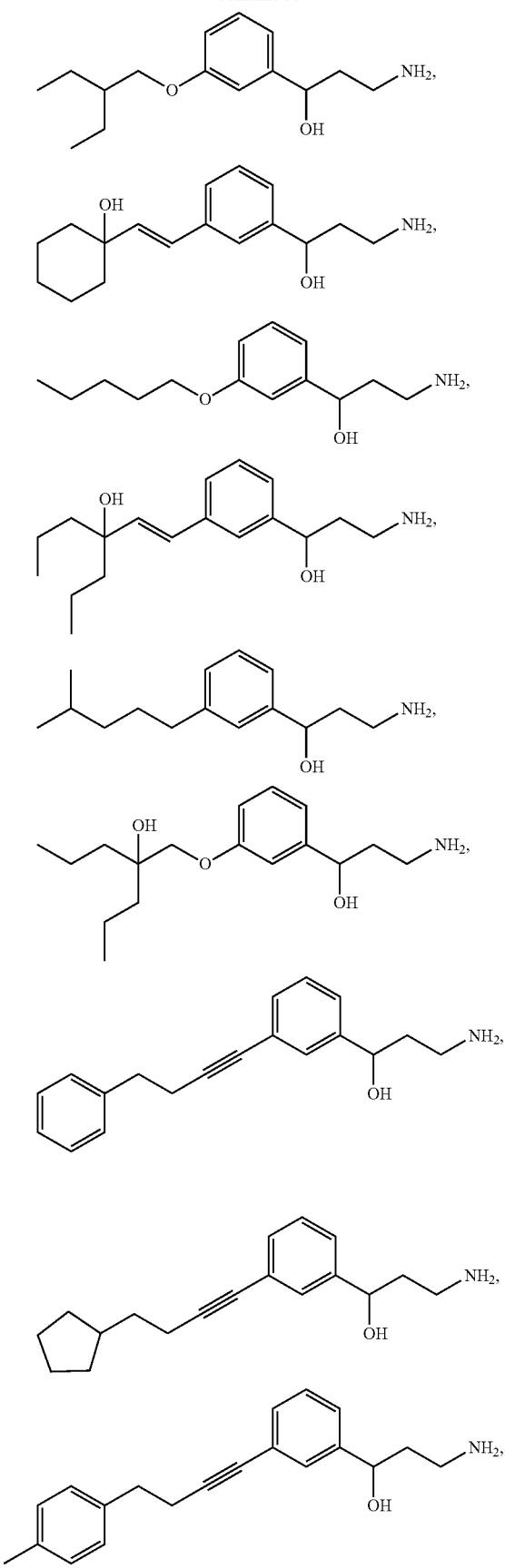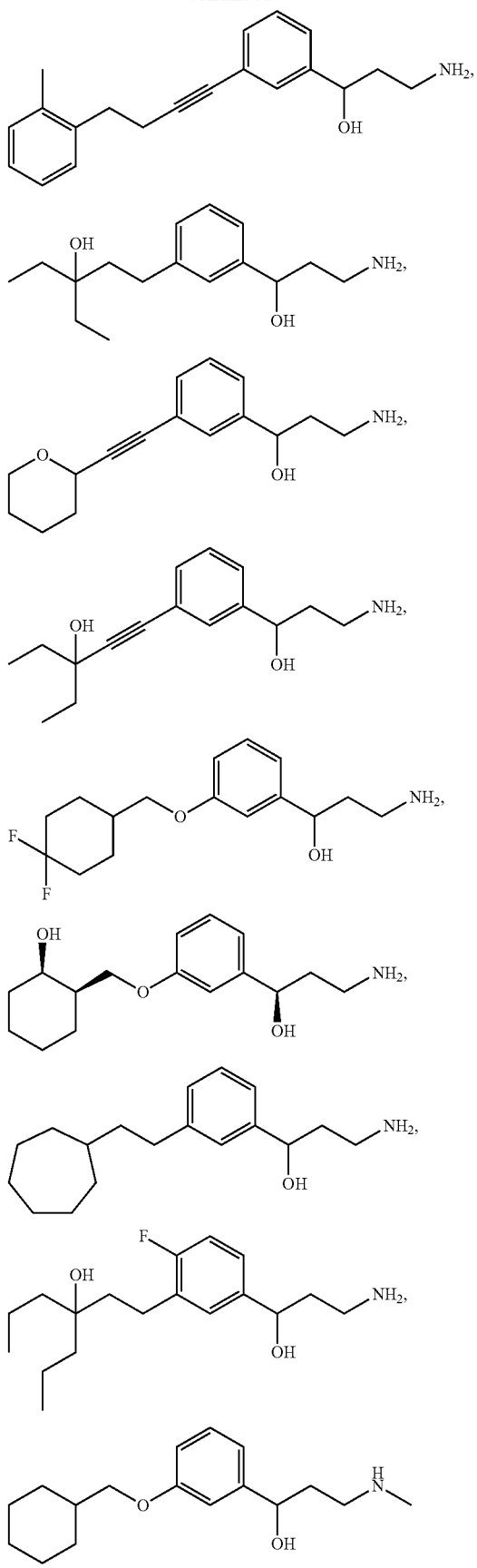

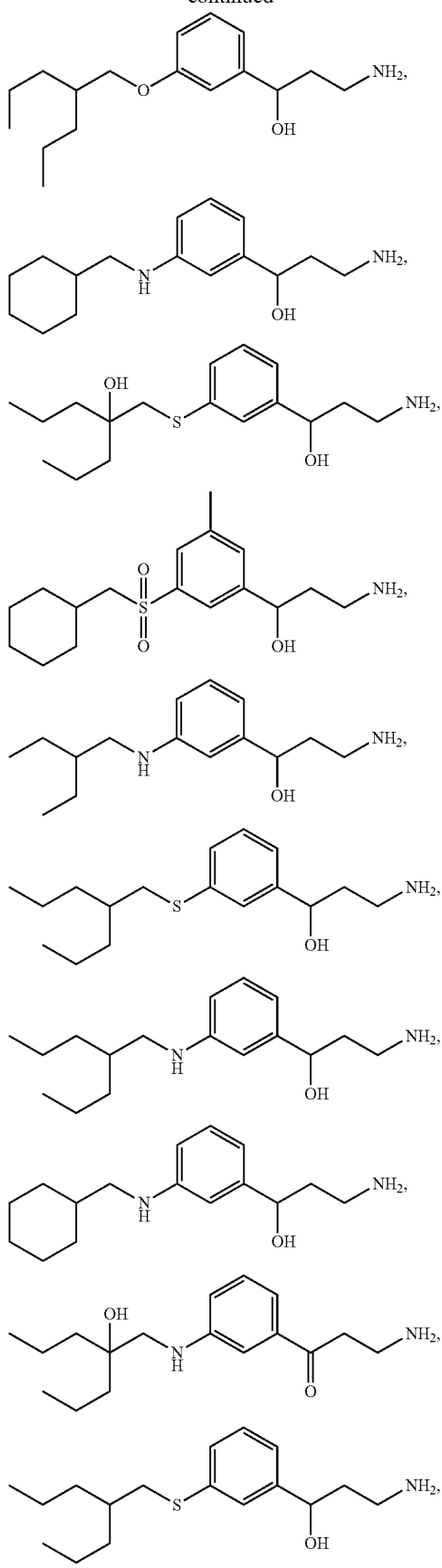

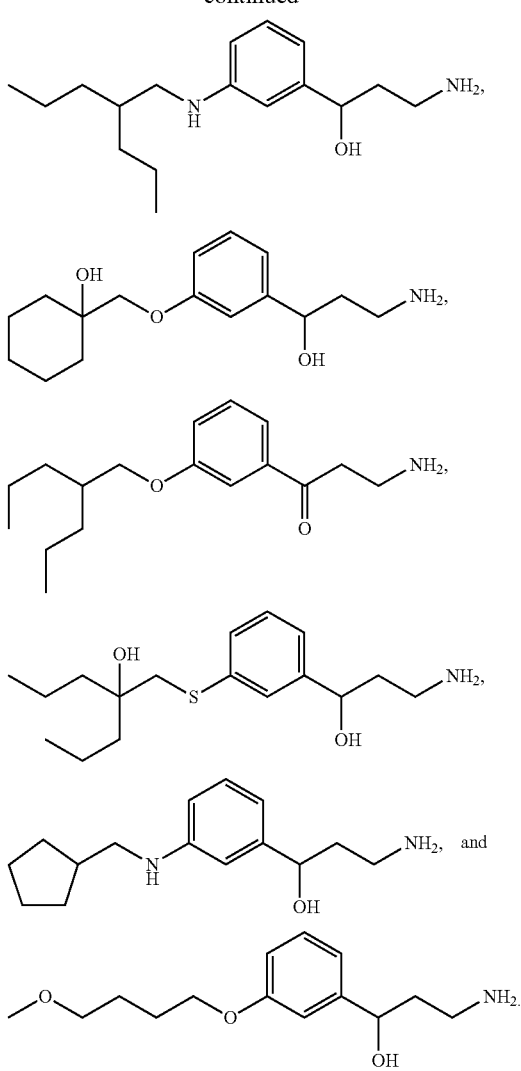

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient, wherein the composition comprises a compound, or stereoisomer, geometric isomer, N-oxide or a pharmaceutically acceptable salt thereof, selected from:

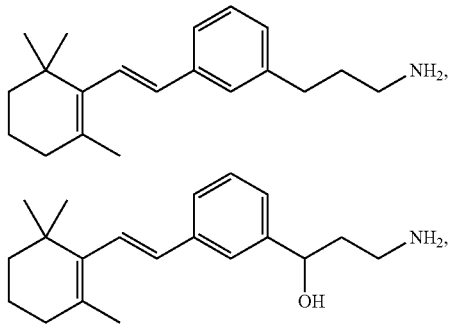

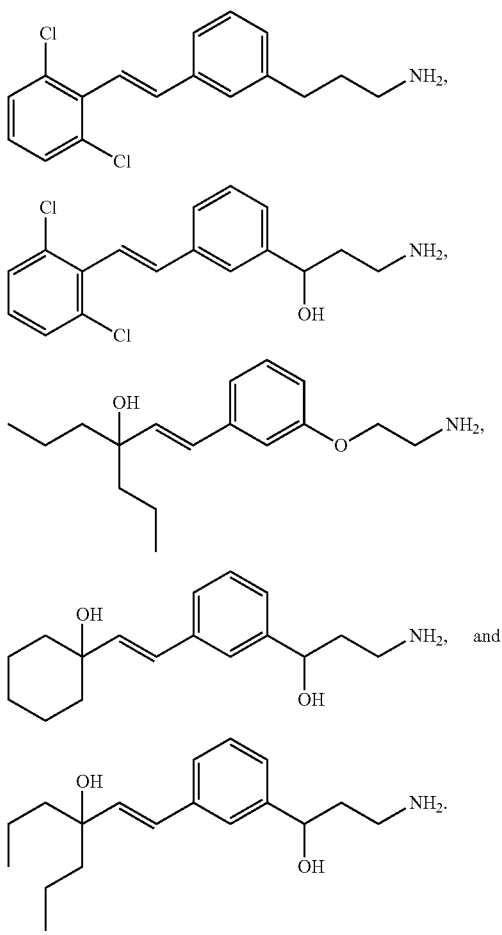

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or stereoisomer, N-oxide or a pharmaceutically acceptable salt thereof, selected from:

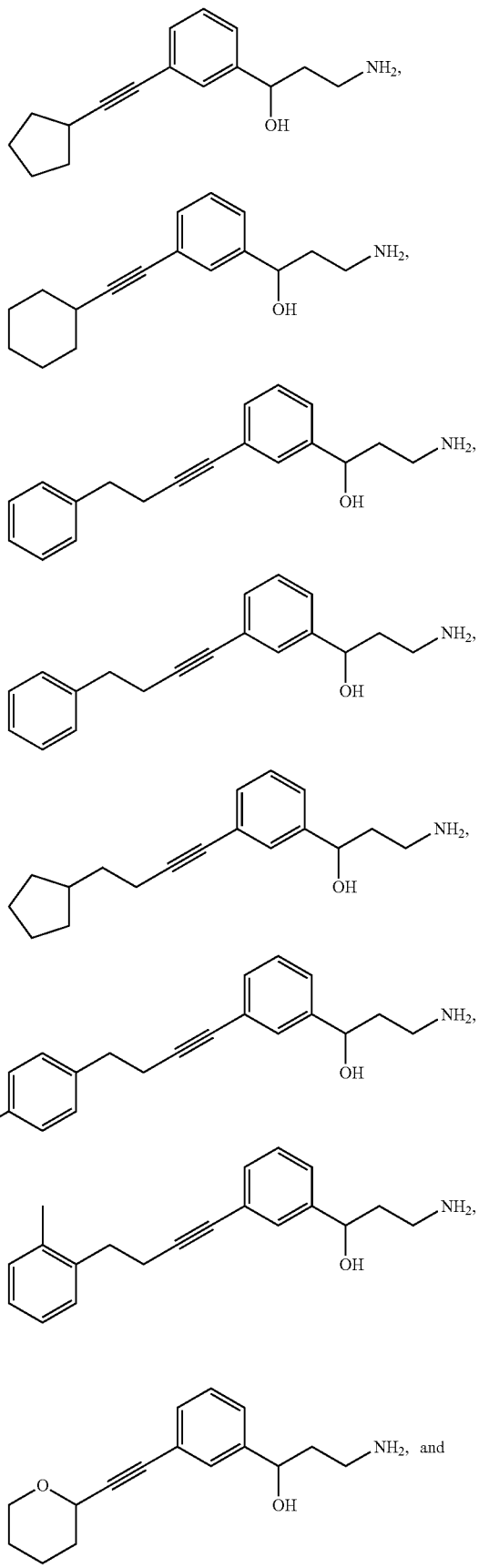

-continued

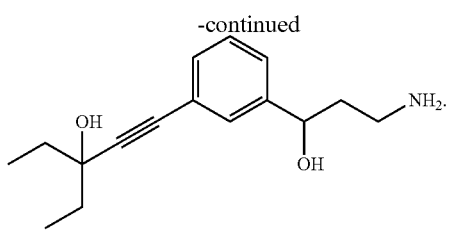

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or tautomer, stereoisomer, N-oxide or a pharmaceutically acceptable salt thereof, selected from:

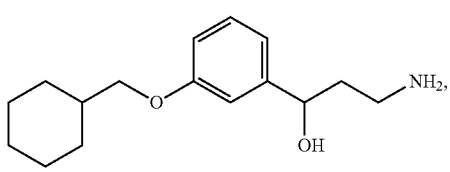 [SMILES: NCCC(O)c1cccc(OCC2CCCCC2)c1]

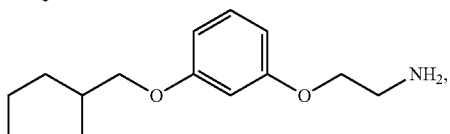

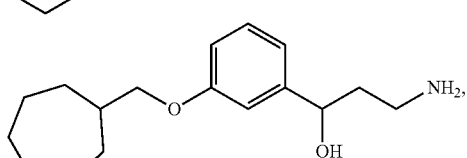

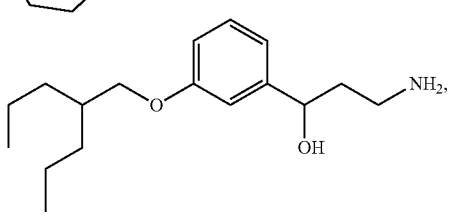

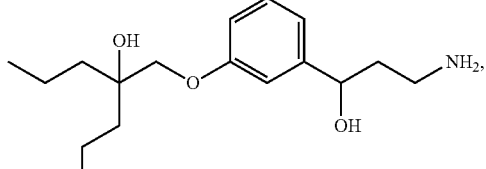

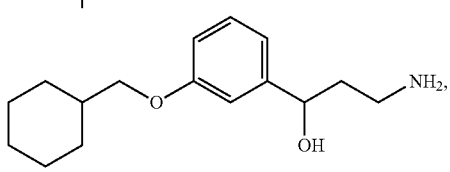

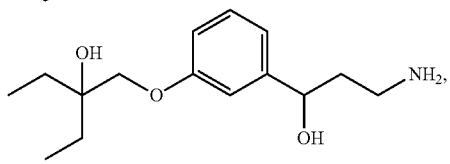

-continued

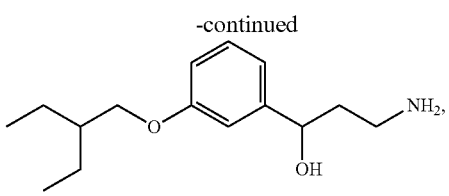

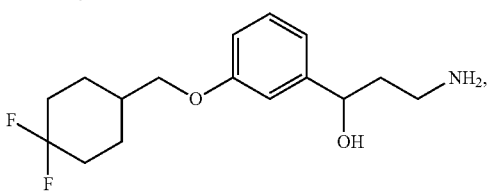

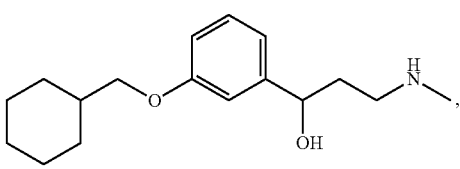

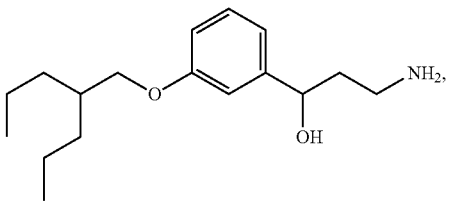

-continued

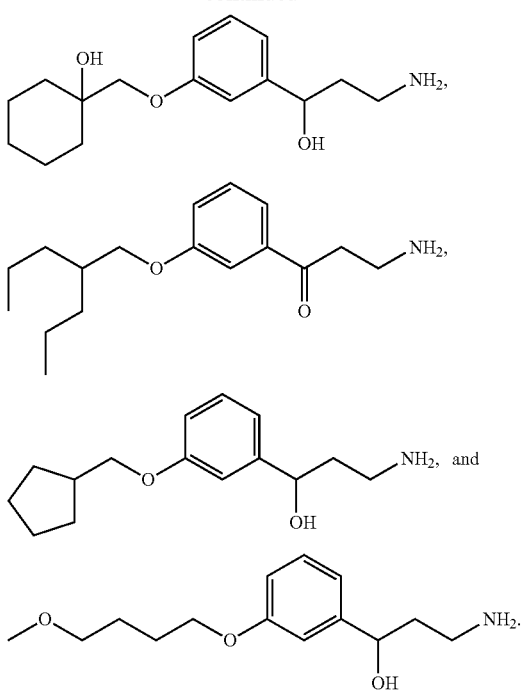

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or stereoisomer, N-oxide or a pharmaceutically acceptable salt thereof, selected from:

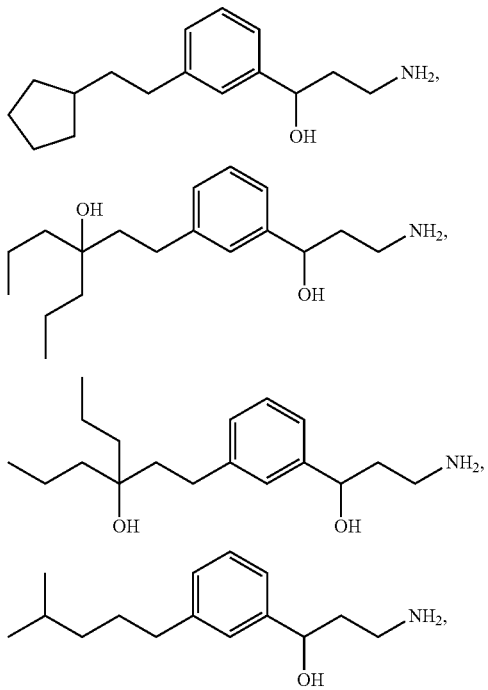

-continued

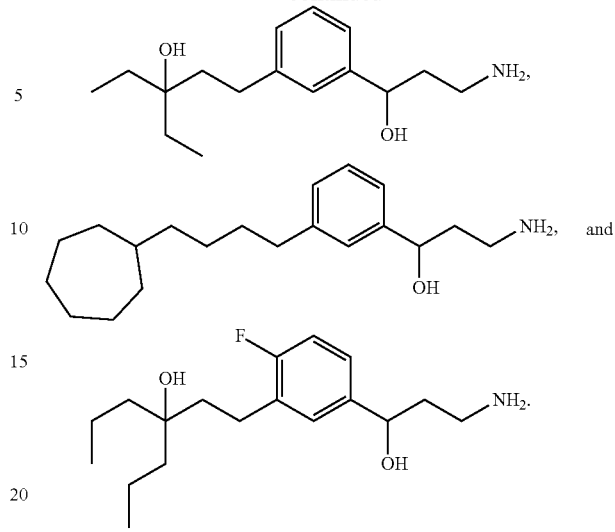

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or tautomer, stereoisomer, N-oxide or a pharmaceutically acceptable salt thereof, selected from:

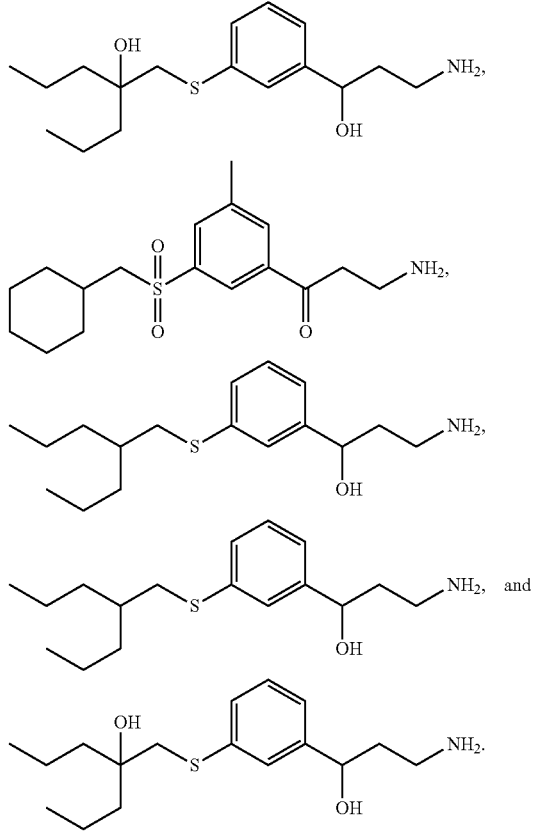

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or tautomer, stereoisomer, N-oxide or a pharmaceutically acceptable salt thereof, selected from:

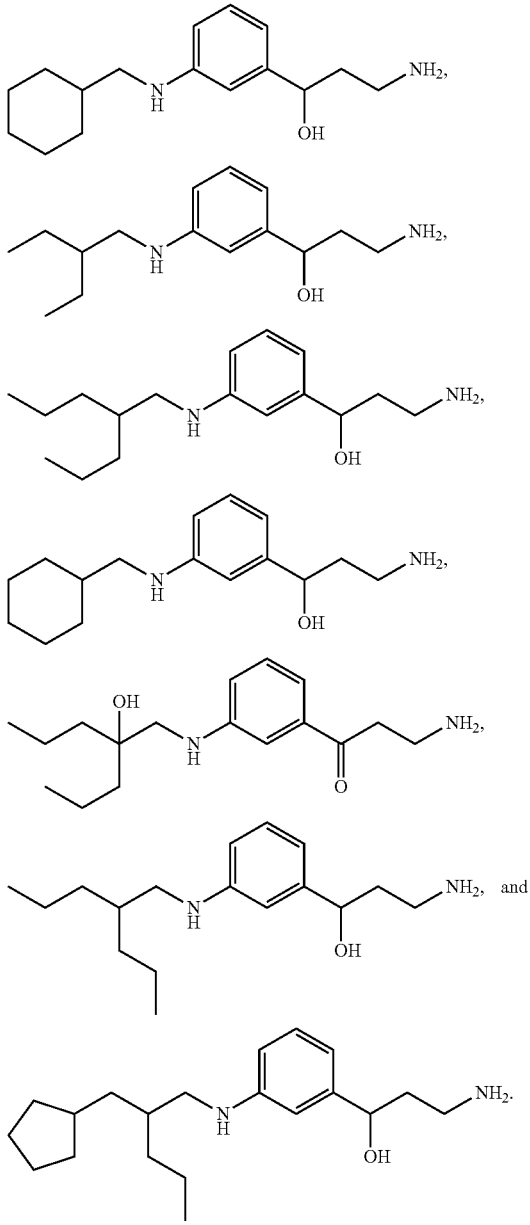

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or stereoisomer, N-oxide or a pharmaceutically acceptable salt thereof, having the structure:

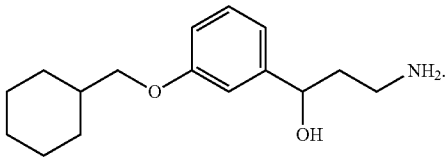

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, stereoisomer, N-oxide or a pharmaceutically acceptable salt thereof, having the structure:

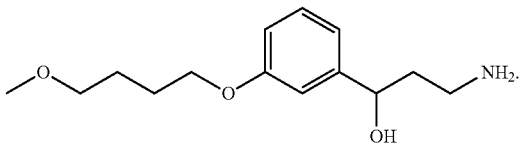 [SMILES: COCCCCOc1cccc(C(O)CCN)c1]

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or stereoisomer, N-oxide or a pharmaceutically acceptable salt thereof, having the structure:

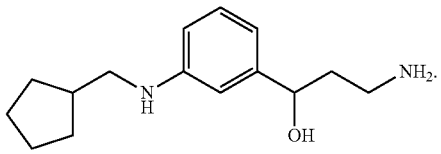 [SMILES: NCCC(O)c1cccc(NCC2CCCC2)c1]

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or stereoisomer, N-oxide or a pharmaceutically acceptable salt thereof, having the structure:

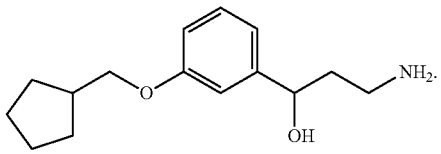 [SMILES: NCCC(O)c1cccc(OCC2CCCC2)c1]

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or stereoisomer, N-oxide or a pharmaceutically acceptable salt thereof, having the structure:

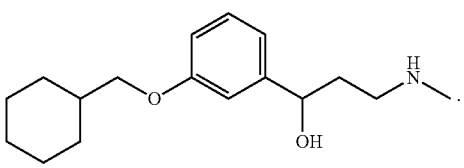 [SMILES: CNCCC(O)c1cccc(OCC2CCCCC2)c1]

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or stereoisomer, N-oxide or a pharmaceutically acceptable salt thereof, having the structure:

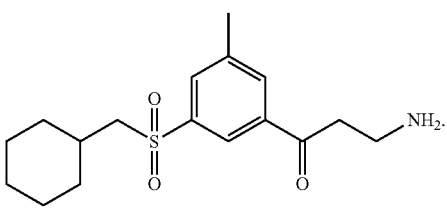 [SMILES: Cc1cc(C(=O)CCN)cc(S(=O)(=O)CC2CCCCC2)c1]

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition comprises a compound, or stereoisomer, N-oxide or a pharmaceutically acceptable salt thereof, having the structure:

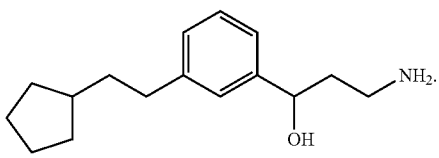 [SMILES: NCCC(O)c1cccc(CCC2CCCC2)c1]

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein the composition is administered to the patient orally. Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient, wherein the composition is administered once per day. Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient, wherein treatment results in improvement of central vision in the patient.

Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient further comprising administering one or more additional therapeutic regimens. Another embodiment provides the method for treating an ophthalmic disease or disorder associated with diabetes in a patient; treating or preventing retinopathy of prematurity in a patient; or treating an ophthalmic disease or disorder associated with neovascularization in the eye of a patient wherein said one or more therapeutic regimens is laser therapy, cryotherapy, fluorescein angiography, vitrectomy, corticosteroids, anti-vascular endothelial growth factor (VEGF) treatment, vitrectomy for persistent diffuse diabetic macular edema, pharmacologic vitreolysis in the management of diabetic retinopathy, fibrates, renin-angiotensin system (ras) blockers, peroxisome proliferator-activated receptor gamma agonists, Anti-Protein Kinase C (PKC), islet cell transplantation, therapeutic oligonucleotides, growth hormone and insulin growth factor (IGF), control of systemic factors or a combination thereof.

Another embodiment provides the method for treating an ophthalmic disease or disorder associated with diabetes in a patient wherein the ophthalmic disease or disorder associated with diabetes is diabetic retinopathy. Another embodiment provides the method for treating an ophthalmic disease or disorder associated with diabetes in a patient wherein the ophthalmic disease or disorder associated with diabetes is non-proliferative diabetic retinopathy. Another embodiment provides the method for treating an ophthalmic disease or disorder associated with diabetes in a patient wherein the ophthalmic disease or disorder associated with diabetes is proliferative diabetic retinopathy. Another embodiment provides the method for treating an ophthalmic disease or disorder associated with diabetes in a patient wherein the ophthalmic disease or disorder associated with diabetes is diabetic maculopathy. Another embodiment provides the method for treating an ophthalmic disease or disorder associated with diabetes in a patient wherein the ophthalmic disease or disorder associated with diabetes is diabetic macular edema. Another embodiment provides the method for treating an ophthalmic disease or disorder associated with diabetes in a patient wherein the ophthalmic disease or disorder associated with diabetes is neovascular glaucoma. Another embodiment provides the method for treating an ophthalmic disease or disorder associated with diabetes in a patient wherein the ophthalmic disease or disorder associated with diabetes is macular ischemia.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12A provides the results of G4 M Day 8 4H Plasma. FIG. 12B provides the results of G3 M 4H Retinal Pigmented Epithelium.

FIG. 16A depicts isolectin staining of flatmount preparations of retina. Neovascular areas are outlined in red. FIG. 16B is a histogram comparing % neovascularization in the various treatment groups. FIGS. 16C and 16D show that ACU-4429 decreased 11-cis-RAL concentrations in eyes and, therefore, visual cycle isomerase activity in a dose dependent manner (ED50 0.88 mg/kg). The difference between ACU-4429 and vehicle was statistically significant ($P<0.01$). FIGS. 16E and 16F show neovascularization in left eyes (measured in isolectin-stained flatmount preparations) decreased in a dose-dependent manner with ACU-4429; this decrease is significant at 3.0 and 10.0 mg/kg, by 1-way-ANOVA comparison of vehicle (water) at 21% $O_2$, vehicle (water) at 75% $O_2$, and ACU-4429 treatments.

DETAILED DESCRIPTION OF THE INVENTION

Figure 1:
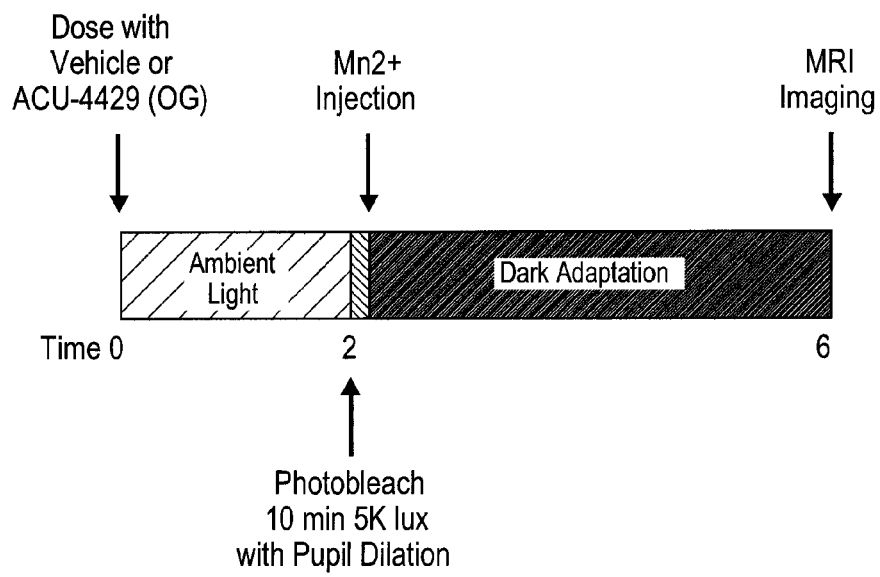
FIG. 1 is a graph depicting the timeline for Groups 1-3 as described in Example 3.

The present disclosure relates to methods for treating diabetic retinopathy. As used herein, "Diabetic retinopathy" refers to changes in the retina due to the micro vascular changes seen in diabetes. The blood vessels that supply oxygen to the retina of the eye are damaged due to long-term high levels of blood sugar (hyperglycemia). The disease generally develops slowly over a period of months but over time, diabetic retinopathy can get worse and cause vision loss. Diabetic retinopathy usually affects both eyes. Diabetic retinopathy progresses from mild non-proliferative abnormalities, characterized by increased vascular permeability, to moderate and severe non-proliferative diabetic retinopathy (NPDR), characterized by vascular closure, to proliferative diabetic retinopathy (PDR), characterized by the growth of new blood vessels on the retina and posterior surface of the vitreous. Macular edema, characterized by retinal thickening from leaky blood vessels, can develop at all stages of retinopathy. Furthermore conditions such as pregnancy, puberty, blood glucose control, hypertension, and cataract surgery can accelerate these changes.

Non-proliferative diabetic retinopathy, proliferative diabetic retinopathy and diabetic maculopathy are the three main types of diabetic retinopathy.

Non-Proliferative Diabetic Retinopathy (NDPR) is considered as the early stage of retinopathy and is the most common seen in diabetics. The tiny blood vessels in the retina are only mildly affected, but may form bulges (micro aneurysms) and connections with each other (intraretinal micro vascular anomalies) and/or leak fluid (edema), protein deposits (exudates) and blood (hemorrhage). Another typical sign of non-proliferative diabetic retinopathy (NPDR) is the presence of puffy white patches on the retina (cotton wool spots). These changes can occur anywhere throughout the retina, including the macula.

There are three stages of non-proliferative diabetic retinopathy which are detailed below:

(1) Mild Non-proliferative Diabetic Retinopathy: At this earliest stage, at least one micro aneurysm may occur. Micro aneurysms are small areas of balloon-like swelling in the retina's blood vessels.

(2) Moderate Non-proliferative Diabetic Retinopathy: As the disease progresses, some blood vessels that nourish the retina are blocked.

(3) Severe Non-proliferative Diabetic Retinopathy: Many more blood vessels are blocked, depriving several areas of the retina of blood supply. These areas of the retina send signals to the body to grow new blood vessels for nourishment.

Non-proliferative diabetic retinopathy should not cause any problems to the patient, as the vision remains normal as long as the macula is not affected. However, as the symptoms of diabetic retinopathy are generally not visible in this stage, it is recommended that regular retinal screening eye tests should be done to monitor the signs of progression to more serious stages of retinopathy.

Proliferative Diabetic Retinopathy (PDR):

This stage comes after severe non-proliferative diabetic retinopathy and is characterized by the growth of abnormal new blood vessels in the eye. When the diabetes causes the blood vessels to become blocked, parts of the eye and retina develop ischemia, as they become starved of oxygen and nutrients. The eye tries to respond to this condition, by growing a new blood supply to the oxygen starved areas. Unfortunately, fragile new blood vessels that bleed easily are formed instead. This process is called neo-vascularization. These abnormal new blood vessels grow in the wrong place on the surface of the retina and into the vitreous gel. Vitreous hemorrhage occurs when these new blood vessels bleed into the vitreous cavity. The blood blocks light that enters the eye from reaching the retina. The amount of sight loss can be mild to severe, and depends on how much blood is in the eye. The vision might slowly improve as the hemorrhage gradually clears over several months.

Abnormal new blood vessels also cause the formation of scar tissue which pulls on the retina and may result in tractional retinal detachment. The retinal detachment can affect any part of the retina. If it affects the macula, the patient might lose his/her central vision and it can be treated only with surgery.

Diabetic Maculopathy:

Diabetic maculopathy is the most common cause of visual loss in diabetes. It occurs when the macula becomes affected by the retinopathy changes caused by diabetes. The macula is located at the center of the retina and is important for central vision and for seeing fine details clearly. Therefore, the central vision and ability to see detail will be affected in the patients that develop diabetic maculopathy. For instance, the affected individuals might find it difficult to recognize faces in the distance or to read small prints. The amount of sight loss may be mild to severe. However, even in the worst cases, the peripheral (side) vision that allows the individual to get around at home and outside will remain unaffected.

Diabetic retinopathy (DR) is an ocular disorder characterized by excessive angiogenesis that develops in diabetes due to thickening of capillary basement membranes, and lack of contact between pericytes and endothelial cells of the capillaries. Loss of pericytes increases leakage of the capillaries and leads to breakdown of the blood-retina barrier. Diabetic retinopathy is the result of microvascular retinal changes. Hyperglycemia-induced pericyte death and thickening of the basement membrane lead to incompetence of the vascular walls. These damages change the formation of the blood-retinal barrier and also make the retinal blood vessels become more permeable. Small blood vessels—such as those in the eye—are especially vulnerable to poor blood sugar (blood glucose) control. An over-accumulation of glucose and/or fructose damages the tiny blood vessels in the retina. Macular edema can also develop when the damaged blood vessels leak fluid and lipids onto the macula. These fluids make the macula swell, which blurs vision. This damage also results in a lack of oxygen at the retina.

As the disease progresses, the lack of oxygen in the retina stimulates angiogenesis along the retina and in the clear, gel-like vitreous humor that fills the inside of the eye. Without timely treatment, these new blood vessels can bleed, cloud vision, and destroy the retina. Fibrovascular proliferation can also cause tractional retinal detachment. The new blood vessels can also grow into the angle of the anterior chamber of the eye and cause neovascular glaucoma.

Vision loss from diabetic maculopathy occurs in 2 ways.

Diabetic macular edema (DME) is the swelling and thickening of the macula. This is due to fluid leakage from the retinal blood vessels in the macula. The vision becomes blurry because the structure and function of the macular photoreceptor cells becomes disrupted. Vision loss from macular edema can be controlled with laser and injections into the eyeball.

Macular ischemia occurs when the tiny retinal blood vessels (capillaries) to the macula close up. The vision becomes blurry because the macula does not receive enough blood supply for it to work properly. Unfortunately, there are no effective treatments for macular ischemia. Macular edema is due to leakage of fluid from the retinal blood vessels. Hard exudates are the yellowish deposits seen on the retina. They are caused by leakage of protein material.

The following medical conditions are some of the possible causes of diabetic retinopathy.

Diabetes: Prolonged hyperglycemia (high blood glucose levels) affects the anatomy and function of retinal capillaries. The excess glucose is converted into sorbitol when it is diverted to alternative metabolic pathways. Sorbitol leads to death or dysfunction of the pericytes of the retinal capillaries. This weakens the capillary walls allowing for the formation of micro aneurysms, which are the earliest signs of diabetic retinopathy. The weak capillary walls can also be responsible for increased permeability and the exudates. Due to the predisposition to increased platelet aggregation and adhesion (blood clot formation) as a result of diabetes, the capillary circulation becomes sluggish or even totally impaired by an occlusion. This can also contribute to the development of diabetic retinopathy.

Type 1 and Type 2 diabetes: Individuals diagnosed with type 1 diabetes, are considered insulin-dependent as they require injections or other medications to supply the insulin that the body is unable to produce on its own. Due to lack of insulin the blood sugar is unregulated and levels are too high. Individuals with type 2 diabetes are considered non-insulin-dependent or insulin-resistant. The individuals affected with this type of diabetes, produce enough insulin but the body is unable to make proper use of it. The body then compensates by producing even more insulin, which can cause an accompanying abnormal increase in blood sugar levels. All people with Type I diabetes (juvenile onset)

and with Type II diabetes (adult onset) are at risk of developing diabetic retinopathy. However, people with Type 1 diabetes are more likely to cause retinopathy compared to type 2 diabetes.

Diabetes mellitus type 1 and Diabetes mellitus type 2: People with Diabetes mellitus type 1 and type 2 are at increased risk of developing diabetic retinopathy.

Excessive alcohol: Alcohol if used to extreme reduces Vitamin B12 and thiamine levels. However, alcohol consumption alone is not associated with diabetic retinopathy, the consumption of empty calories from alcohol makes adhering to a calorie-restricted diabetic diet very difficult and it is unclear that what effect moderate alcohol has on retinopathy.

Hypertension and other vascular risk factors such as obesity and dyslipidaemia can influence the onset and progression of retinopathy.

High cholesterol: Cholesterol can exacerbate retinopathy by hardening of large artery blood vessels and can cause damage to the small blood vessels of the eye.

Renal disease, as evidenced by proteinuria and elevated urea/creatinine levels, is an excellent predictor of the presence of retinopathy.

Pregnancy: It can exacerbate existing retinopathy though probably not cause it directly. Women with diabetes have a slightly higher risk during pregnancy. It is recommended that all pregnant women with diabetes have dilated eye examinations each trimester to protect their vision.

Kidney impairment: Associated with diabetic retinopathy, though it appears that diabetic retinopathy leads to kidney impairment rather than vice versa.

Chromosome 15q deletion: A rare chromosomal disorder involving deletion of genetic material from the long arm of chromosome 15.

It is thought that intraocular surgery may possibly increase the risk of progression of diabetic retinopathy.

There are often no symptoms in the earliest stages of non-proliferative diabetic retinopathy. The signs and symptoms of diabetic retinopathy are commonly presented as the disease progresses toward advanced or proliferative diabetic retinopathy. The diagnostic signs of diabetic retinopathy include one more of the following: changes in the blood vessels; retinal swelling (macular edema); pale deposits on the retina; damaged nerve tissue; visual appearance of leaking blood vessels; loss of central or peripheral vision; temporary or permanent vision loss; development of a scotoma or shadow in the field of view; spotty, blurry, hazy or double vision; eye pain; near vision problems unrelated to presbyopia; spots or dark strings floating in the vision (floaters); impaired color vision; vision loss; a dark or blind spot in the central vision; poor or reduced night vision; venous dilation and intraretinal micro vascular abnormalities; in the advanced stage of retinopathy tiny blood vessels grow along the retina, in the clear, gel-like vitreous humor that fills the inside of the eye; nerve damage (neuropathy) affecting ocular muscles that control eye movements; involuntary eye movement (nystagmus); fluctuating and progressive deterioration of vision; macular edema; macular ischemia; traction retinal detachment; sudden, severe painless vision loss; increased vascular permeability, leading to edema; endothelial cell proliferation; flashes of light (photopsias) or defects in the field of vision; presence of abnormal blood vessels on the iris (rubeosis or nvi), cataract (associated with diabetes) and vitreous cells (blood in the vitreous or pigmented cells if there is a retinal detachment with hole formation); micro aneurysms—physical weakening of the capillary walls which predisposes them to leakages; hard exudates—precipitates of lipoproteins/other proteins leaking from retinal blood vessels; haemorrhages—rupture of weakened capillaries, appearing as small dots/larger blots or 'flame' haemorrhages that track along nerve-fiber bundles in superficial retinal layers (the haemorrhage arises from larger and more superficial arterioles); cotton wool spots—build-up of axonal debris due to poor axonal metabolism at the margins of ischaemic infarcts; and neo-vascularization—an attempt (by residual healthy retina) to revascularize hypoxic retinal tissue.

The present disclosure also relates to the methods of using visual cycle modulation (VCM) compounds to treat retinopathy of prematurity (ROP). The work described herein provides the first demonstration of an effect of systemic treatment with a non-retinoid VCM on a retinopathy in an immature eye. One key element of this process is a high $O_2$ content when subjects are new-born is the key element. Premature infants are put into a high oxygen atmosphere to support the immature lung function where the high oxygen concentration suppresses the normal development of retinal vasculature. When the infant is returned to normal air, the retina becomes ischemic due to the under developed vasculature. The ischemia triggers VEGF expression and neo-vascularization. See, for example, FIG. 4B. VCMs work by increasing apo-rhodopsin that reduces the dark current and hence oxygen consumption.

Described herein are VCM compounds for the treatment or prevention of diseases or disorders of the retina, and particularly, VCM compounds for the treatment or prevention of retinal diseases or disorders related to or involving vascular abnormalities, such as, for example, ROP. The methods described herein relate to the administration of the VCM compounds that modulate the visual cycle.

As a system, the mammalian retina is subject to diseases that affect the balanced interconnection of the neural retina and the vasculature that nourishes it; visual loss occurs when this balance is disturbed. Diseases such as photoreceptor degenerations that primarily affect the neural retina also affect the retinal vasculature. Diseases that are clinically characterized by abnormality in the choroidal or retinal vasculature, such as ROP, also affect the retinal neurons. These conditions all involve hypoxic ischemic disorders of neural tissue. Photoreceptors are specialized cells that have the highest oxygen requirements of any cell in the body (Steinberg, R., *Invest. Ophthalmol. Vis. Sci.*, (1987) 28: 1888-1903), which plays a role in all hypoxic ischemic diseases of the retina.

In normal development, as the rod photoreceptors differentiate and begin to produce rhodopsin (the molecule responsible for the capture of light); their extraordinarily high oxygen demands render the retina hypoxic, driving the growth of the retinal blood vessels. However, in ROP, supplemental oxygen administered for the acute cardiopulmonary care of the prematurely born infant renders the retina hyperoxic, interrupting normal vascular growth and leaving the peripheral retina avascular. Upon cessation of the supplemental oxygen, the peripheral retina becomes hypoxic. Hypoxia instigates a molecular cascade that leads to the formation of the abnormal retinal blood vessels that are clinically used to diagnose ROP. Even though a premature infant is subjected to high ambient oxygen, immature lungs and other medical complications often lead to fluctuations in blood oxygen and, consequently, to episodes of both hypoxia and hyperoxia at the retina which affect the sensitive photoreceptors. The developing neural retina and its vasculature are under cooperative molecular control, and the vascular abnormalities of ROP are related to the function of the neural retina. Recent studies have found that the degree of dysfunction of the rods in ROP helps predict the degree of abnormality observed in the retinal vasculature, but the degree of abnormality observed in the retinal vasculature may not help predict the degree of dysfunction of the rods in ROP. Thus, the rods cause ROP.

As used herein, an "immature retina" refers to a retina of a preterm infant or a retina of similar morphology/function to that of a pre-term infant retina. An immature retina can be characterized by the presence of poorly developed or disorganized blood vessels with or without the presence of scar tissue. In general, a human preterm infant is one born at 37 weeks gestation, or earlier. Conversely, the term "retinal maturity" refers to a retina of a full-term infant or a retina of similar morphology/function to that of a full-term infant.

As used herein, the phrases "reduces rod energy demand" or "suppresses rod energy demand" refer to a reduction in oxygen demand of a rod cell of at least 10%; preferably the reduction of oxygen demand of a rod cell is at least 20%, at least 30%, at least 40%, at least 50%, at least 60%, at least 70%, at least 80%, at least 90% or more. In general, it is preferred that the oxygen demand of a rod cell is maintained below the level necessary to induce pathological angiogenesis (i.e., blood vessel growth) or vascular abnormalities.

As used herein, the term "vascular abnormalities" is used to refer to an abnormal or pathological level of vascular blood vessel growth (e.g., angiogenesis) or morphology (e.g., tortuosity) that does not permit proper development of the retina to "retinal maturity" as that term is used herein. One of skill in the art can titrate the amount of agent administered or the timing of administration to maintain the growth and morphology of blood vessels below that of pathological blood vessel growth as assessed by, for example, Laser Doppler Blood Flow analysis. In an alternative embodiment, the level of tortuosity of retinal blood vessels is used to assess the degree of pathological blood vessel morphology and/or growth. Methods for measuring tortuosity are further described herein.

As used herein, the term "supplemental oxygen" refers to a concentration of oxygen above that of ambient air (i.e., about 20-21%) that is necessary to maintain blood oxygen levels in a subject at a desired level. In general, supplemental oxygen is supplied in a clinical setting to maintain a blood oxygen level of 100% as assessed using, for example, transcutaneous oxygen monitoring. Monitoring blood oxygen levels and altering the level of "supplemental oxygen" to maintain, for example, a 100% blood oxygen level is a standard procedure in a clinical setting (e.g., a neonatal intensive care unit) and is well known to those of skill in the art of medicine.

Vascular and Neural Diseases of the Retina

Despite advancements in the medical management of neovascular diseases of the retina, such as retinopathy of prematurity (ROP), retinal neurovascular diseases remain the leading cause of blindness worldwide.

For ROP, current treatment is photocoagulation of the peripheral vasculature, which carries its own negative consequences, and experimental approaches such as treatment with anti-angiogenic pharmaceuticals, that have unknown efficacy. Because rod photoreceptors are unique to the eye and have among the highest oxygen requirements of any cell in the body, they may play a role in hypoxic ischemic neovascular retinal diseases (Arden et al., *Br J Ophthalmol* (2005) 89:764; and Fulton et al., *Doc Ophthalmol*, (2009) 118(1):55-61). Rat models of ROP provide an in vivo system in which the relation of the photoreceptors to the retinal vasculature can be studied and manipulated.

Abnormal retinal function is a feature of neovascular retinal diseases. (Fulton et al., *Doc Ophthalmol*, (2009) 118(1):55-61). Vision loss in neovascular retinal disease results from blood vessel abnormalities and the severity of lifelong retinal dysfunction that persists after the blood vessel abnormalities resolve is related to the severity of the antecedent vascular disease (Fulton et al., *Arch Ophthalmol* (2001) 119:499). Data from rat models of ROP, however, show that dysfunction of the rod photoreceptors precedes the vascular abnormalities by which ROP is conventionally defined and predicts their severity (Reynaud, and Dorey, *Invest Ophthalmol Vis Sci* (1994) 35:3169; Akula, *Invest Ophthalmol Vis Sci* (2007) 48: 4351). Abnormalities in vascular morphology are the main diagnostic criterion of ROP; however, ROP is mainly a disorder of the neural retina with secondary vascular abnormalities. The appearance of the vascular abnormalities that characterize acute ROP is coincident with developmental elongation of the rod photoreceptors' outer segments and accompanying increase in the retinal content of rhodopsin (Lutty et al., *Mol Vis* (2006) 12: 532; and Dembinska et al., *Invest Ophthalmol Vis Sci* (2002) 43:2481).

Rod Cell Physiology and Metabolism

The rods perform three linked, metabolically demanding processes: generation of the dark current, maintenance of the visual pigment (the visual cycle), and outer segment turnover, all of which ensue concomitant to developmental elongation of the rod outer segments (ROS) and increase of the rhodopsin content of the eye. The signal transduction mechanism of the rods is physiologically unique. In darkness, sodium and other cations intromitted through cyclic guanosine monophosphate (cGMP) gated channels in the ROS are expelled by pumps in the rod inner segment (RIS) so rapidly that a volume equal to the entire cytosol is circulated every half minute (Hagins, et al., *Proc Nad Acad Sci USA* (1989) 86:1224). The molecular cascade initiated by photon capture by rhodopsin following a flash of light and leading to a reduction of cGMP leads the dark current to decay following the form of a delayed Gaussian that can be described by an intrinsic amplification constant, A (Lamb and EPugh, *J Physiol* (1992) 449: 719; and Pugh and Lamb, *Biochem Biophys Acta* (1993) 1141:111).

Following photon capture, rhodopsin's chromophore (retinol) undergoes an isomeric change which frees it from opsin and initiates phototransduction. Spent chromophore is passed from the ROS to the retinal pigment epithelium (RPE) where it undergoes a series of transformations before being returned to the ROS through the apical processes of the RPE as retinol again. There it becomes covalently linked to its active-site lysine in opsin, becoming rhodopsin again and completing the visual cycle (R. R. Rando, *Chem Rev* (2001) 101:1881). The rate-limiting step in the visual cycle mediated by the isomerohydrolase enzyme complex, RPE65 (Moiseyev et al., *Proc Natl Acad Sci USA* (2005) 102: 12413). Other byproducts of photo-transduction in the ROS are expelled through a process of circadian shedding of the ROS tips; each RPE cell phagocytizes thousands of disks shed from 30-50 embedded rods each day (R. W. Young, *J Cell Biol* (1967) 33:61). Controlled down-regulation of the visual cycle through targeted inhibition of RPE65 activity lowers the flux of retinoids through the ROS/RPE complex; this would render the rods less vulnerable to insult from hyperoxia and hypoxia (Wellard et al., *Vis Neurosci* (2005) 22:501) by reducing their metabolic demands. It may also slow phagocytosis and thus lengthen the rod outer segments.

Translation from Animal Models to Patients

Photoreceptors are nestled closely to the choroidal vasculature. Highly organized post-receptor retinal neurons form layers that are supplied by the retinal vessels. Although the choroid is the principal supply to the photoreceptors, degeneration of the photoreceptors is, nonetheless, associated with attenuation of the retinal arterioles (Hansen et al., *Vision Research*, 48(3):325-31 (2008)). Because the photoreceptor layer is such an extraordinary oxygen sink, while not wishing to be bound by theory, it is presumed that, as photoreceptors degenerate, their metabolic demands wane and the retinal vasculature becomes attenuated consequent to the neural retina's chronic lower requirement for oxygen (Hansen et al., *Vision Research*, 48(3):325-31 (2008)).

A tight link between the photoreceptors and the retinal vascular network is evident in the developing retina. Post-receptor cells differentiate before the photoreceptors, which are the last retinal cells to mature. As the formation of rod outer segments advances in a posterior to peripheral gradient, so too does vascular coverage. Thus, concurrent and cooperative development of the neural and vascular components characterizes normal retinal maturation. In preterm infants, the age of onset of ROP is around the age of rapid developmental increase in rod outer segment length and consequent increase in rhodopsin content. In addition to immature photoreceptors and retinal vasculature, the preterm infant has immature lungs that create a precarious respiratory status with attendant risk of hypoxic injury to immature cells. Clinically, this is countered by administration of supplemental oxygen, but both high and low oxygen levels are known to injure the immature photoreceptors (Fulton et al. *Invest. Ophthalmol. Vis. Sci.*, (1999) 40: 168-174; and Wellard et al., *Vis. Neurosci.*, (2005) 22: 501-507).

Rat models of ROP are induced by rearing pups in habitats with alternating periods of relatively high and low oxygen during the critical period of rod outer segment elongation (Akula et al., *Invest. Ophthalmol. Vis. Sci.*, (2007) 48: 4351-9; Akula et al., *Invest. Ophthalmol. Vis. Sci.*, (2007) 48: 5788-97; Dembinska et al., *Invest. Ophthalmol. Vis. Sci.*, (2001) 42: 1111-1118; Liu et al., *Invest. Ophthalmol. Vis. Sci.*, (2006) 47: 5447-52; Liu et al., *Invest. Ophthalmol. Vis. Sci.*, (2006) 47: 2639-47; Penn et al., *Invest. Ophthalmol. Vis. Sci.,* 1995. 36: 2063-2070). Following induction, abnormalities of the retinal vasculature ensue, as do abnormalities of the structure and function of the neural retina (Fulton et al. *Invest. Ophthalmol. Vis. Sci.*, (1999) 40: 168-174; Akula et al., *Invest. Ophthalmol. Vis. Sci.*, (2007) 48: 4351-9; Akula et al., *Invest. Ophthalmol. Vis. Sci.*, (2007) 48: 5788-97; Dembinska et al, *Invest. Ophthalmol. Vis. Sci.*, (2001) 42: 1111-1118; Liu et al., *Invest. Ophthalmol. Vis. Sci.*, (2006) 47: 5447-52; Liu et al., *Invest. Ophthalmol. Vis. Sci.*, (2006) 47: 2639-47; Reynaud et al., *Invest. Ophthalmol. Vis. Sci.*, (1995) 36:2071-2079). The abnormalities in the morphology of the retinal vasculature and in the function of the neural retina in ROP rats are similar to those found in pediatric ROP patients (Dembinska et al., *Invest. Ophthalmol. Vis. Sci.*, (2001) 42: 1111-1118; Liu et al., *Invest. Ophthalmol. Vis. Sci.*, (2006) 47: 5447-52; Liu et al., *Invest. Ophthalmol. Vis. Sci.*, (2006) 47: 2639-47; Reynaud et al., *Invest. Ophthalmol. Vis. Sci.*, (1995) 36:2071-2079; Barnaby, A. M., *Invest. Ophthalmol. Vis. Sci.*, (2007). 48:4854-60; Fulton et al., *Arch. Ophthalmol.*, (2001)119: 499-505; Gelman, R., *Invest. Ophthalmol. Vis. Sci.*, (2005) 46(12): 4734-4738; Moskowitz et al., *Optometry & Vision Science*, (2005) 82: 307-317; Fulton, A. B., *Invest. Ophthalmol. Vis. Sci.,* 49(2):814-9 (20089)). Thus, rat models can be extrapolated to human treatment.

Albino rat models of ROP are used to study the neural and vascular characteristics of the retina during development (Akula et al., *Invest. Ophthalmol. Vis. Sci.*, (2007) 48: 4351-9; Akula et al., *Invest. Ophthalmol. Vis. Sci.*, (2007) 48: 5788-97; Liu, K., *Invest. Ophthalmol. Vis. Sci.*, (2006) 47: 5447-52; Liu et al., *Invest. Ophthalmol. Vis. Sci.*, (2006) 47: 2639-47). Different schedules of oxygen exposure induce a range of effects on the retinal vasculature and the neural retina that model the gamut of retinopathy, mild to severe, observed in human ROP cases. The oxygen exposures are timed to impact the retina during the ages when the rod outer segments are elongating and the rhodopsin content of the retina is increasing. Longitudinal measures of electroretinographic (ERG) responses and retinal vascular features are obtained in infant (about 20 day old), adolescent (about 30 day old), and adult (about 60 day old) rats.

Assessment of Neural Function

ERG is used to characterize neural function. ERG responses to full-field stimuli over a range of intensities are recorded from the dark-adapted animal as previously described in detail (Akula et al., *Invest. Ophthalmol. Vis. Sci.*, (2007) 48: 4351-9). To summarize rod photoreceptor activity, a model of the activation of phototransduction is fit to the a-waves and the resulting sensitivity (SROD) and saturated amplitude (RROD) parameters are calculated. Post-receptor activity is represented by the b-wave. The stimulus/response functions are summarized by the saturated amplitude (Vmax) and the stimulus producing a half-maximum response (log s); these parameters are derived from the Michaelis-Menten function fit to the b-wave amplitudes (Hood Birch, *Invest. Ophthalmol. Vis. Sci.*, (1994) 35: 2948-2961; Lamb, and Pugh, *J. Physiol.* (Lond). (1992) 449: 719-758; Pugh. and Lamb, *Biochim. Biophys. Acta,* 1993. 1141: 111-149; Pugh and Lamb, in Handbook of biological physics. Volume 3 (2000), Elsevier Science. p. 183-255; Akula et al., Invest. *Ophthalmol. Vis. Sci.*, (2007) 48: 4351-9).

Assessment of Vascular Characteristics

Retinal vascular parameters are derived using image analysis software and may be applied to digital fundus photographs (Akula et al., *Invest. Ophthalmol. Vis. Sci.*, (2007) 48: 4351-9; Martinez-Perez, M. E., (2001), Imperial College: London; Martinez-Perez et al., *Trans. Biomed. Eng.*, (2002) 49: 912-917). Integrated curvature (IC), which agrees well with subjective assessment of vascular tortuosity reported by experienced clinicians, may be used to specify the vascular status of each fundus (Gelman, R. M. *Invest. Ophthalmol. Vis. Sci.*, (2005) 46(12): 4734-4738). Both arterioles and venules are significantly affected by ROP. It has been found, however, that the arterioles are markedly affected while the venules are less so; therefore, the arteriolar parameter ICA is used in the analyses described herein (Akula et al., *Ophthalmol. Vis. Sci.*, (2007) 48: 4351-9; Liu et al., *Invest. Ophthalmol. Vis. Sci.*, (2006) 47: 5447-52; Liu et al., *Invest. Ophthalmol. Vis. Sci.*, (2006) 47: 2639-47; Gelman, R., M. *Invest. Ophthalmol. Vis. Sci.*, (2005) 46(12): 4734-4738).

Relation of Retinal Sensitivity and Vasculature

Rod photoreceptor sensitivity (SROD) at a young age (20 days) is used to predict retinal vascular outcome as specified by ICA. Better sensitivity at an early age is associated with better (less tortuous) vascular outcome (Akula et al., *Invest. Ophthalmol. Vis. Sci.*, (2007) 48: 4351-9). After cessation of the inducing oxygen exposure, recovery of post-receptor neural retinal sensitivity (b-wave log s) recovers and vascular tortuosity decreases. The regulation of developing retinal neurons and blood vessels takes place under the cooperative control of several growth factors, such as vascular endothelial growth factor (VEGF), semaphorin, and their neuropilin receptors (Gariano et al., *Gene Expression Patterns*, (2006) 6: 187-192). In rat models of ROP, expression of these growth factors has been found to be altered (Mocko et al., *ARVO Absract*, (2008)).

Described herein are also methods for treating wet aged-related macular degeneration in a patient comprising administration to the patient a therapeutically effective amount of a Visual Cycle Modulation (VCM) compound.

Visual Cycle Modulation

Figure 4A:
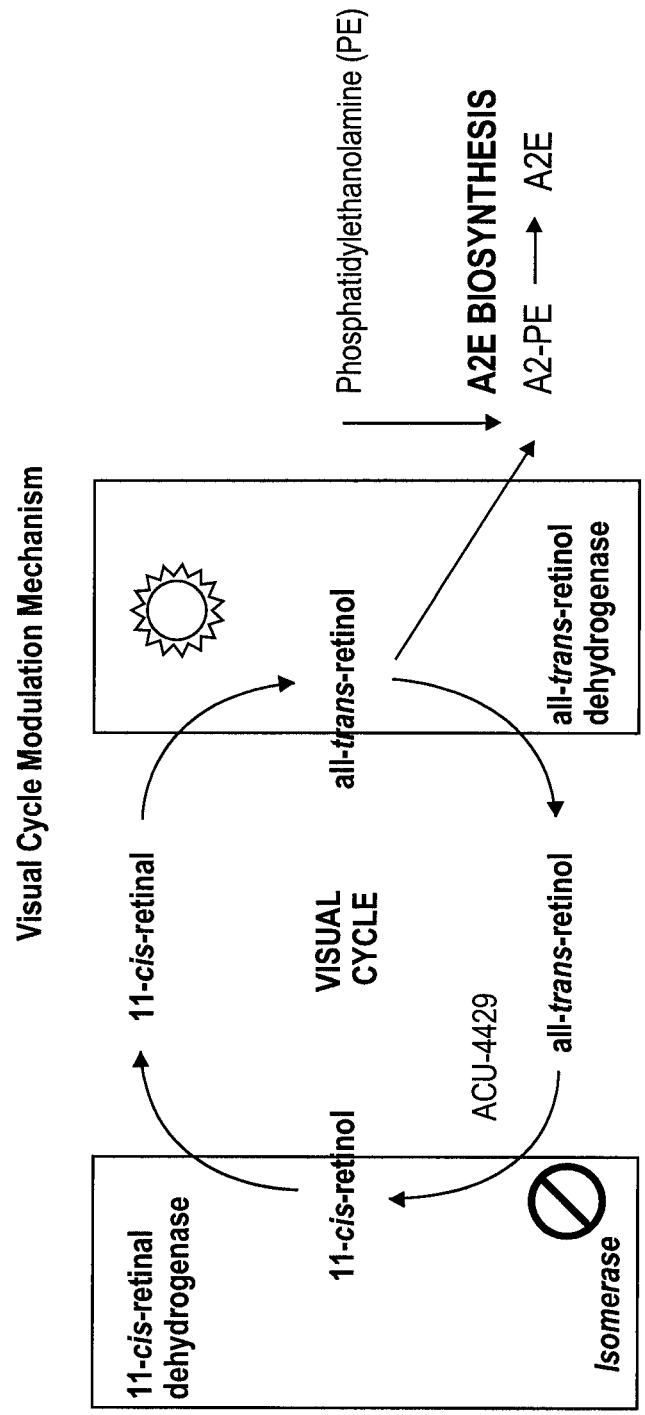
FIG. 4A depicts the Visual Cycle, which shows the biochemical conversion of visually active retinoids in the retina.
Figure 4B:
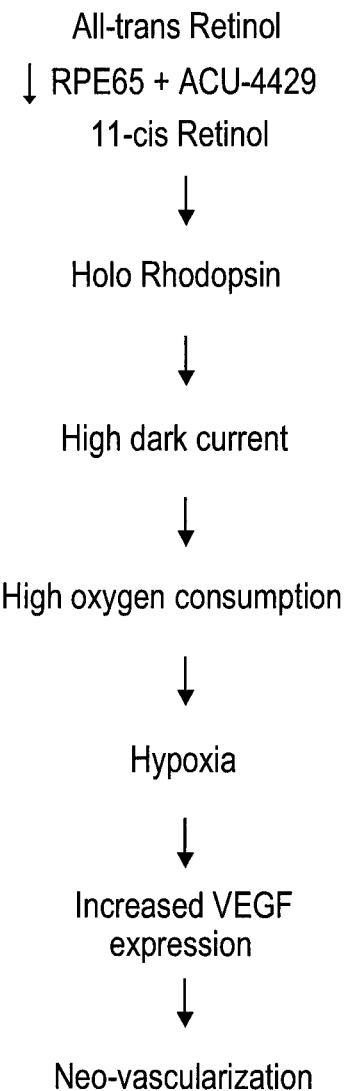
FIG. 4B illustrates a possible means of action of ACU-4429.
Figure 5:
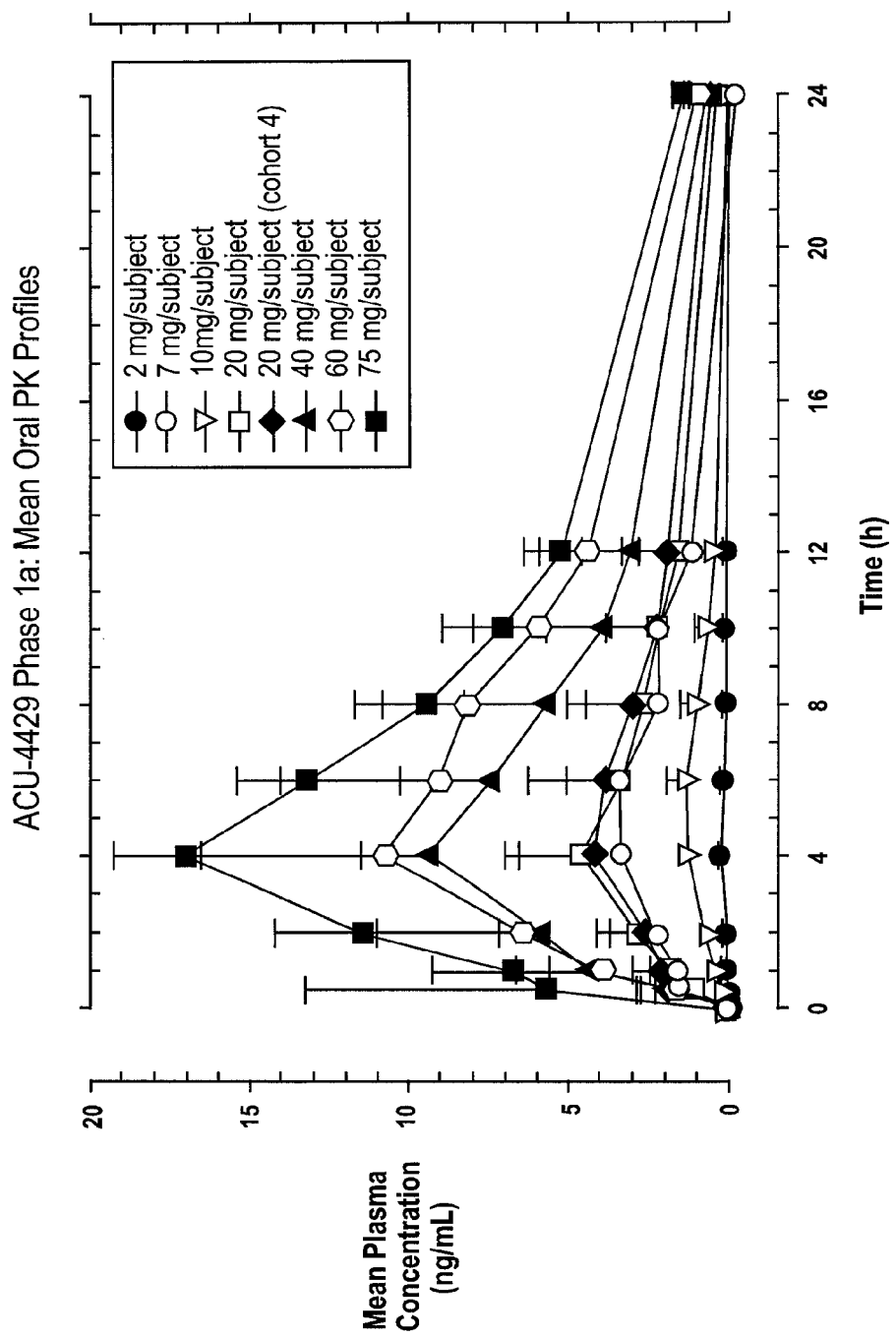
FIG. 5 is a graph depicting ACU-4429 Phase 1a data of mean oral pharmacokinetic (PK) profiles.

As used herein, "Visual Cycle Modulation" (VCM) refers to the biological conversion of a photon into electrical signal in the retina. (See, e.g., FIGS. 1A and 1B). The retina contains light-receptor cells known as "rods" (responsible for night vision) and "cones" (responsible for day vision). Rod cells are much more numerous and active than cones. Rod over-activity creates the build-up of toxins in the eye, whereas cones provide the vast majority of our visual information—including color. VCM essentially "slows down" the activity of the rods and reduces the metabolic load and oxygen consumption in the retina. FIG. 4B illustrates one means by which a VCM affects the visual cycle.

VCM compounds useful to improved outcomes in ROP are disclosed herein. VCM compounds are administered alone or with one or more additional compounds/treatments including, but not limited to, pharmaceutical treatments that reduce the energy demand of the rod photoreceptors can reduce inappropriate vascular proliferation, and environmental treatments that increase the light to which a patient is exposed. Due to the physiology of the rod photoreceptors, metabolic demand is highest in low light situations; thus, exposure to increased light can reduce metabolic demand, thereby mitigate the manifestation of ROP.

Macular Degeneration

Macular Degeneration refers to the loss of photoreceptors in the portion of the central retina, termed the macula, responsible for high-acuity vision. Degeneration of the macula is associated with abnormal deposition of extracellular matrix components and other debris in the membrane between the retinal pigment epithelium and the vascular choroid. This debris-like material is termed drusen. Drusen is observed with a funduscopic eye examination. Normal eyes may have maculas free of drusen, yet drusen may be abundant in the retinal periphery. The presence of soft drusen in the macula, in the absence of any loss of macular vision, is considered an early stage of AMD.

Age-Related Macular Degeneration

Age-related Macular Degeneration (AMD) refers to a disease that causes abnormality in the macula of the retina; it is the leading cause of vision loss in Europe and the United States. In Japan, the disease is also steadily increasing because of the aging population. The macula is located in the center of the retina, and the region is densely populated with cone cells among the photoreceptor cells. Rays of light coming from outside are refracted by the cornea and crystalline lens, and then converge on the macula, the central fovea in particular. The ability to read letters depends on the function of this area. In age-related macular degeneration, the macula, which is an important area as described above, degenerates with age and results in visual impairment, mainly in the form of image distortion (anorthopia) and central scotoma.

Central geographic atrophy, the "dry" form of advanced AMD, results from atrophy to the retinal pigment epithelial layer below the retina, which causes vision loss through loss of photoreceptors (rods and cones) in the central part of the eye. Neovascular or exudative AMD, the "wet" form of advanced AMD, causes vision loss due to abnormal blood vessel growth (choroidal neovascularization) in the choriocapillaris, through Bruch's membrane, ultimately leading to blood and protein leakage below the macula. Bleeding, leaking, and scarring from these blood vessels eventually cause irreversible damage to the photoreceptors and rapid vision loss if left untreated. The wet form of age-related macular degeneration is a disease with a poor prognosis, which results in rapid and severe visual impairment. The major pathological condition is choroidal neovascularization.

Age-related macular degeneration (AMD) is one of the leading causes of blindness in the developed world. The approval of the macromolecules LUCENTIS®, AVASTIN®, and MACUGEN® has improved the treatment options available for AMD patients. LUCENTIS® is a Fab and AVASTIN® is a monoclonal antibody. They both bind vascular endothelial growth factor (VEGF) and may be used to treat AMD; however, only a minority of treated patients experiences a significant improvement in visual acuity.

Choroidal Neovascularization

Choroidal Neovascularization (CNV) refers to the creation of new blood vessels in the choroid layer of the eye. CNV can occur rapidly in individuals with defects in Bruch's membrane, the innermost layer of the choroid. It is also associated with excessive amounts of vascular endothelial growth factor (VEGF). As well as in wet AMD, CNV can also occur frequently with the rare genetic disease pseudoxanthoma elasticum and rarely with the more common optic disc drusen. CNV has also been associated with extreme myopia or malignant myopic degeneration, where in choroidal neovascularization occurs primarily in the presence of cracks within the retinal (specifically) macular tissue known as lacquer cracks.

CNV can create a sudden deterioration of central vision, noticeable within a few weeks. Other symptoms which can occur include metamorphopsia, and color disturbances. Hemorrhaging of the new blood vessels can accelerate the onset of symptoms of CNV.

CNV can be detected by measuring the Preferential Hyperacuity Perimeter. On the basis of fluorescein angiography, CNV may be described as classic or occult. PHP is a specialized perimeter that applies principles of both static and automated perimetry to detect defects in the visual field. Rather than measuring peripheral visual fields, PHP relies on the concept of hyperacuity to measure subtle differences in the central and paracentral fields. Hyperacuity is the ability to discern a subtle misalignment of an object. Hyperacuity, or Vernier acuity, has a threshold of 3 to 6 seconds of arc in the fovea. Therefore, hyperacuity's threshold is approximately 10 fold lower than that required for optimal resolution of an object, which is 30 to 60 seconds of arc in the fovea.

Choroidal neovascularization (CNV) commonly occurs in macular degeneration in addition to other ocular disorders and is associated with proliferation of choroidal endothelial cells, overproduction of extracellular matrix, and formation of a fibrovascular subretinal membrane. Retinal pigment epithelium cell proliferation and production of angiogenic factors appears to effect choroidal neovascularization.

Current standard of care in retinology today are intravitreal injections of anti-VEGF drugs to control neovascularization and reduce the area of fluid below the retinal pigment epithelium. These drugs are commonly known as AVAS- TIN® and LUCENTIS®, and although their effectiveness has been shown to significantly improve visual prognosis with CNV, the recurrence rate for these neovascular areas remains high. Individuals with CNV should be aware that they are at a much greater risk (25%) of developing CNV in fellow eye, this according to the American Academy of Ophthalmology and further supported by clinical reports.

In "wet" (also known as "neovascular") Age-Related Macular Degeneration, CNV is treated with photodynamic therapy coupled with a photosensitive drug such as verteporfin. Verteporfin, a benzoporphyrin derivative, is an intravenous lipophilic photosensitive drug with an absorption peak of 690 nm. This drug was first approved by the Food and Drug Administration (FDA) on Apr. 12, 2000, and subsequently, approved for inclusion in the United States Pharmacopoeia on Jul. 18, 2000, meeting Medicare's definition of a drug when used in conjunction with ocular photodynamic therapy (see §80.2, "Photodynamic Therapy") when furnished intravenously incident to a physician's service. For patients with age-related macular degeneration, Verteporfin is only covered with a diagnosis of neovascular age-related macular degeneration (ICD-9-CM 362.52) with predominately classic subfoveal choroidal neovascular (CNV) lesions (where the area of classic CNV occupies >50 percent of the area of the entire lesion) at the initial visit as determined by a fluorescein angiogram (CPT code 92235). Subsequent follow-up visits will require a fluorescein angiogram prior to treatment. OPT with verteporfin is covered for the above indication and will remain non-covered for all other indications related to AMD (see §80.2). OPT with Verteporfin for use in non-AMD conditions is eligible for coverage through individual contractor discretion+. Verteporfin is given intravenously. It is then activated in the eye by a laser light. The drug destroys the new blood vessels, and prevents any new vessels forming by forming thrombi.

Anti-VEGF drugs, such as pegaptanib and ranibizumab, are also used to treat CNV. Anti-VEGFs bind to and inactivate VEGF.

CNV refers to ectopic growth of choroidal vessels, penetrating through Bruch's membrane and retinal pigment epithelia. In wet age-related macular degeneration, hemorrhage and leakage of plasma components comprising fat from the premature vascular plexus is the direct cause of the rapid functional impairment of the neural retina. CNV is thought to be induced by inflammatory cells mainly comprising macrophages that infiltrate to phagocytose drusen accumulated at the subretinal macular area. Inflammatory cells such as macrophages are also sources of production of angiogenic factors, such as vascular endothelial growth factor (VEGF), and they function to enhance neovascularization at sites of inflammation. This process is called "inflammatory neovascularization". Meanwhile, drusen comprise advanced glycation end-products (AGE) and amyloid beta, which are substances that stimulate VEGF production; these substances stimulate retinal pigment epithelia that have migrated to engulf drusen, resulting in VEGF secretion, and this is thought to be another possible mechanism by which CNV develops. Diseases involving CNV include myopic choroidal neovascularization and idiopathic choroidal neovascularization as well as age-related macular degeneration. Development of diseases involving CNV can sometimes be ascribed to angioid streaks, injury, uveitis, or such. Tissue damage mainly of the Bruch's membrane and retinal pigment epithelia in the subretinal macular area, and the subsequent inflammation, have been suggested to be involved in the mechanism of CNV onset in these diseases, as well as in age-related macular degeneration.

Medical Procedures Requiring Prolonged Eye Exposure

Most eye operations, surgeries, procedures, and examinations require the exposure of direct bright light aimed at the eye(s) and in many cases this exposure is prolonged; the compounds disclosed herein are useful for limiting or otherwise preventive unwanted damage to the eye by such exposure.

Some medical procedures are aimed at correcting structural defects of an eye.

Refractive eye surgery involves various methods of surgical remodeling of the cornea or cataract (e.g. radial keratotomy uses spoke-shaped incisions made with a diamond knife). In some instances, excimer lasers are used to reshape the curvature of the cornea. In some instances, successful refractive eye surgery reduces or cures common vision disorders such as myopia, hyperopia and astigmatism, as well as degenerative disorders like keratoconus. Other types of refractive eye surgeries include keratomilleusis (a disc of cornea is shaved off, quickly frozen, lathe-ground, then returned to its original power), automated lamellar keratoplasty (ALK), laser assisted in-situ keratomileusis (LASIK), intraLASIK, laser assisted sub-epithelial keratomileusis (LASEK aka Epi-LASIK), photorefractive keratectomy, laser thermal keratoplasty, conductive keratoplasty, limbal relaxing incisions, astigmatic keratotomy, radial keratotomy, mini asymmetric radial keratotomy, hexagonal keratotomy, epikeratophakia, intracorneal ring or ring segment implant (Intacs), contact lens implant, presbyopia reversal, anterior ciliary sclerotomy, laser reversal of presbyopia, scleral expansion bands, and Karmra inlay.

Corneal surgery includes but is not limited to corneal transplant surgery, penetrating keratoplasty, keratoprosthesis, phototherapeutic keratectomy, pterygium excision, corneal tattooing, and osteo-odonto-keratoprosthesis (OOKP). In some instances, corneal surgeries do not require a laser. In other instances, corneal surgeries use a laser (e.g., phototherapeutic keratectomy, which removes superficial corneal opacities and surface irregularities). In some instances, patients are given dark eyeglasses to protect their eyes from bright lights after these procedures.

Some procedures are aimed at removing defective components or fluids from the eye.

Cataract surgery involves surgical removal of the lens and replacement with a plastic intraocular lens. Typically, a light is used to aid the surgeon.

There are various types of glaucoma surgery that facilitate the escape of excess aqueous humor from the eye to lower intraocular pressure. In some instances, these medical procedures use a laser (e.g., laser trabeculoplasty applies a laser beam to burn areas of the trabecular meshwork, located near the base of the iris, to increase fluid outflow; laser peripheral iridotomy applies a laser beam to selectively burn a hole through the iris near its base; etc.). Canaloplasty is an advanced, nonpenetrating procedure designed to enhance drainage through the eye's natural drainage system utilizing microcatheter technology in a simple and minimally invasive procedure. Other medical procedures used for the treatment of glaucoma include lasers, non-penetrating surgery, guarded filtration surgery, and seton valve implants.

Vitreo-retinal surgery includes vitrectomy (e.g., anterior vitrectomy and pars plana vitrectomy). In some instances, vitreo-retinal surgery is used for preventing or treating vitreous loss during cataract or corneal surgery, removing misplaced vitreous tissue in conditions such as aphakia pupillary block glaucoma, removing vitreous opacities and membranes through an incision, retinal detachment repair (using ignipuncture, a scleral buckle, or laser photocoagulation, pneumatic retinopexy, retinal cryopexy, or retinal cryotherapy), macular hole repair, partial lamellar sclerouvectomy, partial lamellar sclerocyclochoroidectomy, partial lamellar sclerochoroidectomy, posterior sclerotomy, radial optic neurotomy, and macular translocation surgery. Pan retinal photocoagulation (PRP), a type of photocoagulation laser therapy often used in the treatment of diabetic retinopathy, is aimed at treating vitreous hemorrhaging, bleeding in the eye from injuries, retinal tears, subarachnoidal bleedings, or blocked blood vessels. In some instances, photocoagulation with a laser shrinks unhealthy blood vessels or seals retinal holes once blood is removed.

Some medical procedures address structures or features that support eye function or eye appearance. Eye muscle surgery typically corrects strabismus and includes the following: loosening and weakening procedures (e.g., recession, myectomy, myotomy, tenectomy, tenotomy, tightening, etc.), strengthening procedures (e.g., resection, tucking, movement of an eye muscle from its original place of attachment on the eyeball to a more forward position, etc.); transposition and repositioning procedures, and adjustable suture surgery (e.g., methods of reattaching an extraocular muscle by means of a stitch that can be shortened or lengthened within the first post-operative day, to obtain better ocular alignment).

Oculoplastic surgery, or oculoplastics, is the subspecialty of ophthalmology that deals with the reconstruction of the eye and associated structures, including eyelid surgery, repair of tear duct obstructions, orbital fracture repairs, removal of tumors in and around the eyes, and facial rejuvenation procedures including laser skin resurfacing, eye lifts, brow lifts, facelifts, Botox injections, ultrapeel microdermabrasion, and liposuction. Some eye procedures improve the lacrimal apparatus including dacryocystorhinostomy, canaliculodacryocystostomy, canaliculotomy, dacryoadenectomy, dacryocystectomy and dacryocystostomy.

Visual Cycle Modulation Compounds

As used in the specification and appended claims, unless specified to the contrary, the following terms have the meaning indicated below.

As used herein and in the appended claims, the singular forms "a," "and," and "the" include plural references unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. Also, for example, references to "the method" includes one or more methods, and/or steps of the type described herein and/or which will become apparent to those persons skilled in the art upon reading this disclosure and so forth. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t$$R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t$$R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-SR^a$, $-R^b-OC(O)-R^a$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula $-R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-SR^a$, $-R^b-OC(O)-R^a$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included.

A "stereoisomer" refers to a compound made up of the same atoms bonded by the same bonds but having different three-dimensional structures, which are not interchangeable. It is therefore contemplated that various stereoisomers and mixtures thereof and includes "enantiomers," which refers to two stereoisomers whose molecules are nonsuperimposeable mirror images of one another.

The compounds presented herein may exist as tautomers. A "tautomer" refers to a proton shift from one atom of a molecule to another atom of the same molecule, accompanied by an isomerization of an adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

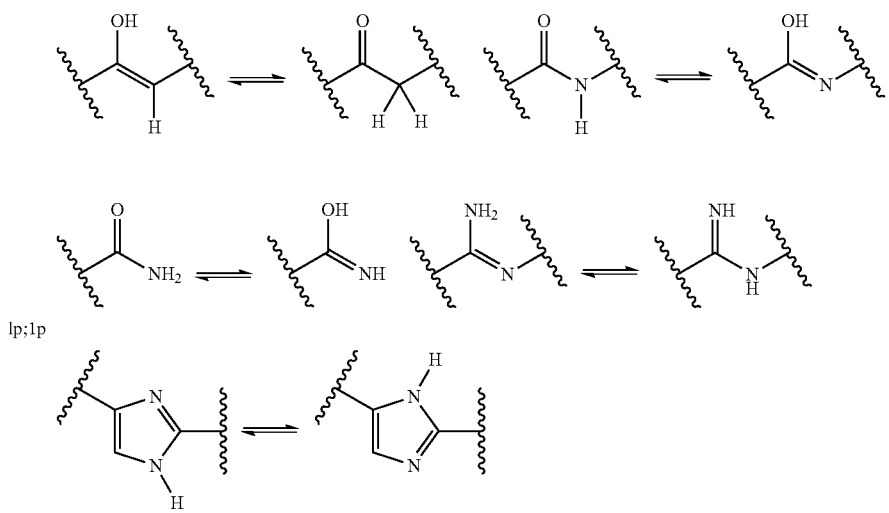

lp;1p

-continued

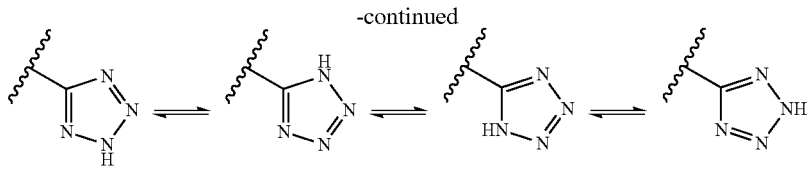

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted heterocyclic amine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfates, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Compositions and Modes of Administration

In some embodiments, the compounds described herein are formulated as a pharmaceutically acceptable composition when combined with an acceptable carrier or excipient.

Thus, in some embodiments, compositions include, in addition to active ingredient, an acceptable excipient, carrier, buffer, stabilizer or other materials known in the art for use within a composition to be administered to a patient. Such materials are non-toxic and do not interfere with the efficacy of the active ingredient. The precise nature of the carrier or other material depends on the route of administration.

Acceptable carriers and their formulations are and generally described in, for example, Remington' pharmaceutical Sciences (18th Edition, ed. A. Gennaro, Mack Publishing Co., Easton, Pa. 1990).

Compositions are formulated to be compatible with a particular route of administration in mind Thus, compositions include carriers, diluents, or excipients suitable for administration by various routes.

A "therapeutically effective amount" of a composition to be administered is the minimum amount necessary to prevent, ameliorate, or treat a disease or disorder. The composition is optionally formulated with one or more agents currently used to prevent or treat the disorder in question. The effective amount of such other agents depends on the amount of compound present in the formulation, the type of disorder or treatment, and other factors discussed above. These are generally used in the same dosages and with administration routes as used hereinbefore or about from 1 to 99% of the heretofore employed dosages. Generally, alleviation or treatment of a disease or disorder involves the lessening of one or more symptoms or medical problems associated with the disease or disorder.

Compounds described herein are administered in any way suitable to effectively achieve a desired therapeutic effect in the eye. Thus, methods of administration include without limitation, topical, intraocular (including intravitreal), transdermal, oral, intravenous, subconjunctival, subretinal, or peritoneal routes of administration.

Administration techniques that can be employed with the compounds and methods are known in the art and described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In certain embodiments, the compounds and compositions described herein are administered orally.

Liquid formulation dosage forms for oral administration may be aqueous suspensions such as, for example, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the compound, a liquid dosage form optionally includes a pharmaceutically acceptable carrier or excipient suitable for oral administration, and, optionally, one or more additives, such as: (a) disintegrating agents; (b) dispersing agents; (c) wetting agents; (d) preservatives, (e) viscosity enhancing agents, (f) sweetening agents, and/or (g) flavoring agents. In some embodiments, the aqueous dispersions further include a crystal-forming inhibitor.

In one embodiment, emulsifying and/or suspending agents, together with diluents such as water, ethanol, propylene glycol, glycerin and various combinations thereof, may be added to the compositions.

Water may be added (e.g., 5%) as a means of simulating long-term storage in order to determine characteristics such as shelf-life or the stability of formulations over time. Anhydrous compositions and dosage forms may be prepared using anhydrous or low moisture containing ingredients and low moisture or low humidity conditions. Compositions and dosage forms which contain lactose can be made anhydrous if substantial contact with moisture and/or humidity during manufacturing, packaging, and/or storage is expected. An anhydrous composition may be prepared and stored such that its anhydrous nature is maintained. Accordingly, anhydrous compositions may be packaged using materials known to prevent exposure to water such that they can be included in suitable formulary kits.

In additional or alternative embodiments, the composition may be in the form of a tablet, capsule, pill, powder, sustained release formulation, solution, suspension, or emulsion.

Solid dosage forms for oral administration include, for example but not limited to capsules, tablets, pills, powders and granules.

In such solid dosage forms, the compositions as disclosed herein may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The active components can also be in micro-encapsulated form, if appropriate, with one or more of the above-mentioned excipients. In the preparation of pharmaceutical formulations as disclosed herein in the form of dosage units for oral administration the compound selected can be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

The composition may be in unit dosage forms suitable for single administration of precise dosages. In further or additional embodiments the amount of compound is in the range of about 0.001 to about 1000 mg/kg body weight/day. In further or additional embodiments the amount of compound is in the range of about 0.5 to about 50 mg/kg/day. In further or additional embodiments the amount of compound is about 0.001 to about 7 g/day. In further or additional embodiments the amount of compound is about 0.002 to about 6 g/day. In further or additional embodiments the amount of compound is about 0.005 to about 5 g/day. In further or additional embodiments the amount of compound is about 0.01 to about 5 g/day. In further or additional embodiments the amount of compound is about 0.02 to about 5 g/day. In further or additional embodiments the amount of compound is about 0.05 to about 2.5 g/day. In further or additional embodiments the amount of compound is about 0.1 to about 1 g/day. In some embodiments, dosage levels below the lower limit of the aforesaid range may be more than adequate. In other embodiments, dosage levels above the upper limit of the aforesaid range may be required.

In one aspect the daily dose of (R)-3-amino-1-(3-(cyclohexylmethoxy)phenyl)propan-1-ol is about 4 mg to about 100 mg. In another aspect the daily dose of (R)-3-amino-1-(3-(cyclohexylmethoxy)phenyl)propan-1-ol is about 2 mg; about 5 mg; about 7 mg; about 10 mg; about 15 mg; about 20 mg; about 40 mg; about 60 mg; about 75 mg; or about 100 mg.

In some embodiments, a composition for oral delivery contains at least about 1, 5, 10, 20, 30, 40, 50, 60, 70, 80, 90, 95, 99, 99.5, 99.9, or 99.99% of a compound described herein. In other embodiments, a composition for the oral delivery contains no more than about 2, 5, 10, 20, 30, 40, 50, 60, 70, 80, 90, 95, 99, 99.5, or 100% of a compound described herein. In some embodiments, a composition contains about 1-100%, about 10-100%, about 20-100%, about 50-100%, about 80-100%, about 90-100%, about 95-100%, or about 99-100% of a compound described herein. In some embodiments, a composition contains about 1-90%, about 10-90%, about 20-90%, about 50-90%, or about 80-90% of a compound described herein. In some embodiments, a composition contains about 1-75%, about 10-75%, about 20-75%, or about 50-75% of a compound described herein. In some embodiments, a composition contains about 1-50%, about 10-50%, about 20-50%, about 30-50%, or about 40-50% of a compound described herein. In some embodiments, a composition contains about 1-40%, about 10-40%, about 20-40%, or about 30-40% of a compound described herein. In some embodiments, a composition contains about 1-30%, about 10-30%, or about 20-30% of a compound described herein. In some embodiments, a composition contains about 1-20%, or about 10-20% of a compound described herein. In some embodiments, a composition contains about 1-10% of a compound described herein.

Methods of Treatment

Provided herein is a method for treating diabetic retinopathy in a patient (alleviating one or more symptoms, or stasis of one or more symptoms) by administering to the patient a therapeutically effective amount of a composition provided herein. The treatment can result in improving the patient's condition and can be assess by determining if one or more of the following factors has occurred: decreased macular edema, or increased visual acuity. The compounds described herein can also be used in medicaments for the treatment of diabetic retinopathy.

A "patient" is a mammal who exhibits one or more clinical manifestations and/or symptoms of a disease or disorder described herein. Non-limiting examples of patients include, but are not limited to, a human or a non-human animal such as a primate, rodent, cow, horse, pig, sheep, etc. In certain situations, the patient may be asymptomatic and yet still have clinical manifestations of the disease or disorder. In one embodiment, a patient to be treated is a human.

The compositions provided herein can be administered once or multiple times depending on the health of the patient, the progression of the disease or condition, and the efficacy of the treatment. Adjustments to therapy and treatments can be made throughout the course of treatment.

Signs and symptoms of diabetic retinopathy include, but are not limited to, one or more of the following: changes in the blood vessels; retinal swelling (macular edema); pale deposits on the retina; damaged nerve tissue; visual appearance of leaking blood vessels; loss of central or peripheral vision; temporary or permanent vision loss; spotty, blurry, hazy or double vision; eye pain; floaters; impaired color vision; vision loss; a dark or blind spot in the central vision; venous dilation and intraretinal micro vascular abnormalities; neuropathy; fluctuating and progressive deterioration of vision; macular edema; macular ischemia; traction retinal detachment; endothelial cell proliferation; photopsias; rubeosis or nvi; micro aneurysms; hard exudates; haemorrhages; and cotton wool spots; are the symptoms for diabetic retinopathy.

In one embodiment, treatment of DR with a compound described herein blocks formation of abnormal blood vessels, slows leakage from blood vessels, reduces retinal swelling, prevents retinal detachment, prevents or slows blindness, and/or reduces vision loss.

The compound to be administered in such methods is administered by any suitable means such as those described herein and known in the art.

For the prevention or treatment of disease, the appropriate dosage of compound will depend, in part, on the patient to be treated, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments.

The compositions can be administered in a manner compatible with the dosage formulation, and in a therapeutically effective amount. The quantity to be administered depends on the subject to be treated, capacity of the patient's immune system to utilize the active ingredient. Precise amounts of active ingredient required to be administered depend on the judgment of the practitioner and are peculiar to each individual. Suitable regimes for initial administration and booster shots are also variable. Depending on the type and severity of the disease, about 0.1 µg/kg to about 150 mg/kg of compound is an initial candidate dosage for administration to the patient, whether, for example, by one or more separate administrations, or by continuous infusion. Other initial dosages include, but are not limited to, about 0.25 µg/kg, about 0.5 µg/kg, about 1 µg/kg, about 10 µg/kg, about 50 µg/kg, about 100 µg/kg, about 250 µg/kg, about 500 µg/kg, about 750 µg/kg, about 1 mg/kg, about 5 mg/kg, about 10 mg/kg, about 15 mg/kg, about 20 mg/kg, about 25 mg/kg, about 50 mg/kg, about 75 mg/kg, about 100 mg/kg, about 125 mg/kg, about 150 mg/kg or more. Thereafter, a typical daily dosage may range from about 0.1 µg/kg to about 150 mg/kg or more, depending on the factors mentioned above. For repeated administrations over several days or longer, depending on the condition, the treatment is sustained until a desired suppression of disease symptoms occurs. However, other dosage regimens may be useful. Dosages may be given once daily, every over day, every week, every month, or every other month. Additionally, the dose(s) of a compound can be administered twice a week, weekly, every two weeks, every three weeks, every 4 weeks, every 6 weeks, every 8 weeks, every 12 weeks, or any combination of weeks therein. Dosing cycles are also contemplated such as, for example, administering compounds once or twice a week for 4 weeks, followed by two weeks without therapy. Additional dosing cycles including, for example, different combinations of the doses and weekly cycles described herein are also contemplated. One or more symptoms may be assessed during treatment and dosages adjusted accordingly. Dosages may be administered orally and/or intravitreally.

A composition can be administered alone or in combination with a second treatment either simultaneously or sequentially dependent upon the condition to be treated. When two or more compositions, or a composition and a treatment, are administered, the compositions or composition/treatment can be administered in combination (either sequentially or simultaneously). A composition can be administered in a single dose or multiple doses.

The term "unit dose" when used in reference to a composition refers to physically discrete units suitable as unitary dosage for humans, each unit containing a predetermined quantity of active material calculated to produce the desired therapeutic effect in association with the required diluent; i.e., carrier, or vehicle.

Depending on the type and severity of the disease, about 0.1 µg/kg to about 150 mg/kg of compound is an initial candidate dosage for administration to the patient, whether, for example, by one or more separate administrations, or by continuous infusion. Other initial dosages include, but are not limited to, about 0.25 µg/kg, about 0.5 µg/kg, about 1 µg/kg, about 10 µg/kg, about 50 µg/kg, about 100 µg/kg, about 250 µg/kg, about 500 µg/kg, about 750 µg/kg, about 1 mg/kg, about 5 mg/kg, about 10 mg/kg, about 15 mg/kg, about 20 mg/kg, about 25 mg/kg, about 50 mg/kg, about 75 mg/kg, about 100 mg/kg, about 125 mg/kg, about 150 mg/kg or more. Thereafter, a typical daily dosage may range from about 0.1 µg/kg to about 150 mg/kg or more, depending on the factors mentioned above. For repeated administrations over several days or longer, depending on the condition, the treatment is sustained until a desired suppression of disease symptoms occurs. However, other dosage regimens may be useful.

In one embodiment, treatment of a patient having age-related macular degeneration, choroidal neovascularization and/or diabetic retinopathy as described herein includes improvement of at least one of the symptoms described herein. Improvement includes, for example, a 2%, 5%, 10%, 15%, 20%, 25%, 30%, 35%, 40%, 45%, 50%, 55%, 60%, 65%, 70%, 75%, 80%, 85%, 90%, 95%, or 100% improvement in one or more signs or symptoms described herein. Compositions can be administered to a patient in a therapeutically effective amount which is effective for producing some desired therapeutic effect, at a reasonable benefit/risk ratio applicable to any medical treatment. For the administration of the present compositions to human patients, the compositions can be formulated by methodology known by one of ordinary skill in the art.

As used herein, the term "treatment" refers to both therapeutic treatment and prophylactic measures. Those in need of treatment include those already with the disorder as well as those in which the disorder is to be prevented from worsening. In one embodiment, treatment of a patient having diabetic retinopathy as described herein means that one or more signs or symptoms does not worsen or progress. In another embodiment, treatment of a patient having age-related macular degeneration and/or choroidal neovascularization as described herein means that one or more signs or symptoms does not worsen or progress. As used herein, "prevention" refers to prophylaxis, prevention of onset of symptoms, prevention of progression of one or more signs or symptoms of diabetic retinopathy, age-related macular degeneration and/or choroidal neovascularization. As used herein, "inhibition," "treatment" and "treating" are used to refer to, for example, stasis of symptoms, prolongation of survival, partial or full amelioration of symptoms.

"Administering" is defined herein as a means providing the composition to the patient in a manner that results in the composition being inside the patient's body. Such an administration can be by any route including, without limitation, modes of administration described herein or conventionally known in the art. "Concurrent administration" means administration within a relatively short time period from each other; such time period can be less than 2 weeks, less than 7 days, less than 1 day and could even be administered simultaneously.

Actual dosage levels of the active ingredients in the compositions can be varied so as to obtain an amount of the active ingredient that is effective to achieve the desired therapeutic response for a particular patient, composition, and mode of administration, without being toxic to the patient. The selected dosage level will depend upon a variety of factors including the activity of the particular compound employed, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts.

In one embodiment, the compound may be administered in a single dose, once daily. In other embodiments, the compound may be administered in multiple doses, more than once per day. In other embodiments, the compound may be administered twice daily. In other embodiments, the compound may be administered three times per day. In other embodiments, the compound may be administered four times per day. In other embodiments, the compound may be administered more than four times per day.

A response is achieved when the patient experiences partial or total alleviation, or reduction of signs or symptoms of illness, and specifically includes, without limitation, prolongation of survival. The expected progression-free survival times can be measured in months to years, depending on prognostic factors including the number of relapses, stage of disease, and other factors. Prolonging survival includes without limitation times of at least 1 month (mo), about at least 2 months (mos.), about at least 3 mos., about at least 4 mos., about at least 6 mos., about at least 1 year, about at least 2 years, about at least 3 years, or more. Overall survival can also be measured in months to years. The patient's symptoms can remain static or can decrease.

A physician or veterinarian having ordinary skill in the art can readily determine and prescribe the effective amount ($ED_{50}$) of the composition required. For example, the physician or veterinarian could start doses of the compounds employed in the composition at levels lower than that required in order to achieve the desired therapeutic effect and gradually increase the dosage until the desired effect is achieved. Alternatively, a dose can remain constant.

Toxicity and therapeutic efficacy of such ingredient can be determined by standard pharmaceutical procedures in cell cultures or experimental animals, e.g., for determining the LD$_{50}$ (the dose lethal to 50% of the population) and the ED$_{50}$ (the dose therapeutically effective in 50% of the population). The dose ratio between toxic and therapeutic effects is the therapeutic index and it can be expressed as the ratio LD$_{50}$/ED$_{50}$. While compounds that exhibit toxic side effects may be used, care should be taken to design a delivery system that targets such compounds to the site of affected tissue in order to minimize potential damage to healthy cells and, thereby, reduce side effects.

Also provided herein are methods of treating retinopathy of prematurity (ROP) in a patient in need thereof by administering a composition containing a compound described herein.

Provided herein is a method of treating or preventing retinopathy of prematurity, comprising administering to a patient in need thereof a composition comprising a visual cycle modulator (VCM) compound such as those described herein.

In one embodiment, the compound alters the visual cycle. Patients to be treated with such methods are premature infants.

In another embodiment, the patient is additionally treated with supplemental oxygen.

In another embodiment, the treatment is administered locally to the eye or systemically.

Provided herein is the use of a visual cycle modulator as described herein in the formulation of a medicament for the treatment of retinopathy of prematurity. Treatments described herein can be administered and monitored by a medical practitioner. Administration routes, dosages and specific measures of efficacy can be selected by the administering practitioner, and may depend upon factors such as the severity of disease, age, weight and gender of the patient, as well as other factors, such as other medical problems of the patient.

Efficacy for any given composition may also be determined using an experimental animal model, e.g., the rat model of ROP described herein. When using an experimental animal model, efficacy of treatment may be assessed when a reduction in a marker or symptom of ROP is observed.

The amount and frequency of administration will also depend, in part, on the composition itself, its stability and specific activity, as well as the route of administration. Greater amounts of a composition will generally have to be administered for systemic, compared to topically/locally administered compositions.

The eye provides a tissue or structure well suited for topical administration of many drugs. Intraocular injection and oral administration can also be effective. Doses will may depending on route of administration, and will vary from, e.g., about 0.1 mg/kg body weight to about 10 mg/kg body weight for by systemic administration, to 0.01 mg to 10 mg by topical or intraocular injection routes. Other dosages are also contemplated herein.

A "therapeutically effective amount" of a composition to be administered will be governed by such considerations, and is the minimum amount necessary to prevent, ameliorate, or treat a disease or disorder. The composition need not be, but may be optionally formulated with one or more agents currently used to prevent or treat the disorder in question. The effective amount of such other agents depends on the amount of compound present in the formulation, the type of disorder or treatment, and other factors discussed above. These are generally used in the same dosages and with administration routes as used hereinbefore or about from 1 to 99% of the heretofore employed dosages. Generally, alleviation or treatment of a disease or disorder involves the lessening of one or more symptoms or medical problems associated with the disease or disorder.

In general, an compound is determined to be "therapeutically effective" in the methods described herein if (a) measurable symptom(s) of, for example, vascular abnormalities, are reduced for example by at least 10% compared to the measurement prior to treatment onset, (b) the progression of the disease is halted (e.g., patients do not worsen or the vasculature stops growing pathologically, or (c) symptoms are reduced or even ameliorated, for example, by measuring a reduction in vessel number or tortuosity. Efficacy of treatment can be judged by an ordinarily practitioner or as described herein and known in the art.

The compositions as disclosed herein can also be administered in prophylactically or therapeutically effective amounts. A prophylactically or therapeutically effective amount means that amount necessary, at least partly, to attain the desired effect, or to delay the onset of, inhibit the progression of, or halt altogether, the onset or progression of the particular disease or disorder being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art, however, that a lower dose or tolerable dose can be administered for medical reasons, psychological reasons or for virtually any other reasons.

As used herein, "improving rod-mediated retinal function" refers to an increase in rod-mediated retinal function of at least 10%, at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 50-fold, at least 100-fold, at least 1000-fold or higher.

"Rod-mediated retinal function" refers to a function of rod cells in a functioning retina and can include such clinical end-points as degree of peripheral vision, low-level light vision, scotopic/"night vision", and sensitivity to peripheral movement. Rod-mediated retinal function can be assessed in vivo by, for example, electroretinography measurement of rod activation of photo-transduction or deactivation of photo-transduction; recovery of the dark current following photobleaching; measurement of the ERG a-wave or b-wave; speed of recovery to photo-transduction; or rod-mediated response amplitudes. Methods for measuring rod-mediated retinal function are known in the art and/or explained herein in more detail.

Efficacy of treatment can be monitored by the administering clinician. Where the disease or disorder is retinopathy of prematurity, the International Classification of Retinopathy or Prematurity (ICROP) can be applied. The ICROP uses a range of parameters to classify the disease. These parameters include location of the disease into zones (zones 1, 2 and 3), the circumferential extent of the disease based on clock hours 1-12, severity of the disease (stages 1-5), and the presence or absence of "Plus Disease."

The zones are centered on the optic nerve. Zone 1 is the posterior zone of the retina, defined as the circle with a radius extending from the optic nerve to double the distance to the macula. Zone 2 is an annulus with the inner border defined by zone 1 and the outer border defined by the radius defined as the distance from the optic nerve to the nasal ora serrata. Zone 3 is the residual temporal crescent of the retina.

The circumferential extent of the disease is described in segments as if the top of the eye were 12 on the face of a clock. For example one might report that there is stage 1 disease for 3 clock hours from 4 to 7 o'clock.

The Stages describe the ophthalmoscopic findings at the junction between the vascularized and avascular retina. Stage 1 is a faint demarcation line. Stage 2 is an elevated ridge. Stage 3 is extraretinal fibrovascular tissue. Stage 4 is sub-total retinal detachment. Stage 5 is total retinal detachment.

In addition, "Plus disease" may be present at any stage. "Plus disease" describes a significant level of vascular dilation and tortuosity observed at the posterior retinal vessels. This reflects the increase of blood flow through the retina.

Any improvement on the ICROP relative to pre-treatment classification is considered to be effective treatment. Similarly, where prevention of disease is the goal, treatment is considered effective if one or more signs or symptoms of ROP is(are) less severe in a treated individual relative to the expected course of disease in a similar individual not receiving such treatment. The disease has been known and characterized to an extent that skilled clinicians can often predict the extent of disease that would occur in the absence of treatment, based, for example, on knowledge of earlier patients. The failure to develop or experience a worsening of one or more symptoms of ROP, or, for that matter any other retinal disease or disorder involving abnormal vascularization, can be considered effective prevention of disease in an individual otherwise expected to develop or experience worsening of such disease. Similarly, any improvement relative to expected disease state in the absence of treatment can be considered effective treatment.

As an alternative to the ICROP scale, other clinically accepted markers of retinal disease known to those of skill in the art can also be measured to monitor or determine the efficacy of treatment or prevention of retinal diseases or disorders as described herein. Generally a difference of at least 10% in a marker of retinal disease is considered significant.

Provided herein are methods for reducing or inhibiting vascularization in the eye (e.g., neovascularization) of a patient. Also provided herein is a method for treating an ophthalmic disease or disorder associated with neovascularization in the eye of a patient wherein the ophthalmic disease or disorder associated with neovascularization is retinal neovascularization. Another embodiment provides a method for treating an ophthalmic disease or disorder associated with neovascularization in the eye of a patient wherein the ophthalmic disease or disorder associated with neovascularization is choroidal neovascularization. Another embodiment provides a method for treating an ophthalmic disease or disorder associated with neovascularization in the eye of a patient wherein the ophthalmic disease or disorder associated with neovascularization is selected from sickle cell retinopathy, Eales disease, ocular ischemic syndrome, carotid cavernous fistula, familial exudative vitreoretinopathy, hyperviscosity syndrome, idiopathic occlusive arteriolitis, radiation retinopathy, retinal vein occlusion, retinal artery occlusion, retinal embolism, birdshot retinochoroidopathy, retinal vasculitis, sarcoidosis, toxoplasmosis, uveitis, choroidal melanoma, chronic retinal detachment, incontinentia pigmenti, and retinitis pigmentosa. Another embodiment provides a method for treating an ophthalmic disease or disorder associated with neovascularization in the eye of a patient wherein the ophthalmic disease or disorder associated with neovascularization is wet age-related macular degeneration. Another embodiment provides a method for treating an ophthalmic disease or disorder associated with neovascularization in the eye of a patient wherein the ophthalmic disease or disorder associated with neovascularization is neovascular age-related macular degeneration.

Provided herein is a method for treating neovascular age-related macular degeneration (e.g., wet age-related macular degeneration (AMD)) or choroidal neovascularization (CNV) in a patient by administering to the patient a therapeutically effective amount of a composition provided herein. The compounds described herein can also be used in medicaments for the treatment of macular degeneration (e.g., age-related macular degeneration (AMD)) or choroidal neovascularization (CNV). As provided herein all references to age-related macular degeneration refer to the neovascular or wet stage of the disease.

Provided herein is a method for treating age-related macular degeneration (AMD) in a patient by administering to the patient a therapeutically effective amount of a composition provided herein. The treatment can result in improving the patient's condition and can be assess by determining if one or more of the following factors has occurred: Drusen; pigmentary alterations; eudative changes (e.g., hemorrhages in the eye, hard exudates, subretinal/sub-RPE/intraretinal fluid); atrophy (incipient and geographic); visual acuity drastically decreasing (two levels or more; ex: 20/20 to 20/80); preferential hyperacuity perimetry changes (for wet AMD); blurred vision (those with non-exudative macular degeneration may be asymptomatic or notice a gradual loss of central vision, whereas those with exudative macular degeneration often notice a rapid onset of vision loss); central scotomas (shadows or missing areas of vision); distorted vision (i.e., metamorphopsia; a grid of straight lines appears wavy and parts of the grid may appear blank. Patients often first notice this when looking at mini-blinds in their home); trouble discerning colors (specifically dark ones from dark ones and light ones from light ones); slow recovery of visual function after exposure to bright light; and a loss in contrast sensitivity. Described herein are methods of treating or preventing AMD via the administration of the compounds described herein. The compounds described herein can also be used in medicaments for the treatment of AMD. In one embodiment, one or more signs or symptoms of AMD are improved following administration of one of the compounds described herein to a patient. Improvement also encompasses stasis of one or more symptoms such that they do not worsen.

"Treatment" of diseases involving CNV refers to diseases involving CNV, where a symptom caused by an above disease is suppressed or ameliorated. The treatment of diseases involving CNV also refers to suppressing CNV progression and functional impairment of neural retina caused by hemorrhage or leakage of plasma components from abnormal newly generated vessels.

As used herein, "suppressing CNV" refers to suppressing inflammation in the retina (suppressing the growth of inflammatory cells in the retina) and suppressing the production of angiogenic factors by inflammatory cells, in addition to suppressing neovascularization. An inflammation reaction in the retina may be induced by an injury, or by accumulation of metabolic decomposition products, such as drusen.

CNV can be confirmed to be suppressed by detecting the size (volume) of neovascularization using fluorescein fundus angiography or the like. When the volume of neovascularization is reduced after administration of an agent of the present disclosure, CNV is regarded as suppressed. Methods for detecting CNV are not limited to the methods described above, and CNV can be detected by known methods, and also by the methods described in the Examples herein.

As a disease involving CNV progresses, vision is impaired due to image distortion, central scotoma, and such. In such cases of visual impairment, when visual acuity is improved upon administration of a compound described herein, the compound is regarded as useful for patients with such a disease involving CNV. Provided herein is a method for treating choroidal neovascularization The treatment can result in improving the patient's condition and can be assess by determining if visual acuity has increased. Described herein are methods of treating or preventing choroidal neovascularization via the administration of the compounds described herein.

Choroidal neovascularization (CNV) commonly occurs in macular degeneration in addition to other ocular disorders and is associated with proliferation of choroidal endothelial cells, overproduction of extracellular matrix, and formation of a fibrovascular subretinal membrane. Retinal pigment epithelium cell proliferation and production of angiogenic factors appears to effect choroidal neovascularization. Choroidal neovascularization (CNV), the development of abnormal blood vessels beneath the retinal pigment epithelium (RPE) layer of the retina. These vessels break through the Bruch's membrane, disrupting the retinal pigmented epithelium, bleed, and eventually cause macular scarring which results in profound loss of central vision (disciform scarring).

In one embodiment, treatment of CNV with a compound described herein decreases slows or inhibits development of abnormal blood vessels beneath the retinal pigment epithelium layer of the retina, slows or inhibits damage of the Bruch's membrane, and slows or inhibits disruption of the retinal pigmented epithelium and slows or inhibits macular scarring.

Retinal neovascularization develops in numerous retinopathies associated with retinal ischemia, such as sickle cell retinopathy, Eales disease, ocular ischemic syndrome, carotid cavernous fistula, familial exudative vitreoretinopathy, a hyperviscosity syndrome, idiopathic occlusive arteriolitis, radiation retinopathy, retinal vein occlusion, retinal artery occlusion, or retinal embolism. Retinal neovascularization can also occur with inflammatory diseases (such as birdshot retinochoroidopathy, retinal vasculitis, sarcoidosis, toxoplasmosis, or uveitis), or other conditions such as choroidal melanoma, chronic retinal detachment, incontinentia pigmenti, and rarely in retinitis pigmentosa.

A factor common to almost all retinal neovascularization is retinal ischemia, which is thought to release diffusible angiogenic factors (such as VEGF). The neovascularization begins within the retina and then breaches the retinal internal limiting membrane. The new vessels grow on the inner retina and the posterior surface of the vitreous after it has detached (vitreous detachment). Neovascularization may erupt from the surface of the optic disk or the retina. Retinal neovascularization commonly progresses to vitreoretinal neovascularization. Iris neovascularization and neovascular glaucoma often follow retinal neovascularization.

The efficacy of the treatment of the measured by various endpoints commonly used in evaluating intraocular neovascular diseases. For example, vision loss can be assessed. Vision loss can be evaluated by, but not limited to, e.g., measuring by the mean change in best correction visual acuity (BCVA) from baseline to a desired time point (e.g., where the BCVA is based on Early Treatment Diabetic Retinopathy Study (ETDRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired time point compared to baseline, measuring the proportion of subjects with a visual-acuity Snellen equivalent of 20/2000 or worse at a desired time point, measuring the NEI Visual Functioning Questionnaire, measuring the size of CNV and amount of leakage of CNV at a desired time point, e.g., by fluorescein angiography, etc. Ocular assessments can be done, e.g., which include, but are not limited to, e.g., performing eye exam, measuring intraocular pressure, assessing visual acuity, measuring slitlamp pressure, assessing intraocular inflammation, etc.

Provided herein is a method for protecting an eye during medical procedures requiring exposure of the eye to bright light, to laser light, resulting in prolonged and/or excessive dilation of the pupil, or otherwise sensitizing the eye to light, the method comprising administration of a composition comprising a compound described herein to a patient in need thereof.

In one embodiment, the medical procedure is refractive eye surgery, corneal surgery, cataract surgery, glaucoma surgery, canaloplasty, vitreo-retinal surgery, pan retinal photocoagulation, eye muscle surgery, oculoplastic surgery, laser therapy, or focal or grid laser photocoagulation. In one embodiment, the medical procedure is refractive eye surgery. In one embodiment, the medical procedure is corneal surgery. In one embodiment, the medical procedure is cataract surgery. In one embodiment, the medical procedure is glaucoma surgery. In one embodiment, the medical procedure is canaloplasty. In one embodiment, the medical procedure is vitreo-retinal surgery. In one embodiment, the medical procedure pan retinal photocoagulation. In one embodiment, the medical procedure is eye muscle surgery. In one embodiment, the medical procedure is oculoplastic surgery. In one embodiment, the medical procedure is laser therapy. In one embodiment, the medical procedure is focal or grid laser photocoagulation.

In one embodiment, the composition is administered to the patient orally before and after the medical procedure.

In one embodiment, the composition is administered orally prior to the medical procedure. In one embodiment, the composition is administered about 0.5 h, 1 h, 1.5 h, 2 h, 2.5 h, 3 h, 3.5 h, 4 h, 6 h, 12 h, or 24 h prior to the procedure.

In one embodiment, the composition is administered after the medical procedure. In one embodiment, the composition is administered 1 h, 3 h, 6 h, 12 h, 24 h, or 48 h after the medical procedure. In one embodiment, the composition is administered 24 h after the medical procedure. In one embodiment, the composition is administered 48 h after the medical procedure. In one embodiment, the composition is administered 24 h and 48 h after the medical procedure.

In one embodiment, the composition is administered as a single dose of compound. In one embodiment, the composition comprises about 2 mg, 5 mg, 10 mg, 15 mg, 20 mg, 25 mg, 30 mg, 35 mg, 40 mg, 45 mg, 50 mg, 60 mg, 70 mg, 80 mg, 90 mg, or about 100 mg.

The compound to be administered in such methods is administered by any suitable means such as those described herein and known in the art.

For the prevention or treatment of disease, the appropriate dosage of compound will depend, in part, on the patient to be treated, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments.

The compositions can be administered in a manner compatible with the dosage formulation, and in a therapeutically effective amount. The quantity to be administered depends on the subject to be treated, capacity of the patient's immune system to utilize the active ingredient. Precise amounts of active ingredient required to be administered depend on the judgment of the practitioner and are peculiar to each individual. Suitable regimes for initial administration and booster shots are also variable.

A composition can be administered alone or in combination with a second treatment either simultaneously or sequentially dependent upon the condition to be treated. When two or more compositions, or a composition and a treatment, are administered, the compositions or composition/treatment can be administered in combination (either sequentially or simultaneously). A composition can be administered in a single dose or multiple doses.

Compounds described herein can be, as needed, administered in combination with one or more standard therapeutic treatments known in the art and as described, for example, in more detail below.

Combination Therapy

Diabetic retinopathy is a consequence of the underlying diabetic condition and additional means to lower the risk of developing it or to slow its progression is to: maintain optimal blood sugar levels; have regular, thorough eye exams; follow a healthy eating plan: eat different kinds of foods, and eat the right amount of carbohydrates with each meal; exercise regularly; take medicine exactly as prescribed; eat a low-fat and low-salt diet to keep your cholesterol and blood pressure at normal levels; do not smoke; keep blood pressure and cholesterol level under control; and carefully monitor blood pressure during pregnancy.

It would be understood that any of the methods described herein could be combined with one or more additional therapies including, but not limited to, laser therapy (e.g., focal or grid laser photocoagulation or focal laser treatment or scatter (pan-retinal) laser photocoagulation or scatter laser treatment), cryotherapy, fluorescein angiography, vitrectomy, corticosteroids (e.g., intravitreal triamcinolone acetonide), Anti-vascular endothelial growth factor (VEGF) treatment (e.g., Pegaptanib (Macugen; Pfizer, Inc., New York, USA), Ranibizumab (Lucentis; Genentech, Inc., South San Francisco, Calif., USA), Bevacizumab (Avastin; Genentech, Inc.), and VEGF Trap-Eye (Regeneron Pharmaceuticals, Inc., Tarrytown, N.Y., USA)), vitrectomy for persistent diffuse diabetic macular edema, pharmacologic vitreolysis in the management of diabetic retinopathy, fibrates, renin-angiotensin system (ras) blockers, peroxisome proliferator-activated receptor gamma (PPAR-y) agonists, Anti-Protein Kinase C (Ruboxistaurin), Islet cell transplantation; Therapeutic Oligonucleotides, Growth hormone and insulin growth factor (IGF), and control of systemic factors.

The terms "co-administration", "administered in combination with" and their grammatical equivalents or the like, as used herein, are meant to encompass administration of the selected compounds to a single patient, and are intended to include treatment regimens in which the compounds are administered by the same or different route of administration or at the same or different times. In some embodiments, the compounds described herein will be co-administered with other agents. These terms encompass administration of two or more compounds to a patient so that both compounds are present in the patient at the same time. These terms also encompass administration of one compounds and a treatment (e.g., laser therapy) to a patient so that both compounds are present in the patient at the same time. They include simultaneous administration in separate compositions, administration at different times in separate compositions, and/or administration in a composition in which both compounds are present. Thus, in some embodiments, the compounds and the other agent(s)/treatments are administered in a single composition or at a single time. In some embodiments, compounds and the other agent(s) are admixed in a single composition.

Laser Therapy

Laser photocoagulation has been used for the treatment of non-proliferative diabetic retinopathy, macular edema, and proliferative diabetic retinopathy since the 1960s.

Laser treatment generally targets the damaged eye tissue. Some lasers treat leaking blood vessels directly by "spot welding" and sealing the area of leakage (photocoagulation). Other lasers eliminate abnormal blood vessels that form from neovascularization. Lasers may also be used to destroy the peripheral parts of the normal retina that are not involved in seeing. This is done to help maintain vision in the central portion of the retina.

The two types of laser treatments commonly used to treat significant diabetic eye disease are:

Focal or Grid Laser Photocoagulation or Focal Laser Treatment

This type of laser energy is aimed directly at the affected area or applied in a contained, grid-like pattern to destroy damaged eye tissue and clear away scars that contribute to blind spots and vision loss. This method of laser treatment generally targets specific, individual blood vessels.

This is the main retinopathy laser treatment method for maculopathy from diabetic macular edema. The retinal laser seals retinal blood vessels that are leaking fluid and blood. This reduces further fluid and blood leakage, and reduces the swelling of the macula. The retinal laser may also somehow stimulate the retinal cells to 'pump' away any excess fluid at the macula. The laser is only directed at certain parts of the macula; the rest of the peripheral retina is untouched.

The aim of retinal laser treatment is not to improve the vision but to prevent it from getting worse.

Scatter (Pan-Retinal) Laser Photocoagulation or Scatter Laser Treatment

Pan-retinal photocoagulation is the first line of treatment for proliferative diabetic retinopathy. It applies about 1,200 to 1,800 tiny spots of laser energy to the outermost (peripheral) regions of the retina, leaving the inner portion untouched. This laser treatment can shrink the abnormal blood vessels. This treatment involves lasering large areas of the retina with the aim of coagulating or burning the ischemic retinal cells in the retinal periphery.

After pan retinal laser, the ischemic cells throughout the retinal periphery become replaced by scar tissue. This reduces the production of chemicals that stimulate the growth of the abnormal new blood vessels. Scatter laser treatment is usually done in two or more sessions.

Laser surgery is often helpful in treating diabetic retinopathy. To reduce macular edema, laser light is focused on the damaged retina to seal leaking retinal vessels. For abnormal blood vessel growth (neovascularization), the laser treatments are delivered over the peripheral retina. The small laser scars that result will reduce abnormal blood vessel growth and help bond the retina to the back of the eye, thus preventing retinal detachment. Laser surgery can greatly reduce the chance of severe visual impairment.

Cryotherapy

Cryotherapy (freezing) may be helpful in treating diabetic retinopathy. If the vitreous is clouded by blood, laser surgery cannot be used until the blood settles or clears. In some of these cases retinal cryotherapy may help shrink the abnormal blood vessels and bond the retina to the back of the eye.

Fluorescein Angiography

Fluorescein angiography has been useful as a research tool in understanding the clinic pathologic changes in the retinal circulation of eyes with diabetic retinopathy. It has also helped to classify diabetic retinopathy and to predict progression from baseline fluorescein angiography characteristics, particularly patterns of capillary nonperfusion.

It will identify sources of perimacular leakage and guide laser treatment of macular edema. Fluorescein angiography may not be needed in the treatment of Proliferative diabetic Retinopathy, but can be useful to assess signs of retinal ischemia. In some cases Fluorescein angiography can identify new vessels that are not otherwise seen.

In patients with impaired glucose tolerance, Fluorescein angiography may detect incipient retinal microvascular changes, indicating early break-down of the blood-retinal barrier before diabetes becomes manifest. These and other studies leave no doubt that fluorescein angiography may detect definite early retinal vascular changes in diabetic subjects without clinical retinopathy.

However, routine use of Fluorescein angiography in managing diabetic retinopathy at present should be guided by clinical experiences as little evidence is available to provide firm guidelines.

Vitrectomy

Vitrectomy, the surgical removal of the vitreous gel from the middle of the eye, is often used for patients with more advanced retinal disease. The procedure is intended to prevent the complete detachment of the retina. This procedure is commonly used to treat non-clearing vitreous hemorrhage, vitreomacular traction, epiretinal membranes, and retinal detachment.

During vitrectomy surgery, an operating microscope and small surgical instruments are used to remove blood and scar tissue that accompany abnormal vessels in the eye. Removing the vitreous hemorrhage allows light rays to focus on the retina again.

Vitrectomy often prevents further vitreous hemorrhage by removing the abnormal vessels that caused the bleeding. Removal of the scar tissue helps the retina return to its normal location. Vitrectomy may be followed or accompanied by laser treatment.

Vitrectomy can reduce visual loss if performed early in people with vitreous haemorrhage, especially if they have severe proliferative retinopathy.

Conventional laser treatment may fail in eyes with vitreous hemorrhage or in eyes with tractional retinal detachments and active progressive PDR. Early vitrectomy has been shown to improve visual recovery in patients with proliferative retinopathy and severe vitreous hemorrhage.

Refractive Eye Surgery

Refractive eye surgery involves various methods of surgical remodeling of the cornea or cataract (e.g. radial keratotomy uses spoke-shaped incisions made with a diamond knife). In some instances, excimer lasers are used to reshape the curvature of the cornea. Successful refractive eye surgery can reduce or cure common vision disorders such as myopia, hyperopia and astigmatism, as well as degenerative disorders like keratoconus. Other types of refractive eye surgeries include keratomilleusis (a disc of cornea is shaved off, quickly frozen, lathe-ground, then returned to its original power), automated lamellar keratoplasty (ALK), laser assisted in-situ keratomileusis (LASIK), intraLASIK, laser assisted sub-epithelial keratomileusis (LASEK aka Epi-LASIK), photorefractive keratectomy, laser thermal keratoplasty, conductive keratoplasty, limbal relaxing incisions, astigmatic keratotomy, radial keratotomy, mini asymmetric radial keratotomy, hexagonal keratotomy, epikeratophakia, intracorneal ring or ring segment implant (Intacs), contact lens implant, presbyopia reversal, anterior ciliary sclerotomy, laser reversal of presbyopia, scleral expansion bands, and Karmra inlay.

Corneal Surgery

Examples of corneal surgery include but are not limited to corneal transplant surgery, penetrating keratoplasty, keratoprosthesis, phototherapeutic keratectomy, pterygium excision, corneal tattooing, and osteo-odonto-keratoprosthesis (OOKP). In some instances, corneal surgeries do not require a laser. In other instances, corneal surgeries use a laser (e.g., phototherapeutic keratectomy, which removes superficial corneal opacities and surface irregularities). In some instances, patients are given dark eyeglasses to protect their eyes from bright lights after these procedures.

Cataract and Glaucoma Surgery

Cataract surgery involves surgical removal of the lens and replacement with a plastic intraocular lens. Typically, a light is used to aid the surgeon.

Glaucoma surgery facilitates the escape of excess aqueous humor from the eye to lower intraocular pressure. In some instances, these medical procedures use a laser (e.g., laser trabeculoplasty applies a laser beam to burn areas of the trabecular meshwork, located near the base of the iris, to increase fluid outflow; laser peripheral iridotomy applies a laser beam to selectively burn a hole through the iris near its base; etc.). Canaloplasty is an advanced, nonpenetrating procedure designed to enhance drainage through the eye's natural drainage system utilizing microcatheter technology in a simple and minimally invasive procedure. Other medical procedures used for the treatment of glaucoma include lasers, non-penetrating surgery, guarded filtration surgery, and seton valve implants.

Corticosteroids (Intravitreal Triamcinolone Acetonide)

Corticosteroid reduces vascular permeability and reduces the breakdown of the blood retinal barrier. It inhibits VEGF gene transcription and translation and leukocyte adhesion to vascular walls. They especially address the complications related to increased vascular permeability.

Intra vitreal triamcinolone acetonide (IVTA) (4 mg), helped to reduce the risk of progression of diabetic retinopathy. However, the study concluded that use of IVTA to reduce the likelihood of progression of retinopathy is not warranted at this time because of the increased risk of glaucoma and cataract associated with IVTA and because PDR already can be treated successfully and safely with panretinal photocoagulation.

Several small randomized clinical trials demonstrated that the combination of laser photocoagulation (panretinal and macular) with IVTA was associated with improved best-corrected visual acuity and decreased central macular thickness and total macular volume when compared with laser photocoagulation alone for the treatment of PDR and macular edema. On the other hand, a recent study demonstrated no beneficial effect of combined IVTA plus panretinal photocoagulation and macular photocoagulation in eyes with coexisting high-risk proliferative diabetic retinopathy (PDR) and clinically significant macular edema as compared with panretinal photocoagulation and macular photocoagulation as standard treatment in those patients.

Anti-Vascular Endothelial Growth Factor (VEGF) Treatment

Currently, there are four anti-VEGF agents that are used for the management of diabetic retinopathy, including Pegaptanib (Macugen; Pfizer, Inc., New York, USA), Ranibizumab (Lucentis; Genentech, Inc., South San Francisco, Calif., USA), Bevacizumab (Avastin; Genentech, Inc.), and VEGF Trap-Eye (Regeneron Pharmaceuticals, Inc., Tarrytown, N.Y., USA).

Pegaptanib is a pegylated RNA aptamer directed against the VEGF-A 165 isoform. A phase II clinical trial of intravitreal pegaptanib in patients with DME with 36 weeks of follow-up demonstrated better visual acuity outcomes, reduced central retinal thickness, and reduced need for additional photocoagulation therapy. A retrospective analysis of the same study on patients with retinal neovascularization at the baseline showed regression of neovascularization after intravitreal pegaptanib administration. Recently in a retrospective study it was demonstrated that repeated intravitreal pegaptanib produced significant improvement in best-corrected visual acuity and reduction in mean central macular thickness in patients with diabetic macular edema.

Ranibizumab is a recombinant humanized monoclonal antibody fragment with specificity for all isoforms of human VEGF-A. Pilot studies of intravitreal ranibizumab demonstrated reduced foveal thickness and maintained or improved visual acuity in patients with DME. Recently, Nguyen et al. (2009) demonstrated that during a span of 6 months, repeated intravitreal injections of ranibizumab produced a significantly better visual outcome than focal/grid laser treatment in patients with DME. Diabetic Retinopathy Clinical Research Network (2010a) evaluated intra-vitreal 0.5 mg ranibizumab or 4 mg triamcinolone combined with focal/grid laser compared with focal/grid laser alone for treatment of diabetic macular edema. Nguyen et al. (2010), in a randomized study, showed that intraocular injection of ranibizumab provided benefit for diabetic macular edema for at least 2 years, and when combined with focal or grid laser treatments, the amount of residual edema was reduced, as were the frequency of injections needed to control edema.

VEGF Trap is a 115 kDa recombinant fusion protein consisting of the VEGF binding domains of human VEGF receptors 1 and 2 fused to the Fc domain of human IgG1. One pilot study showed that a single intravitreal injection of VEGF Trap-Eye was well tolerated and was effective in patients with diabetic macular edema.

Bevacizumab is a full length recombinant humanized antibody active against all isoforms of VEGF-A. It is FDA-approved as an adjunctive systemic treatment for metastatic colorectal cancer. Several studies reported the use of the off-label intra vitreal bevacizumab (IVB) to treat diabetic macular edeme (DME), complications of proliferative diabetic retinopathy (PDR), and iris neovascularization. Several studies demonstrated that IVB injection resulted in marked regression of retinal and iris neo-vascularization, and rapid resolution of vitreous hemorrhage in patients with Proliferative diabetic retinopathy (PDR). In addition, IVB injection was demonstrated to be an effective adjunctive treatment to PRP in the treatment of high-risk Proliferative diabetic retinopathy (PDR) and neovascularglaucoma. The short-term results suggest that IVB has the potential not only to prevent the increase in retinal thickness, but also reduce the retinal thickness of eyes with diabetic macular edema (DME) after cataract surgery.

Vitrectomy for Persistent Diffuse Diabetic Macular Edema

Vitrectomy with removal of the premacular posterior hyaloid for persistent diffuse macular edema (DME) has gained rapid widespread acceptance. The large number of series evaluating the efficacy of vitrectomy (with or without internal limiting membrane peeling) has yielded conflicting results. In a trail it was observed that vitrectomy with internal limiting membrane peeling was superior to observation in eyes with persistent diffuse diabetic macular edema (DME) that previously failed to respond to conventional laser treatment and positively influenced distance and reading visual acuity as well as the morphology of the edema. Other studies suggested that vitrectomy with and without internal limiting membrane peeling may provide anatomic and visual benefit in eyes with diffuse nontractional unresponsive diabetic macular edema (DME) refractory to laser photocoagulation.

Other studies showed that the benefits of vitrectomy for diabetic macular edema (DME) in terms of visual acuity and macular thickness were limited to patients who exhibited signs of macular traction, either clinically and/or on optical coherence tomography.

Pharmacologic Vitreolysis in the Management of Diabetic Retinopathy

During a demonstration it was observed that intravitreal injection of microplasmin with induction of the combination of posterior vitreous detachment (PVD) and vitreous liquefaction increased intravitreal oxygen tension. On the other hand, hyaluronidase induced vitreous liquefaction without posterior vitreous detachment (PVD) induction failed to increase intravitreal oxygen tension. Moreover, when microplasmin treated animals were exposed to 100% oxygen, there was an accelerated increase in oxygen levels in the midvitreous cavity compared to control or hyaluronidase treated eyes. These findings suggest that the beneficial effects of surgical vitrectomy in increasing oxygen tension in the vitreous cavity may be reproduced with enzymatic induction of PVD and vitreous liquefaction without the time, risks, and expense of surgery. In 2009, it was demonstrated that intravitreal injection of autologous plasmin enzyme without the performance of vitrectomy induced complete PVD and effectively reduced macular thickening due to refractory diffuse diabetic macular edema and improved visual acuity. Therefore, a traumatic pharmacologic separation of the posterior vitreous cortex with clean cleavage between the internal limiting membrane and the posterior hyaloids without performing a vitrectomy can reduce the risk of intraoperative iatrogenic damage such as retinal tears, and damage to the nerve fibers, and the postoperative sequelae.

Fibrates

Fibrates are widely prescribed lipid-lowering drugs in the treatment of dyslipidemia. Their main clinical effects, mediated by peroxisome proliferative activated receptor alpha activation, are a moderate reduction in total cholesterol and low-density lipoprotein cholesterol levels, a marked reduction in triglycerides and an increase in high-density lipoprotein cholesterol. The Fenofibrate Intervention and Event Lowering in Diabetes (FIELD) study demonstrated that long-term lipid-lowering therapy with fenofibrate reduced the progression of diabetic retinopathy and the need for laser treatment in patients with type 2 diabetes, although the mechanism of this effect does not seem to be related to plasma concentration of lipids. Recently, ACCORD Study Group (2010) demonstrated that fenofibrate for intensive dyslipidemia therapy reduced the rate of progression of diabetic retinopathy in persons with type 2 diabetes.

Renin-Angiotensin System (RAS) Blockers

Several studies suggested that RAS blockers might reduce the burden of diabetic retinopathy. The findings of the Eurodiab Controlled trial of Lisinopril in Insulin-dependent Diabetes (EUCLID) suggested that blockade of the renin-angiotensin system with the angiotensin-converting enzyme inhibitor lisinopril could reduce both incidence and progression of retinopathy in type 1 diabetes.

Peroxisome Proliferator-Activated Receptor Gamma (PPAR-γ) Agonists

The PPARγ agonist rosiglitazone inhibited both the retinal leukostasis and retinal leakage observed in the experimental diabetic rats. In addition, the decreased expression of the endogenous PPARγ in mice leads to the aggravation of retinal leukostasis and retinal leakage in diabetic mice. Rosiglitazone maleate (Avandia; GlaxoSmithKline, North Carolina, USA) is an orally administered medication used to improve glycemic control in patients with diabetes mellitus. This medication activates the PPARγ and leads to insulin sensitization in adipose and other tissues, with potential anti-angiogenic activity.

Anti-Protein Kinase C (Ruboxistaurin)

PKC mediates several ocular complications of diabetes. It is activated by VEGF and is a potential target for therapy of diabetic retinopathy.

Roboxistaurin (RBX), an oral PKCβ inhibitor is a selective inhibitor with adequate bioavailability to permit oral administration once daily. In the Protein Kinase C β inhibitor-Diabetic Retinopathy Study 2 (PKC-DRS2), oral administration of RBX (32 mg per day) reduced sustained moderate visual loss, need for laser treatment for macular edema, and macular edema progression, while increasing occurrence of visual improvement in patients with non-proliferative retinopathy.

Islet Cell Transplantation

Recent studies demonstrated that improved islet transplant outcomes could be observed with enhanced islet isolation, glucocorticoid-free immunosuppression, and provision of an adequate islet mass of more than 10,000 islet equivalents per kg of body weight. These improvements have resulted in benefits to type 1 diabetic subjects, including long-term C-peptide secretion, improved glycemic control, and reduced hypoglycemic episodes.

Therapeutic Oligonucleotides

Oligonucleotides represent one of the new treatment entities targeting specific links in the disease process. There are two main categories of oligonucleotide therapeutic agents: antisense oligonucleotides, including short interfering RNA (siRNA), and oligonucleotide aptamers.

Antisense oligonucleotides are novel therapeutics designed to bind to specific messenger RNA (mRNA) that result in the degradation of the message encoding the targeted protein, thus affecting a decrease in the production of a particular protein associated with the targeted disease. Antisense oligonucleotide delivery via an intravitreous injection is a reasonable strategy in the treatment of retinal diseases. Alternative options for the drug delivery of antisense and other oligonucleotides have been under investigation, including periorbital administration, iontophoresis, and sustained release formulations.

Growth Hormone and Insulin Growth Factor (IGF)

Growth hormone and Insulin growth factor (IGF) modulate the function of retinal endothelial precursor cells and drive retinal angiogenesis in response to hypoxia; IGF 1 can also disrupt the blood retina barrier and increase retinal vascular permeability.

Intravitreal Hyaluronidase

Intravitreal ovine hyaluronidase injection is effective in clearing vitreous hemorrhage. Several human case series demonstrated that intravitreal injection of autologous plasmin enzyme was a safe and effective adjunct to vitreous surgery for the treatment of diabetic macular edema and proliferative diabetic retinopathy.

Control of Systemic Factors:

Primary prevention of diabetic retinopathy involves strict glycemic, lipid and blood pressure control. Some of the systemic factors that should be controlled for prevention of diabetic retinopathy are detailed below.

Glycemic Control

Hyperglycemia instigates the cascade of events that eventually leads to the development of diabetic retinopathy. Thus, one treatment that may be used to slow down the progression of diabetic retinopathy is glycemic control. Glycemic control may reduce the risk of development and progression of diabetic retinopathy in both type 1 and type 2 diabetes.

Blood Pressure Control

Hypertension exacerbates diabetic retinopathy through increased blood flow and mechanical damage (stretching) of vascular endothelial cells, stimulating release of VEGF. Tight blood pressure control may reduce the risks of retinopathy progression by about a third, visual loss by half, and the need for laser treatment by a third in people with type 2 diabetes. Blood pressure control may also reduce the incidence and progression of diabetic retinopathy.

Serum Lipid Control

Dyslipidaemia has a role in the pathogenesis of Diabetic Retinopathy. The severity of retinopathy was associated with increasing triglycerides and inversely associated with HDL cholesterol. Hydroxy methyl glutaryl coenzyme A (HMG CoA) inhibitors may be useful in the management of Diabetic Retinopathy (DR) and diabetic macular oedema (DMO) in patients with Dyslipidaemia.

EXAMPLES

The application may be better understood by reference to the following non-limiting examples. The following examples are presented in order to more fully illustrate representative embodiments and should in no way be construed, however, as limiting the broad scope of the application.

The term ACU-4429 refers to the compound (R)-3-amino-1-(3-(cyclohexylmethoxy)phenyl)propan-1-ol. The term ACU-4935 refers to the compound (R)-3-amino-1-(3-(2-propylpentyloxy)phenyl)propan-1-ol.

Example 1: Accepted Animal Models of Diabetic Retinopathy

Mice, rats, hamsters, dogs, cats, and monkeys are some of the common animal models that are used for studying Diabetic Retinopathy.

Animal experiments have been pivotal in the understanding of the pathogenesis of retinopathy since systematic structural, functional and biochemical studies cannot be undertaken in human subjects Animal experiments are of immense importance in an attempt to develop adjuvant treatment strategies. Characteristic retinal lesions in diabetes have successfully been reproduced in experimental diabetic or galactose-fed animals.

Data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration arrange that includes the IC50 (i.e., the concentration of the test compound which achieves a half-maximal inhibition) as determined in cell culture. Levels in plasma can be measured, for example, by high performance liquid chromatography. Such information can be used to more accurately determine useful doses in humans.

Some of the common animal models for studying Diabetes Retinopathy along with the source and relevant text are detailed below:

Mice

Protocols which may be used to test compounds for efficacy of treatment in mice include those described in, for example, *Diabetic Retinopathy* by Elia Duh, Springer, Humana Press, 2009; Kern et al. (*Arch Ophthalmol.* 1996; 114(8):986-990); Feit-Leichman et al. (*Investigative Ophthalmology & Visual Science*, 46(11): 4281-4287, November 2005).

Rats

Protocols which may be used to test compounds for efficacy of treatment in rats include those described in, for example, *Diabetic Retinopathy* by Elia Duh, Springer, Humana Press, 2009; Sima et al. (*Current Eye Research*, 1985, Vol. 4(10) Pages 1087-1092); Kato et al. (*Journal of Diabetes and Its Complications*, Volume 17(6): 374-379, November 2003); Sima et al. (*Metabolism*, 32(7, Suppl. 1): 136-140, July 1983); Lu et al. (*Journal of Ophthalmology*, 47(1): 28-35, 2003); and Deng et al. (*International Journal of Diabetes*, vol. 6 (issue 1), 1998).

Hamsters and Other Rodents

Protocols which may be used to test compounds for efficacy of treatment in hamsters and other rodents include those described in, for example, Diabetic Retinopathy by Elia Duh, Springer, Humana Press, 2009.

Dogs

Protocols which may be used to test compounds for efficacy of treatment in dogs include those described in, for example, *Diabetic Retinopathy* by Elia Duh, Springer, Humana Press, 2009; Engerman et al. (*Arch Ophthalmol.* 1995; 113(3):355-358); and Kador et al., (*Arch Ophthalmol.* 1990; 108(9):1301-1309).

Cats

Protocols which may be used to test compounds for efficacy of treatment in cats include those described in, for example, *Diabetic Retinopathy* by Elia Duh, Springer, Humana Press, 2009; Mansour et al. (*Investigative Ophthalmology & Visual Science*, Vol. 31, No. 3, March 1990); and Henson and O'Brien (ILAR Journal Volume 47(3): 234-242).

Monkeys/Primates

Protocols which may be used to test compounds for efficacy of treatment in monkeys and primates include those described in, for example, Kim et al. (*Invest Ophthalmol Vis Sci.* 2004; 45:4543-4553); Akimba: A Novel Murine Model for Diabetic Retinopathy (www.Bio-link.com); and *Diabetic Retinopathy* by Elia Duh, Springer, Humana Press, 2009.

Example 2: Use of Compounds for the Treatment of Diabetic Retinopathy

A single-center, open-label, dose-escalating pilot study is initiated to evaluate the biologic activity of oral administration of compounds described herein in patients with center-involving clinically significant diabetic macular edema (DME) and to report any associated adverse events. Patients with DME involving the center of the macula and best-corrected visual acuity (BCVA) in the study eye between 20/63 and 20/400 are enrolled.

Eligible patients are randomly assigned in a 1:1 ratio to receive daily oral doses of compound (2 mg, 5 mg, 7 mg, 10 mg or 20 mg) administered until month 24. Primary end points are the frequency and severity of ocular and systemic adverse events. Secondary end points are 1) best corrected visual assessment as assessed with the Early Treatment Diabetic Retinopathy Study (ETDRS) chart, with the use of standardized refraction and testing protocol at a starting test distance of 2 m and 2) measurement of retinal thickness by optical coherence tomography. The evaluating physician is unaware of the patient's treatment assignment; the physician who administers the dose is aware of the patient's treatment assignment regarding test or sham treatment but is unaware of the dose of compound. Other personnel at each study site, patients, and personnel at the central reading center are unaware of the patient's treatment assignment.

Efficacy analyses are performed on an intention-to-treat basis among all patients with the use of a last-observation-carried-forward method for missing data. For all pair-wise comparisons, the statistical model is adjusted for baseline score for visual acuity (<55 letters vs. ≥55 letters). Between-group comparisons for dichotomous end points are performed with the use of the Cochran chi-square test. Change from baseline visual acuity is analyzed with the use of analysis-of-variance models. For end points for lesion characteristics, analysis-of-covariance models adjusting for the baseline value are used. The Hochberg-Bonferroni multiple-comparison procedure is used to adjust for the two pair-wise treatment comparisons for the primary end point. Safety analyses include all treated patients.

Compounds are expected to be well-tolerated therapy for patients with DME. The compounds will have the potential to maintain or improve best corrected visual acuity and reduce retinal thickness in patients with center-involved clinically significant DME.

Example 3: Manganese-Enhanced Magnetic Resonance Imaging (MEMRI) Protocol

Rats are to be maintained in regular laboratory lighting (12 hours light, 12 hours dark) prior to start of experimental period—light exposure, bleaching, dark adaption will vary by cohort (see below).

Animals are to be dosed by oral gavage according to group assignment below. Rats are to be weighed each week of the experimental period.

Dilate pupils by applying 1 drop of tropicamide (0.5%) 10-30 minutes before photobleaching. Photobleach animals for 10 minutes by exposure to 5000 lux 4 hours before MRI imaging.

Inject rats immediately after bleach, 4 hours prior to the start of imaging session. MEMRI signal reflects state of expression of activity-dependent channels during experimental period.

Inject $MnCl_2$ is intraperitoneally in lower right abdomen of awake rat.

$MnCl_2$ is injected at 60 mg/kg using a 20 mg/mL stock solution.

Mark each rat injected and record injection, time of bleach, start and end of imaging as well as light conditions in notebook Keep rats in dark (IOP room) during the 4 hours between injection and transport to the imaging center for practice experiments for all groups except group 4. Keep animals from group 4 exposed to light during 4 hours between MnCl$_2$ injection and MRI imaging. Otherwise follow light-dark-bleaching cycle described for each cohort.

Transport rats to imaging center via IACUC-approved route, following closely light-dark cycle for each cohort.

Image either both eyes of each rat, or unilateral as mandated by particular experiment.

MRI parameters include:

A snapshot FLASH inversion recovery (IR) imaging sequence is used to acquire a single imaging slice bisecting the retina in the axial and sagittal planes, using a 12 mm inner diameter linear surface coil. Imaging parameters are TR/TE=1000/2.7 ms, with a 125 ms inversion time (TI), sweep width=73.5 kHz, number of acquisitions=120; slice thickness=0.7 mm, field of view=12 mm×12 mm, with 256×256 data matrix, resulting in an in-plane resolution of 47 microns. The approximate scan time per animal is ~16 minutes.

The total time required to image one eye (including setup and scout imaging) is approximately 1 hour. If animal moves, re-image.

(T1 Mapping): Determined as Optimal During Protocol Development

A snapshot FLASH inversion recovery (IR) imaging sequence is used to acquire a single imaging slice bisecting the retina in the axial and sagittal planes, using a 12 mm inner diameter linear surface coil. Imaging parameters are TR/TE=2000/2.7 ms, sweep width=73.5 kHz, number of acquisitions=32; slice thickness=0.7 mm, field of view=12 mm×12 mm, with 192×192 data matrix (zero padded to 256×256), resulting in a nominal in-plane resolution of 47 microns. The signal acquired at six inversion times [TI=50, 150, 300, 400, 900, 1800 ms] were used to obtain a T1 map.

Wait until animal has woken up from anesthesia before transporting. Use heat lamp after imaging to help maintain body temperature while animal is waking up from anesthesia Cohorts

| Group | Drug Treatment | Light Treatment After Bleach | Number of Animals |
|---|---|---|---|
| 1 | ACU-4429 (1 mg/kg/day) | Dark Adaptation | 5 |
| 2 | ACU-4429 (10 mg/kg/day) | Dark Adaptation | 5 |
| 3 | ACU-4429 Vehicle | Dark Adaptation | 5 |
| 4 | ACU-4429 Vehicle | Light Adaptation | 5 |
| 5 | Retinyl Acetamide (200 mg/kg) | Dark Adaptation | 5 |
| 6 | Retinyl Acetamide Vehicle | Dark Adaptation | 5 |
| | Total | | 30 |

Study Design

Timeline for Groups 1-3 are illustrated in FIG. 1.

Figure 2:
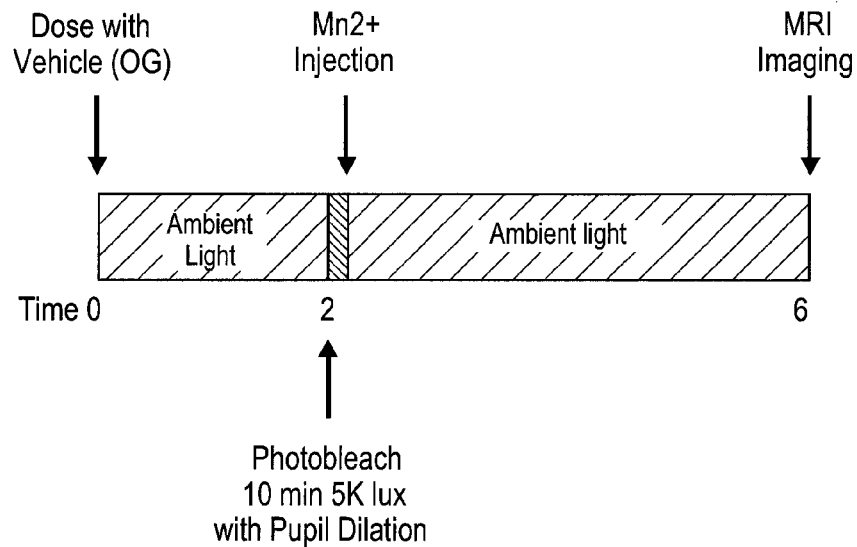
FIG. 2 is a graph depicting the timeline for Group 4 as described in Example 3.

Timeline for Group 4 is illustrated in FIG. 2.

Figure 3:
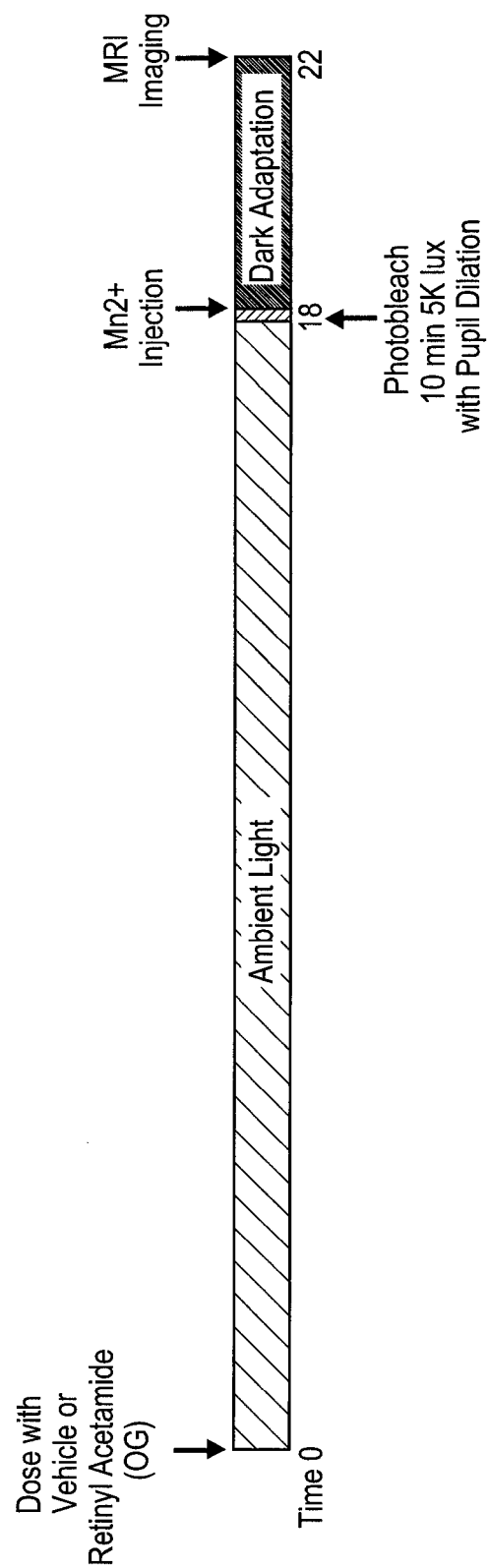
FIG. 3 is a graph depicting the timeline for Groups 5-6 as described in Example 3.

Timeline for Groups 5-6 are illustrated in FIG. 3.

Single Dose Study

The purpose of this study is to determine whether a single (high) dose of ACU-4429 reduces the return of retinal cationic activity (Mn$^{2+}$ uptake) following dark adaptation post-bleaching. Groups 1-4 (ACU-4429 vs. vehicle) will be dosed and kept in room light for 2 hours. Groups 5 and 6 (retinal acetamide vs. vehicle) will be dosed 18 hours before bleach. The animals will have pupil dilation and be exposed to a moderate bleaching white light (5,000 lux of diffuse white fluorescent light) for 10 minutes Immediately after bleach, the animals will be intraperitoneally (IP) injected with Mn$^{2+}$, followed by 4 hrs of dark adaptation (animals will be kept dark-adapted while in the imaging queue). Animals in Groups 3 will be left in ambient room light to serve as light control (the expectation is that the retinas treated with Retinyl acetamide and ACU-4429 to behave as if they were light adapted). MRI imaging (30 minutes-1 hr per animal) will be conducted at 4 hours after Mn$^{2+}$ injection (i.p.) and will be performed in the same light conditions animals were housed in prior to the imaging. Dosing of the animals will be staggered to insure that the time from dose to imaging is the same for all animals Multi-Dose Study The purpose of this study is to test whether repeat ACU-4429 (10 mg/kg/day) treatment in normal cyclic light over time reduces the return of retinal cationic activity (Mn$^{2+}$ uptake) following dark adaptation. Three groups: Group 1: ACU-4429 at 5 mg/kg bid (10 mg/kg/day); Group 2: vehicle (dark adapted); Group 3: vehicle (room light). All dosing will be done at lights on and at lights off for 6 days under conditions of normal cyclic light exposure (12 hours of about 100 lux of diffuse white fluorescent light) Immediately following the morning dose of Day 7, a drop of atropine sulfate (1%) will be applied to both eyes of all animals to dilate the pupils. Six hours after administration of the last dose and after at least 6 hours in normal light, Group 1 (ACU-4429) and Group 2 (Dark adapted) will be IP injected with Mn$^{2+}$, followed by 4 hrs of dark adaptation (animals will be kept dark-adapted while in the imaging queue) and imaged in the dark (30 minutes-1 hr per animal). Group 3 (room light) will be IP injected with Mn$^{2+}$ 6 hours after last dose and remain in normal room light 4 more hours until imaging. Imaging of Group 3 will occur under normal light.

Example 4: Reduction of Oxygen-Induced Retinopathy in Rats

Purpose:

A test compound is assessed in rats with oxygen-induced retinopathy (OIR), a common model of human retinopathy of prematurity (ROP). Both OIR and ROP are characterized by abnormal retinal vasculature and by lasting dysfunction of the neural retina.

Methods:

OIR is induced in four litters of Sprague-Dawley pups (N=24) by exposure to alternating periods of 50% and 10% oxygen from the day of birth (P0) to P14. The light cycle is 12 hr light (10-30 lux) and 12 hr dark; the light-to-dark transition coincides with each oxygen alternation. For 15 days beginning P7, within one hour of this transition, the first and fourth litters are orally administered 6 mg/kg of a clinical development candidate; the second and third litters receive only vehicle. At P20-22, when marked retinal vascular abnormality is typically observed, electroretinograms are recorded and receptor and post-receptor function are evaluated. Treatment effects are evaluated by ANOVA.

Assessment:

Maximal rod response and the amplification constant of phototransduction changed by treatment with the clinical development candidate are assessed. Additionally, the time-constant of deactivation of phototransduction is assessed by a double-flash protocol. Post-receptor sensitivity (log s) and maximal scotopic b-wave amplitude are also assessed. Alteration of the photoreceptor response after treatment with the clinical development candidate and responses originating in the inner retina may be assessed. The inner retina is supplied by the retinal vasculature; quantitative image analysis of fundus photographs is used to determine the degree of vascular abnormality associated with OIR following such treatment. It is anticipated that the degree of vascular abnormality will be reduced in animals treated with the clinical development candidate.

Example 5: Visual Cycle Modulation and Rod Function in a Rat Model of ROP

Rat models of ROP provide a convenient in vivo system in which the relation of the photoreceptors to the retinal vasculature can be studied and manipulated.

Both OIR and ROP are characterized by lasting dysfunction of the neural retina and by abnormal retinal vasculature. The systemic effects of a clinical development candidate, a visual cycle modulator (VCM), are studied on rats with oxygen-induced retinopathy (OIR).

Retinopathy is induced in Sprague-Dawley pups (N=46) by exposing them to alternating 24 hour periods of 50±1% and 10±1% oxygen from the day of birth to postnatal day (P) 14. The light cycle is controlled at 12 hours 10-30 lux and 12 hours dark, except during test days when constant darkness is maintained. The light-to-dark transition is timed to coincide with each oxygen alternation.

For two weeks, beginning on P7, during this transition, the first and fourth litters are orally administered 6 mg/kg of the clinical development candidate; the second and third litters are administered an equivalent volume of vehicle (20% dimethyl sulfoxide, DMSO) alone. The administration schedule is designed to continue over the age range that begins with the onset of rapid increase in the rhodopsin content of the retina and lasts until rhodopsin content exceeds 50% of its adult amount (Fulton and Baker, *Invest Ophthalmol Vis Sci* (1984) 25:647).

The treated rats are held in room air (20.8% oxygen) for approximately 20 minutes between each oxygen alternation from P7-14. The rats are assessed following a longitudinal design with tests at P20-22, P30-32, and P60-62. These dates are selected because they capture the height of vascular abnormality, a period of marked recovery, and an adult age, respectively. At each test age, the function of the neural retina and the morphology of the retinal vasculature are assessed using non-invasive techniques.

Shortly (0-2 days) after the final dose, the effects of the compounds are assessed on the neural retina by electroretinography (ERG). The timing and intensity of the stimuli, which is designed to assess rod photoreceptor and rod-mediated post-receptor neural function, are under computer control. Two sets of experiments are performed. In the first, rod and rod-mediated neural function in the dark-adapted retina are assessed. In the second, the recovery of the rod photoreceptor from a bright, rhodopsin-bleaching stimulus is assessed. Each set of experiments is performed on approximately half of the patients from each litter.

Figure 19:
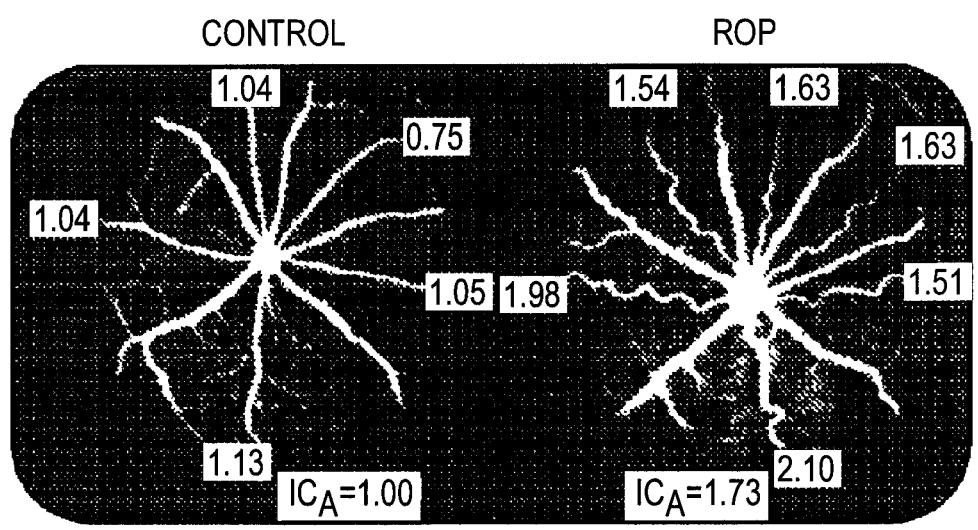
FIG. 19 is a rat model of retinopathy of prematurity. (a) Scanning laser ophthalmoscope (SLO) images obtained using blue (488 nm) laser stimulation (Seeliger et al., *Vision Res.*, (2005) 45: 3512-9) after injection of fluorescein in 22 day old control and ROP rats. (Pigmented rats are used to facilitate SLO imaging.) The integrated curvature of each retinal arteriole is expressed as a proportion of the mean (ICA) in the control. The higher ICA value for the ROP rat reflects the greater tortuosity of its arterioles. The choroidal appearance is similar in the control and ROP fundi. (b) Sample electroretinographic (ERG) responses to full-field stimuli in control and ROP rats. Both rats are tested with the same flash intensities, as indicated. The vertical grey lines indicate the time at which the flash is presented.
Figure 20:
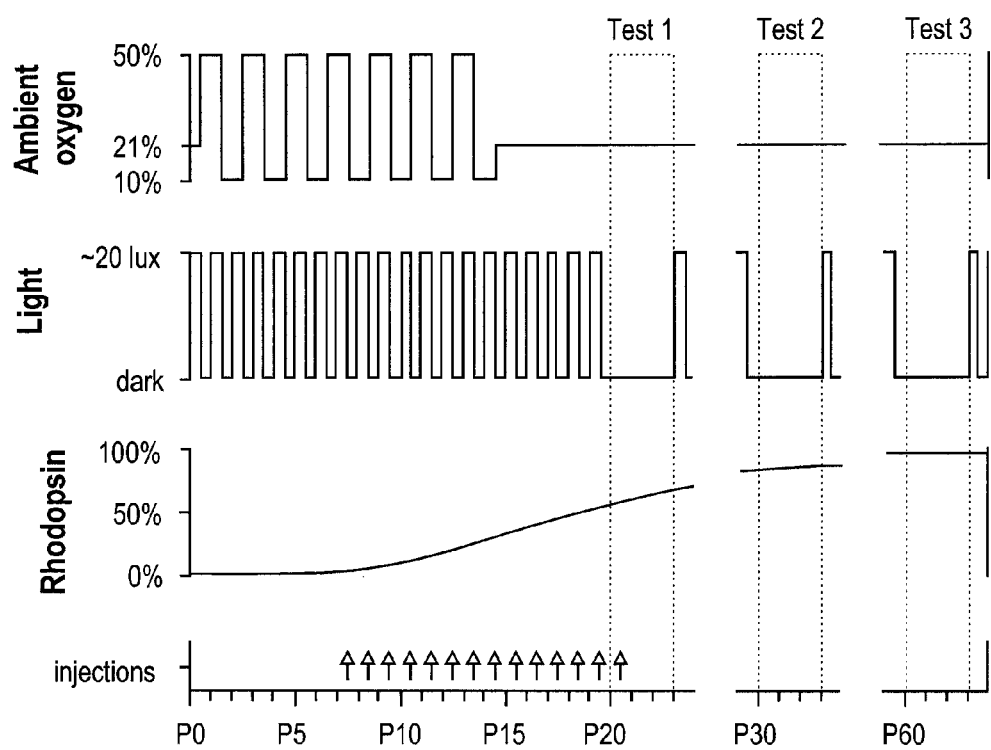
FIG. 20 illustrates features of the experimental paradigm. The ambient oxygen and light cycle were tightly controlled and synchronized. Dosing with the VCM is designed to target the rapid growth phase of the developmental increase in rhodopsin in the retina (arrows). Area in dashed line box indicate the three test windows.
Figure 21:
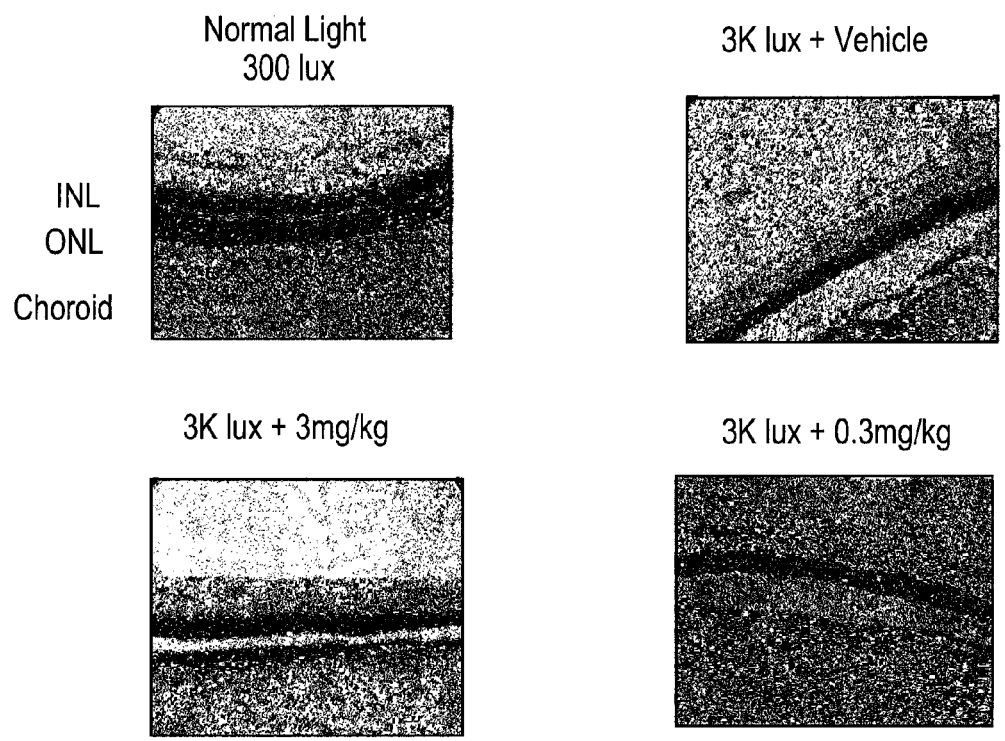
FIG. 21 provides pictures of H&E staining of paraffin sections (from example 7, chronic light induce CNV). The outer nuclear layer is thinnest in sections from eyes of animals treated with light and vehicle.

To assess whether VCM treatment affected the retinal vasculature, wide-field images of the ocular fundus are obtained that show the major vessels of the retina following each ERG session. As shown in FIG. 19, the images are composited to display a complete view of the posterior pole, the region within the circle bounded by the vortex veins and concentric to the optic nerve head, and the retinal region that in human patients is most important to the diagnosis of high-risk ROP. The arterioles are analyzed with RISA custom image analysis software (Gelman, *Invest Ophthalmol Vis Sci* (2005) 46: 4734).

Example 6: Animal Models of Laser-Induced Choroidal Neovascularization and Macular Degeneration Murine Model of Choroidal Neovascularization The effect of the VCM compounds described herein can be assessed in a murine model of choroidal neovascularization.

Briefly, 4 to 5 week old C57BL/6 mice are anesthetized ketamine hydrochloride:xylazine (100 mg/kg:10 mg/kg) and the pupils dilated with 1% tropicamide (Alcon Laboratories, Inc Fort Worth, Tex.). Three burns of a 532-nm diode laser photocoagulation (75-pm spot size, 01-second duration, 120 mW) are delivered to each retina using the slit lamp delivery system of a photocoagulator (OcuLight; Iridex, Mountain View, Calif.) and a handheld cover slip as a contact lens. Burns are performed in the 9, 12 and 3 o'clock positions of the posterior pole of the retina. Production of a bubble at the time of lasering, which indicates rupture of Bruch's membrane, is an important factor in obtaining CNV; thus only burns in which a bubble is produced are included in the study.

Four independent experiments are performed to investigate the effect of a clinical development candidate when orally administered on day 0 after rupture of Bruch's membrane. Mice in Group 1-4 are orally administered a daily dose of 0.3, 1, 3, and 10 mg/kg of the clinical development candidate, respectively. Group 4 receive vehicle only.

After 14 days, mice are anesthetized and perfused with fluorescein-labeled dextran ($2 \times 10^6$ average molecular weight, Sigma-Aldrich) and choroidal flat mounts are prepared. Briefly, the eyes are removed, fixed for 1 hour in 10% phosphate-buffered formalin, and the cornea and lens are removed. The entire retina is carefully dissected from the eyecup, radial cuts are made from the edge of the eyecup to the equator in all four quadrants, and the retina is flat-mounted in aqueous mounting medium (Aquamount; BDH, Poole, UK). Flat mounts are examined by fluorescence microscopy (Axioskop; Carl Zeiss Meditec, Thornwood, N.Y.), and the images are digitized with a three charge-coupled device (CCD) color video camera (1K-TU40A, Toshiba, Tokyo, Japan). A frame grabber image-analysis software is used to measure the area of each CNV lesion. Statistical comparisons are made using ANOVA with Dunnett's correction for multiple comparisons.

Murine Model of Suppression of Choroidal Neovascularization

Though animals do not develop age related macular degeneration (AMD) per se, choroidal neovascularization resembling that seen in AMD can be produced by using a laser to produce focal disruptions in Bruch's membrane and the overlying retinal pigment epithelium (RPE). This injury stimulates the abnormal growth of underlying choroidal capillaries into the RPE layer and subretinal space. Disruption of Bruch's membrane is common to all forms of choroidal neovascularization (CNV), including that which characterizes the wet form of AMD.

In the laser-induced model of choroidal neovascularization, groups of 9 or 10 mice are treated with oral administration of (1) a clinical development candidate, or (2) sham treatment one day prior to laser injury and on days 2, 5, 8, and 11 after laser. At 14 days after laser injury, the mice are injected intravenously with fluorescein-labeled dextran (50 mg), euthanized, and eyes are rapidly dissected for choroidal flat mounts or frozen in optimum cutting temperature embedding compound and sectioned for evaluation of the lesions.

CNV lesions are visualized by fluorescein angiography and graded according to standard procedures.

Example 7: Efficacy Study in the Chronic Light-Induced Choroidal Neovascularization Purpose:

The purpose of this study was to test the efficacy of 3 months (90 days) once daily oral treatment with a clinical development candidate at 0.3 and 3 mg/kg/day for protection against 3000 Lux light damage in vivo using Wistar rats. Long term light damage (3 months) in rats has been shown to result in photoreceptor degeneration and choroidal neovascularization (CNV). Efficacy of an exemplary clinical development candidate in protecting against light induced ONL loss and CNV was evaluated.

Materials and Methods:

On the day prior to the start of dosing and once weekly for 13 weeks, the clinical development candidate was weighed into new empty glass scintillation vials. The clinical development candidate was dissolved in deionized water to a concentration necessary to achieve desired dose at the desired dose volume (0.5 mL/animal). The dosing solutions were stored at 4° C. and used for dose administration once per day for one week. The vehicle used for dosing control groups was deionized water. Sixteen Female Wistar rats (Charles River Laboratories) were used for this study. The animals were approximately 12 weeks at the initiation of dosing with an average body weight of 220 grams.

Assay:

Animals were dosed once daily in the morning (within 1 hour of light onset) orally, by gavage, with the assigned vehicle control or test articles using a 1 mL syringe fitted with a 20 gauge oral gavage needle. The animals were housed in cyclic light so that there was 12 hours of 3000 lux white light at the center of the cages alternating with 12 hours darkness. Upon the completion of the study animals were euthanized with carbon dioxide followed by creating pneumothorax. Immediately following the cervical dislocation both eyes of the animal were removed for analysis. The analyses consisted of staining of sections and flatmount analysis. The eye cups were fixed in 4% PFA for 1 hour at room temperature. One eye cup was processed for paraffin embedding, sectioned and stained with H&E or isolectin B4. The other eye was fixed for flat mounting. Flatmount eyes were dissected into the retina and choroid/sclera complex. Both the retina, choroid/sclera complex were stained with isolectin B4.

Study Design

| Treatment Designations and Animal Assignments Group | Treatment | Dose (mg/kg) | 3000 Lux exposure | No. of animals per group | Total |
|---|---|---|---|---|---|
| NC (1, 2) | Vehicle | NA | No | 2 | 4 |
| 3, 2 | Vehicle | NA | Yes | 2 | 4 |
| 5, 6 | ACU-4429 | 3 | Yes | 2 | 4 |
| 7, 8 | ACU-4429 | 0.3 | Yes | 2 | 4 |

NC = Normal light Control

Data Analysis:

Sections of the eye were examined by microscope after H&E staining and ONL area near the optic nerve was photographed at 40×10 magnifications for outer nuclear cell counts. The microscope photographs were printed on an 8"×11" paper. The numbers of ONL nuclei intersected by two vertical lines evenly dispersed on the picture were counted and average cell numbers represent the ONL thickness for that eye. Parafin sections were stained with isolectin B4 to determine if choroidal neovascularization was present. Isolectin B4 stains blood vessels. (See FIG. 16.) To quantify choroidal neovascularization the number of vessels crossing from the choroid and through the retina were counted per section and analyzed in Excel. The vessels were counted in 10-33 sections and data were reported as an average per animal. Since the flatmount data was inconclusive, it was excluded from this report.

Results

ONL Raw Count

| | Conditions | | | | | | | | | | | | | | | |
|---|---|---|---|---|---|---|---|---|---|---|---|---|---|---|---|---|
| | DC | | | | LC | | | | 4429.3 mg/kg | | | | 4429.03 mg/kg | | | |
| Animal # | 1 | 2 | 3 | 4 | 5 | 6 | 7 | 8 | 9 | 10 | 11 | 12 | 13 | 14 | 15 | 16 |
| count 1 | 8 | 7 | 11 | 10 | 1 | 2 | 0 | 1 | 2 | 1 | 1 | 1 | 0 | 0 | 1 | 1 |
| count 2 | 8 | 6 | 9 | 12 | 1 | 1 | 0 | 1 | 3 | 2 | 1 | 1 | 1 | 1 | 1 | 2 |
| count 3 | 10 | 9 | 10 | 9 | 1 | 0 | 1 | 1 | 1 | 2 | 2 | 1 | 0 | 1 | 1 | 2 |
| count4 | 10 | 9 | 10 | 9 | 1 | 0 | 1 | 2 | 3 | 2 | 2 | 1 | 0 | 1 | 1 | 1 |
| Average | 9.0 | 7.8 | 10.0 | 10.0 | 1.0 | 0.8 | 0.5 | 1.3 | 2.3 | 1.8 | 1.5 | 1.0 | 0.3 | 0.8 | 1.0 | 1.5 |
| Group average | | 9.2 | | | | 0.9 | | | | 1.6 | | | | 0.9 | | |

One-Way ANOVA

| Tukey's Multiple Comparison Test | Mean Diff. | q | P value |
|---|---|---|---|
| LC (Vehicle) vs DC | −8.325 | 25.25 | P < 0.01 |
| LC (Vehicle) vs 4429, 3 mg/kg | −0.750 | 2.275 | P > 0.05 |
| LC (Vehicle) vs 4429, 0.3 mg/kg | 0.00 | 0 | P > 0.05 |
| 4429, 0.3 mg/kg vs 3 mg/kg | −0.750 | 2.275 | P > 0.05 |

Figure 22:
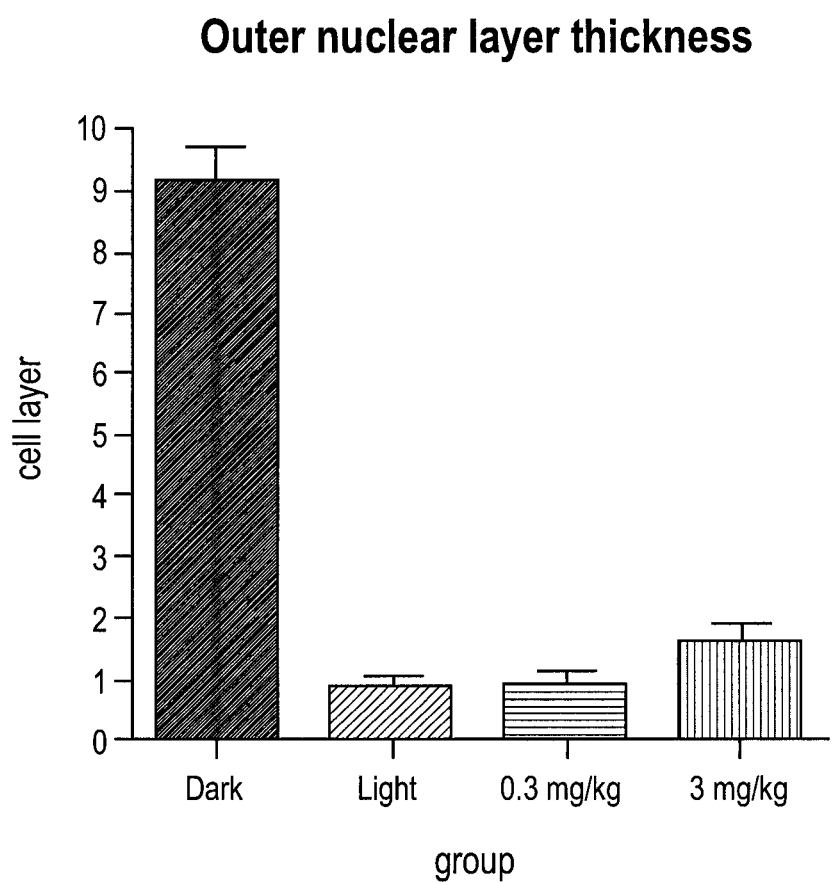
FIG. 22 is a graph depicting the number of rows of nuclei in the outer nuclear layer in H&E sections from animals treated with ambient light and 3000 lux plus vehicle or ACU-4429. Data are mean±SEM.

FIG. 22 illustrates the number of rows of nuclei in the outer nuclear layer in H&E section from animals treated with ambient light ant 3000 lux per vehicle or the clinical development candidate. Data are mean±SEM.

Raw Vessel Count

| | Conditions | | | | | | | | | | | | | | | |
|---|---|---|---|---|---|---|---|---|---|---|---|---|---|---|---|---|
| | DC | | | | LC | | | | | 3 mg/kg | | | 0.3 mg/kg | | | |
| Animal # | 1 | 2 | 3 | 4 | 5 | 6 | 7 | 8 | 9 | 10 | 11 | 12 | 13 | 14 | 15 | 16 |
| Vessel counts | 0 | 0 | 0 | 0 | 0 | 0 | 0 | 0 | 0 | 0 | 0 | 0 | 0 | 0 | 0 | 0 |
| | 0 | 0 | 0 | 0 | 2 | 2 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 1 | 0 | 0 | 0 | 0 |
| | 0 | 0 | 0 | 0 | 2 | 0 | 0 | 0 | 0 | 0 | 0 | 0 | 0 | 0 | 0 | 0 |
| | 0 | 0 | 0 | 0 | 1 | 2 | 1 | 0 | 0 | 0 | 0 | 0 | 0 | 0 | 0 | 0 |
| | 0 | 0 | 0 | 0 | 1 | 1 | 0 | 0 | 0 | 0 | 0 | 0 | 0 | 0 | 0 | 0 |
| | 0 | 0 | 0 | 0 | 0 | 1 | 0 | 0 | 0 | 0 | 1 | 0 | 0 | 0 | 0 | 0 |
| | 0 | 0 | 0 | 0 | 0 | 0 | 1 | 0 | 0 | 0 | 0 | 0 | 0 | 0 | 0 | 0 |
| | 0 | 0 | 0 | 0 | 0 | 1 | 2 | 0 | 0 | 0 | 0 | 0 | 0 | 0 | 0 | 0 |
| | 0 | 0 | 0 | 0 | 0 | 2 | 1 | 0 | 0 | 0 | 0 | 0 | 0 | 0 | 0 | 0 |
| | 0 | | 0 | 0 | 0 | 2 | 0 | 0 | 1 | 0 | 0 | 0 | 0 | 0 | 0 | 0 |
| | 0 | | 0 | 0 | 0 | 0 | 0 | 0 | 0 | 0 | 1 | 0 | 0 | 0 | 0 | 0 |
| | 0 | | 0 | 0 | 0 | 2 | 0 | 0 | 0 | 0 | 0 | 0 | 0 | 0 | 0 | 0 |
| | 0 | | 0 | 0 | 0 | 2 | 0 | 0 | 0 | 0 | 0 | 1 | 0 | 0 | 0 | 1 |
| | 0 | | 0 | 0 | 0 | 0 | 1 | 0 | 0 | 0 | 0 | 0 | 0 | 0 | 0 | 0 |
| | 0 | | 0 | 0 | 0 | 0 | 0 | 0 | 0 | 0 | 0 | 0 | 0 | 0 | 0 | 1 |
| | 0 | | 0 | 0 | 0 | 2 | 2 | 2 | 0 | 0 | 1 | 0 | 1 | 0 | 0 | 2 |
| | 0 | | 0 | 0 | 0 | 1 | 0 | 2 | 0 | 0 | 1 | 0 | 0 | 0 | 0 | 1 |
| | 0 | | 0 | 0 | 1 | 1 | 0 | 3 | 1 | 2 | 0 | 0 | 0 | 0 | 0 | 0 |
| | 0 | | 0 | 0 | 0 | 0 | 1 | 3 | 0 | 0 | 0 | 0 | 0 | 0 | 0 | 0 |
| | 0 | | 0 | 0 | 0 | 0 | 1 | 1 | 0 | 0 | 0 | 0 | 0 | 0 | 0 | |
| | 0 | | 0 | 0 | 0 | 0 | 1 | 1 | 0 | 0 | 1 | 0 | 0 | 0 | 0 | |
| | 1 | | 0 | 0 | 0 | 0 | 0 | 0 | 0 | 0 | 0 | 0 | 0 | 0 | 0 | |
| | 0 | | 0 | 0 | 0 | 0 | 0 | 0 | 0 | 2 | 1 | 0 | 0 | 0 | 0 | |
| | 0 | | 0 | | 0 | 0 | 0 | 0 | 0 | 0 | | 0 | 0 | 1 | 0 | |
| | 0 | | 0 | | 1 | 0 | 0 | | 0 | 0 | | 0 | 0 | 1 | | |
| | 0 | | 0 | | | 0 | | | 0 | 0 | | 0 | 0 | | | |
| | 0 | | | | | | | | 0 | 0 | | | 1 | | | |
| | 0 | | | | | | | | 0 | 0 | | | 0 | | | |
| | 0 | | | | | | | | | 0 | | | 0 | | | |
| | 0 | | | | | | | | | 0 | | | 0 | | | |
| | 0 | | | | | | | | | 0 | | | | | | |
| | 0 | | | | | | | | | | | | | | | |
| Average | 0.03 | 0 | 0 | 0 | 0.30 | 0.38 | 0.65 | 0.41 | 0.19 | 0.16 | 0.16 | 0.14 | 0.03 | 0.15 | 0 | 0.24 |
| Group average | 0.008 | | | | 0.437 | | | | | 0.162 | | | 0.104 | | | |

One-Way ANOVA

| Tukey's Multiple Comparison Test | Mean Diff. | q | P value |
|---|---|---|---|
| LC (Vehicle) vs. DC | 0.4296 | 9.046 | P < 0.01 |
| LC (Vehicle) vs. 4429, 3 mg/kg | 0.2755 | 5.801 | P < 0.01 |
| LC (Vehicle) vs. 4429, 0.3 mg/kg | 0.3328 | 7.008 | P < 0.01 |
| 4429, 0.3 mg/kg vs. 3 mg/kg | −0.0573 | 1.207 | P > 0.05 |

Figure 23:
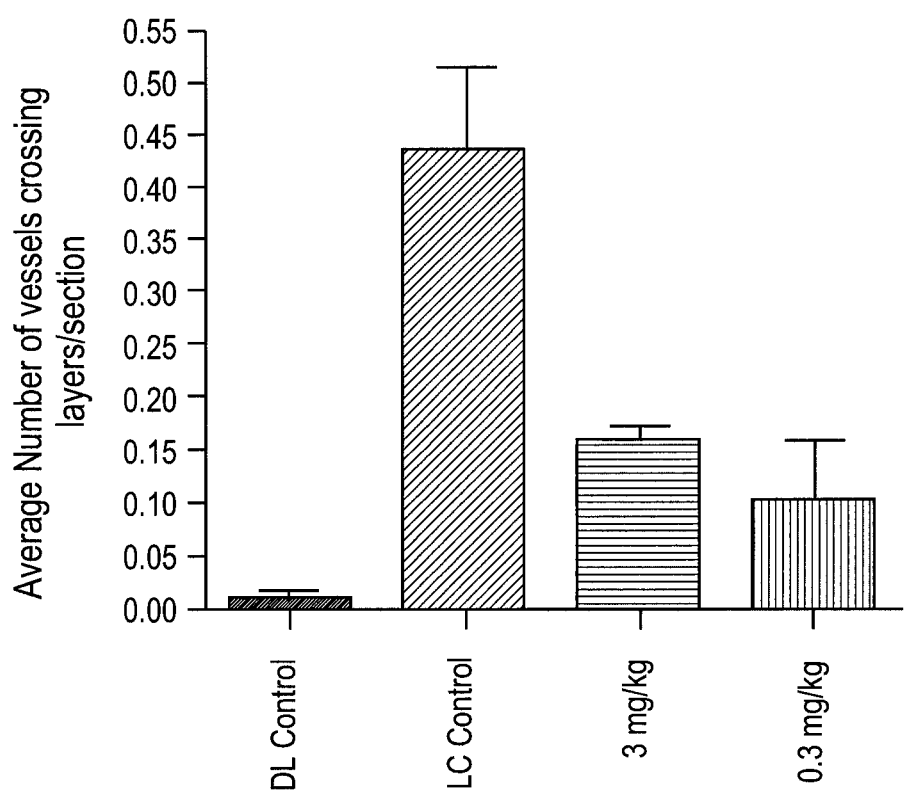
FIG. 23 is a graph depicting number of vessels crossing layers/sections.

FIG. 23 illustrates the number of vessels crossing layers/sections.

Conclusions:

The clinical development candidate protects the retina from light induced ONL thinning. The treatment with the clinical development candidate provided significant protection against choroidal neovascularization.

Example 8: Phase I Dose-Ranging Study of ACU-4429, a Novel Visual Cycle Modulator, in Healthy Volunteers Visual Cycle Modulation (VCM) refers to the biological conversion of a photon into electrical signal in the retina. (See, e.g., FIGS. 4A and 4B)

The retina contains light-receptor cells known as "rods" (responsible for night vision) and "cones" (responsible for day vision). Rod cells are much more numerous and active than cones. Rod over-activity creates the build-up of toxins in the eye, whereas cones provide the vast majority of our visual information—including color. The VCM essentially "slows down" the activity of the rods and reduces the metabolic load on the cones.

Isomerase/RPE65 represents one target for inhibition as it is specific to the visual cycle. Rod cells are the major source of A2E (90% of photoreceptor cells)

A2E Toxicities:

Free radical generation upon light exposure;
Detergent-like properties can damage RPE cell membrane;
Inhibits RPE lysosomes (leads to drusen formation); and
Activation of complement factors.

ACU-4429 was designed to prevent or inhibit the generation of toxic by-products of the visual cycle, which can lead to degenerative eye conditions. It is administered to patients as an oral, daily pill rather than by injection into the eye. Preclinical data indicate that ACU-4429 slows the rod visual cycle.

Phase 1 Data:

Safety and tolerability was observed in healthy volunteers aged 55-80. A dose-dependent modulation of visual cycle was observed by electroretinography (ERG).

Clinical Safety and Tolerability 125 healthy subjects were dosed with ACU-4429. It was well tolerated in these healthy subjects with no AEs of concern to DMC. Headaches were seen in some subjects, but were transient and could be unrelated to drug. Mild and transient visual AEs were observed. ACU-4429 produced a very good pharmacological response even at lower doses. No changes in cone ERGs were observed.

Overall, ACU-4429 has oral bioavailability. There was a linear correlation between dose and AUC and $C_{max}$ and a steady state is reached after the first dose. A dose dependent decrease in ERG b-wave amplitude was observed.

Figure 6:
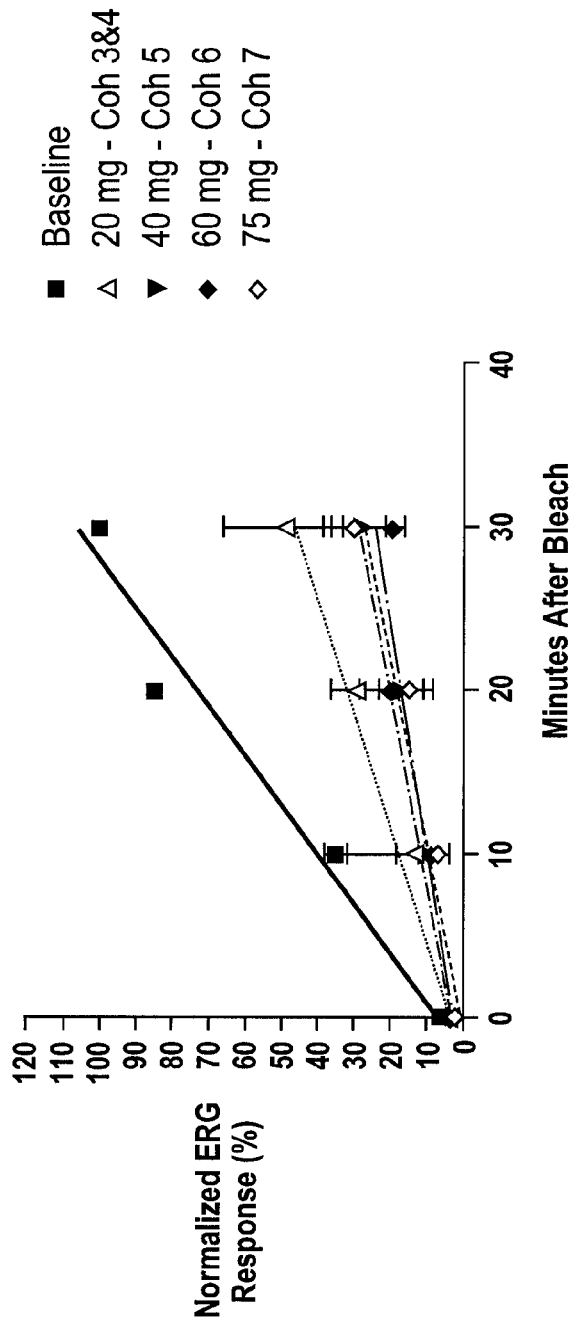
FIG. 6 is a graph depicting ACU-4429 Phase 1a Rod ERG Suppression.
Figure 7:
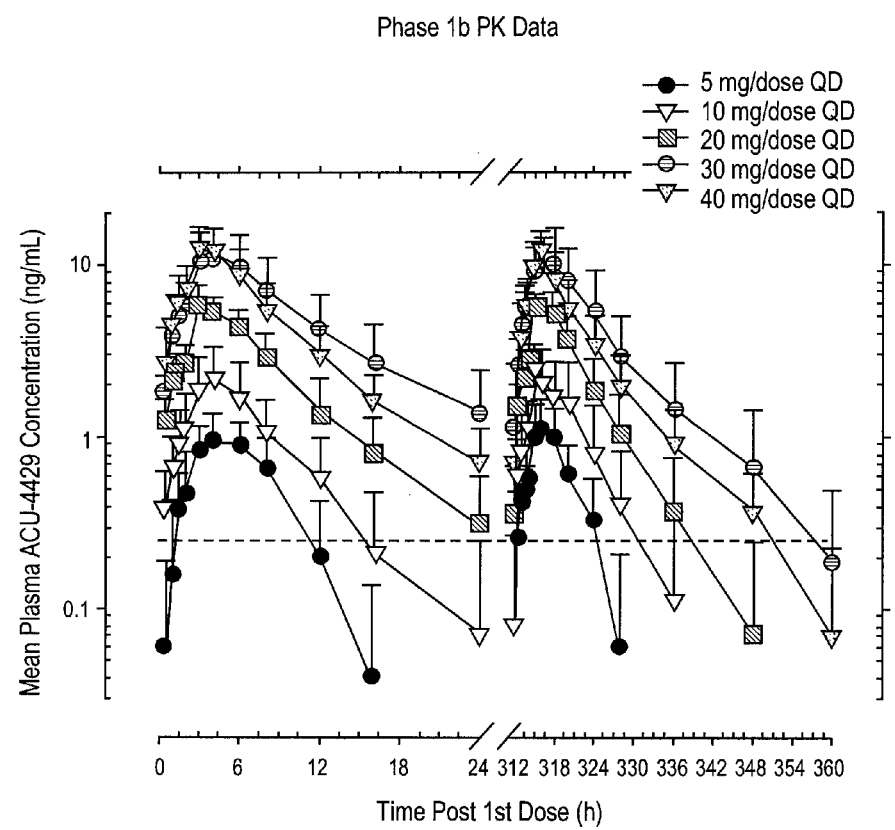
FIG. 7 is a graph depicting Phase 1b PK Data.

AUC increased approximately proportionally with dose, therefore systemic exposure can be easily adjusted in the clinic with increase or decrease of oral dose of ACU-4429. Maximal plasma concentration ($C_{max}$) also increased linearly with dose. ACU-4429 was readily absorbed from the GI tract. (See FIG. 7.) ACU-4429 Phase 1a Rod ERG Suppression (24 h) is illustrated in FIG. 6.

| Dose | Suppression |
| --- | --- |
| 20 mg | 29% ± 35% |
| 40 mg | 86% ± 10% |
| 60 mg | 93% ± 4% |
| 75 mg | 98% ± 1% |

Phase 1b Study Design

| | |
| --- | --- |
| Study Design | Single-center, randomized, double-masked, placebo-controlled, multi-dose escalating study |
| Objective | Assess safety, tolerability, and pharmacokinetics (PK) |
| Dose | Five cohorts, randomized 6:2<br>5, 10, 20, 30, 40 mg<br>14 days per cohort |
| Endpoints | Safety, tolerability, and PK |
| Major Inclusion Criteria | Healthy volunteers of both genders, aged 55-80, weight ≥50 and ≤110 kg |
| Major Exclusion Criteria | Ocular conditions (cataracts, glaucoma, uveitis, diabetic retinopathy, and active conjunctivitis)<br>Change in prescription chronic medications within 28 days<br>Treatment in the past year with a retinoid compound<br>Treatment within the last week with Viagra ®, Cialis ®, Levitra ®<br>Concomitant treatment with hypnotics, anti-depressants and psychoactive substances; digitalis glycosides (digoxin, ouabain, digitoxin); L-DOPA; chloroquine or hydroxychloroquine; systemic corticosteroids; topical anti-glaucoma medications; medications for treatment of "wet" AMD |

Phase 1b—Demographics

| | ACU-4429<br>N = 30 | Placebo<br>N = 10 |
| --- | --- | --- |
| Age, mean (SD) | 39.8 (8.48) | 37.7 (8.55) |
| Male, n (%) | 22 (73.3%) | 8 (80%) |
| Race, n (%) | | |
| White | 25 (83.3%) | 5 (50.0%) |
| Black or African American | 5 (6.7%) | 3 (30%) |
| Asian | 0 | 1 (10%) |
| Other | 0 | 1 (10%) |

Phase 1b—Summary Adverse Events

| Cohort | Number of subjects with visual AEs | Number of visual AEs |
| --- | --- | --- |
| 5 mg | 0 | 0 |
| 10 mg | 2 | 21* |
| 20 mg | 6 | 29 |
| 30 mg | 6 | 26 |
| 40 mg | 6 | 33 |

*1 subject had 19 visual AEs; all visual adverse events were mild.

Phase 1b PK Data $C_{max}$ was approximately 4 hours after $1^{st}$ and last dose; PK parameters similar to Phase 1a study; and levels reached a steady state after $1^{st}$ dose. (See FIG. 7).

Figure 8:
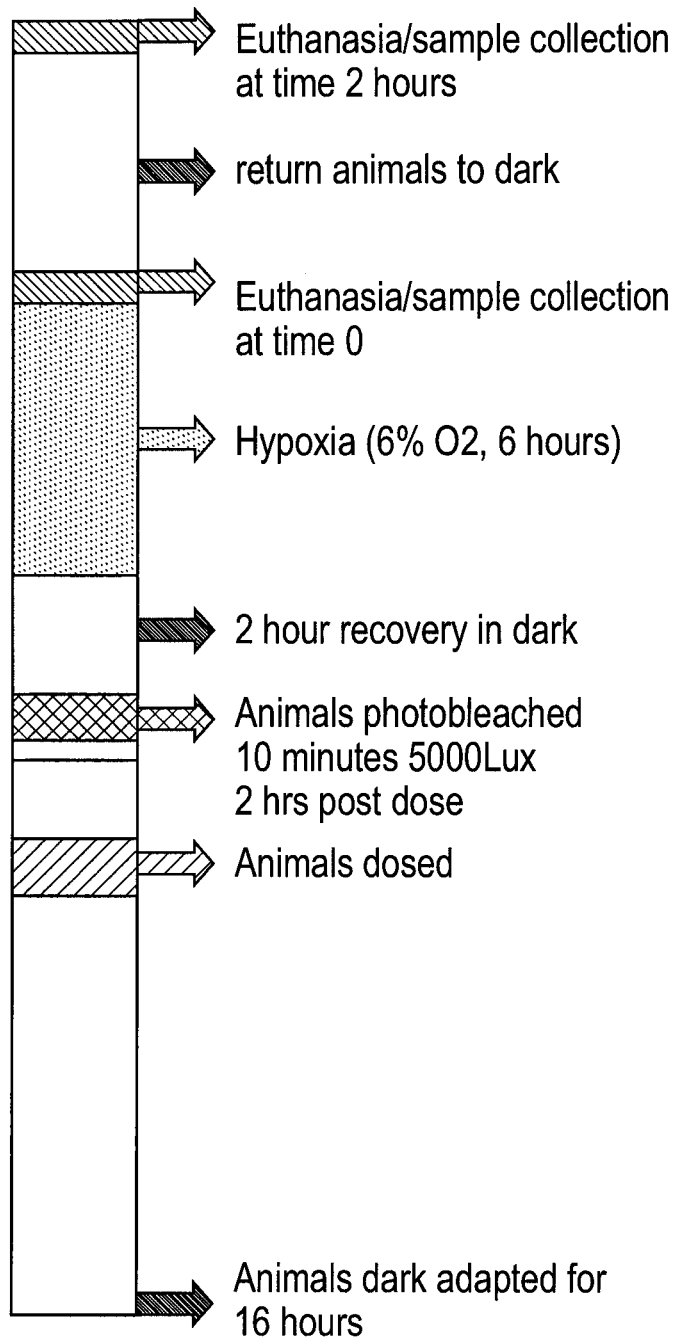
FIG. 8 provides the timeline for an experiment to test if ACU-4935 reduced VEGF up-regulation caused by hypoxic conditions.

Example 9: Experiment to Test if ACU-4935 Reduced VEGF Up-Regulation Caused by Hypoxic Conditions FIG. 8 depicts a protocol used to test if ACU-4935 reduced VEGF up-regulation caused by hypoxic conditions. Briefly, animals were adapted for dark for 16 hours, then dosed with ACU-4935. Animals were photobleached for 10 minutes with 50000 Lux 2 hours after being dosed, followed by a 2 hour recovery in the dark. Hypoxia was induced with 6% $O_2$ for 6 hours. A portion of the animals were euthanized and samples were collected at time 0. Another portion of the animals were returned to the dark for 2 more hours prior to being euthanized and sample collection.

Figure 9:
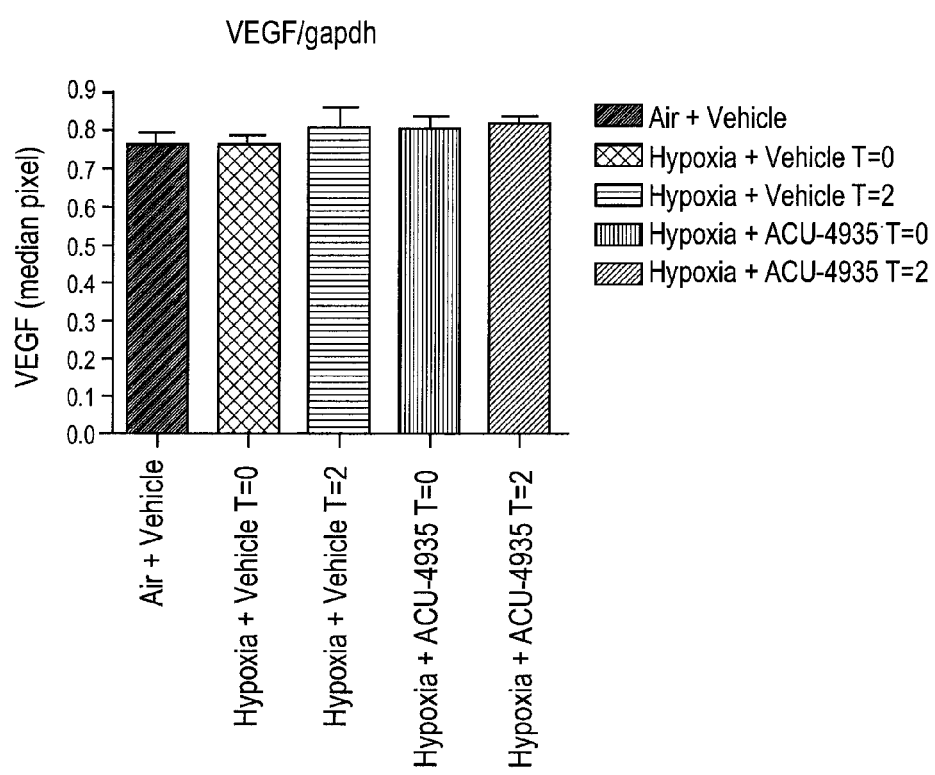
FIG. 9 is a graph illustrating VEGF Protein Expression caused by hypoxic conditions after treatment with ACU-4935.
Figure 10:
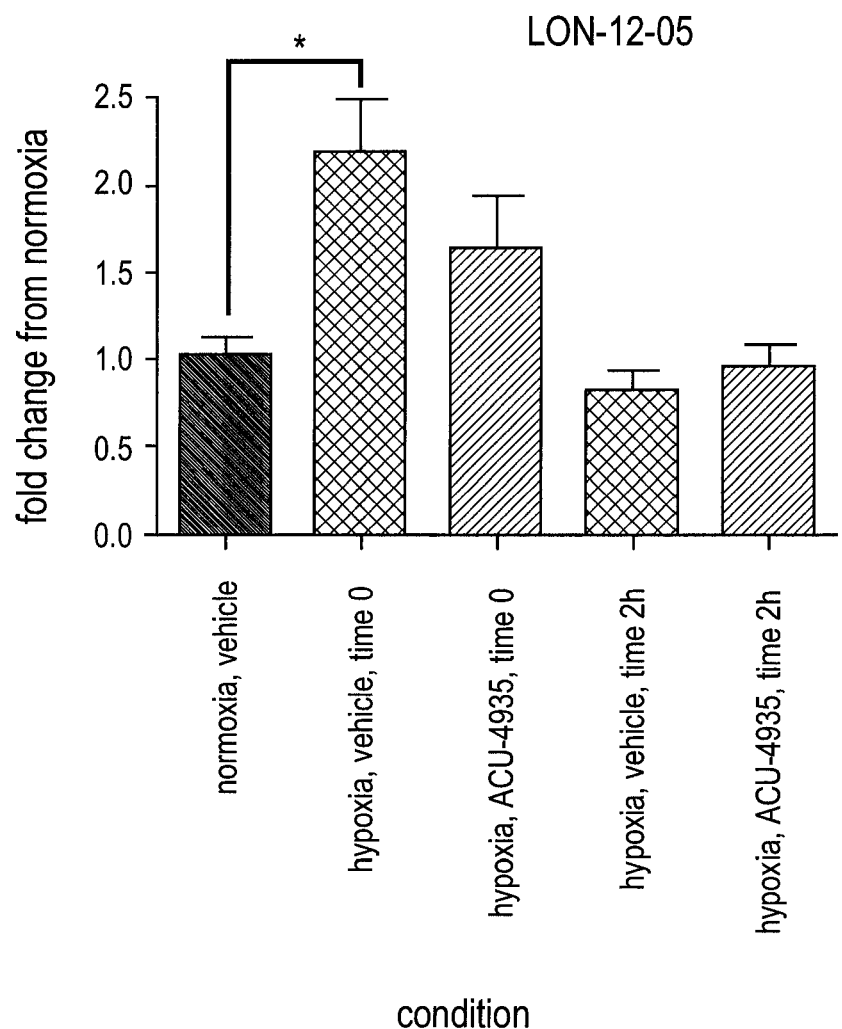
FIG. 10 is a graph illustrating VEGF mRNA levels caused by hypoxic conditions after treatment with ACU-4935.

Samples were tested for VEGF protein (FIG. 9) and mRNA expression (FIG. 10). Slight differences were observed in VEGF protein expression following treatment with ACU-4935. VEGF mRNA levels were decreased at time 0 and slightly increased 2 hours post-hypoxia following treatment with ACU-4935 compared to the vehicle control.

Example 10: Ocular Distribution of [14C]-ACU-4429 in Beagle Dogs

ACU-4429 ($C_{16}H_{25}NO_2$.HCl) is an oral visual cycle modulator which has been shown to reduce the activity of the rod visual system, thereby alleviating the metabolic load on the retina.

The following experiment was conducted to examine the pharmacokinetic profile, ocular distribution, and excretion of ACU-4429 and its metabolites in male beagle dogs after single and repeated oral doses of 0.3 mg/kg of [$^{14}$C]-ACU-4429 (40 μCi/kg).

[$^{14}$C]-ACU-4429 (0.3 mg/kg, 40 μCi/kg) as a powder in capsule was administered as a single oral dose or repeated doses (once daily for 7 days) to a total of 36 male beagle dogs that were not fasted. Mass balance was assessed through 168 hours after a single dose or through 336 hours after the first daily dose; urine and feces were analyzed for radioactivity and metabolic profiling. Blood was collected at 0.25, 1, 2, 4, 8, 12, 48, 72, 96, 168 and 192 hours following the final dose; blood and plasma were analyzed for radioactivity and plasma for metabolic profiling. Eye tissues (choroid, iris-capillary body, and RPE) were collected at 4, 8, 12, 24, 48, 72, and 168 hours after the final dose (3 animals/time point) and analyzed for radioactivity (right eyes) or metabolic profiling (left eyes).

In beagle dogs, orally administered [$^{14}$C]-ACU-4429 was readily absorbed ($T_{max}$=4 hours) and eliminated from plasma; the majority of radioactivity was not preferentially associated with RBCs. Radioactivity was rapidly eliminated through urine and feces (46% and 44%, respectively), and clearance from plasma was essentially complete by 48 hours post-dose. Other data indicated ACU-4429 parent molecule was preferentially distributed to melanin-containing ocular tissues, including the proposed site of VCM action, the RPE, in spite of rapid systemic clearance (See, FIGS. 11 and 12).

Figure 11A:
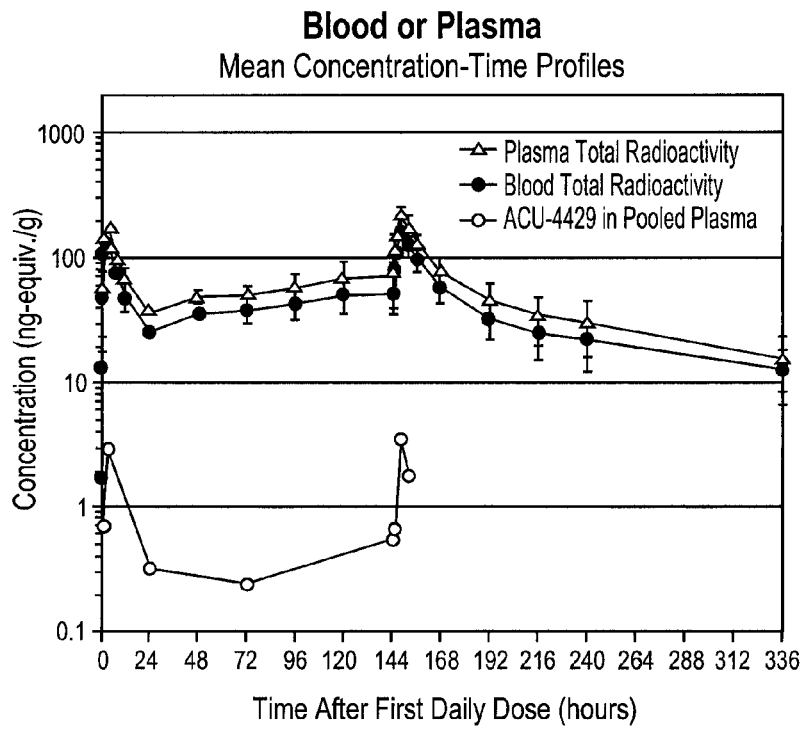
FIGS. 11A-11B: Mean Concentration Time Profiles for Blood or Plasma (FIG. 11A) or in Eye Tissue (FIG. 11B).
Figure 11B:
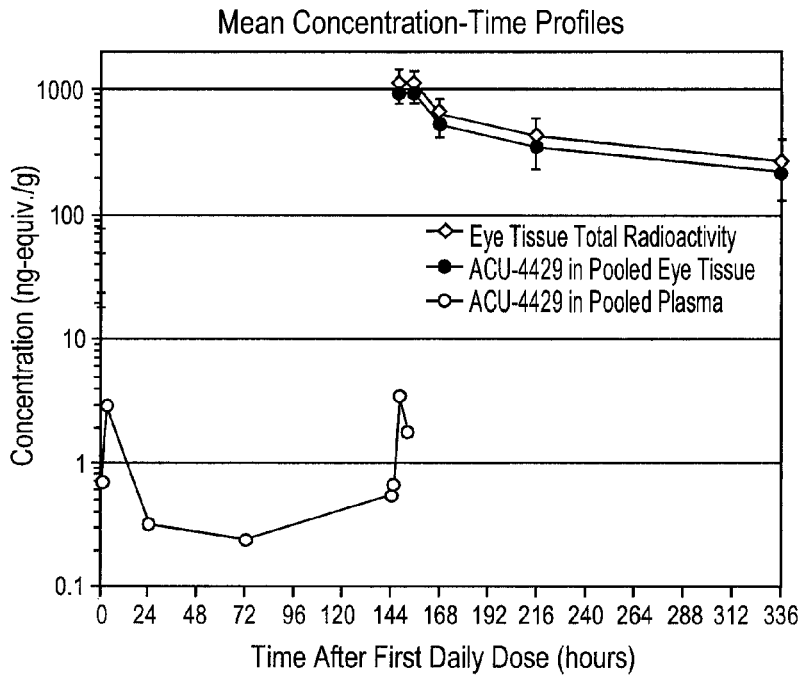
Figure 12A:
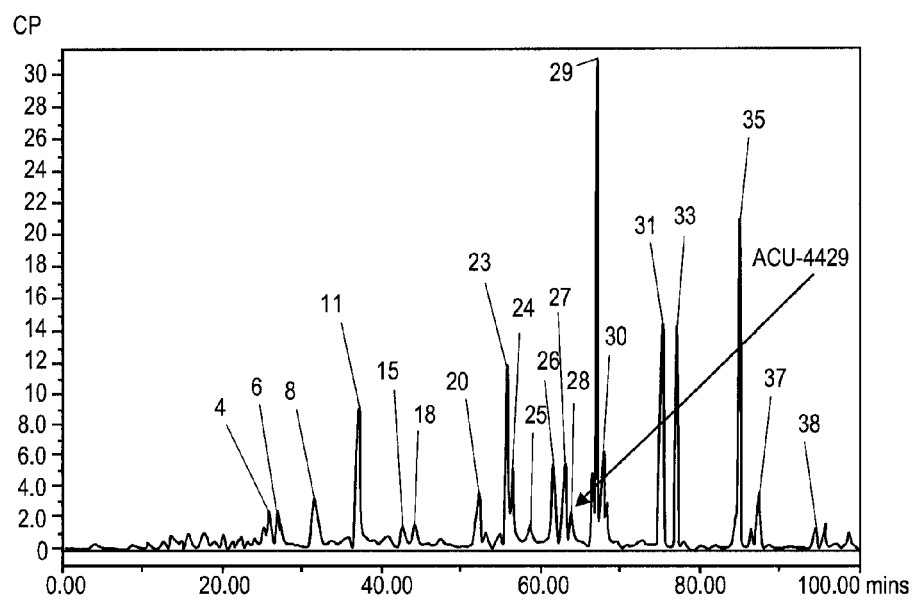
FIGS. 12A-12B: Metabolite radioprofiles at 4 hours post-dose on day 7 as described in Example 10.
Figure 12B:
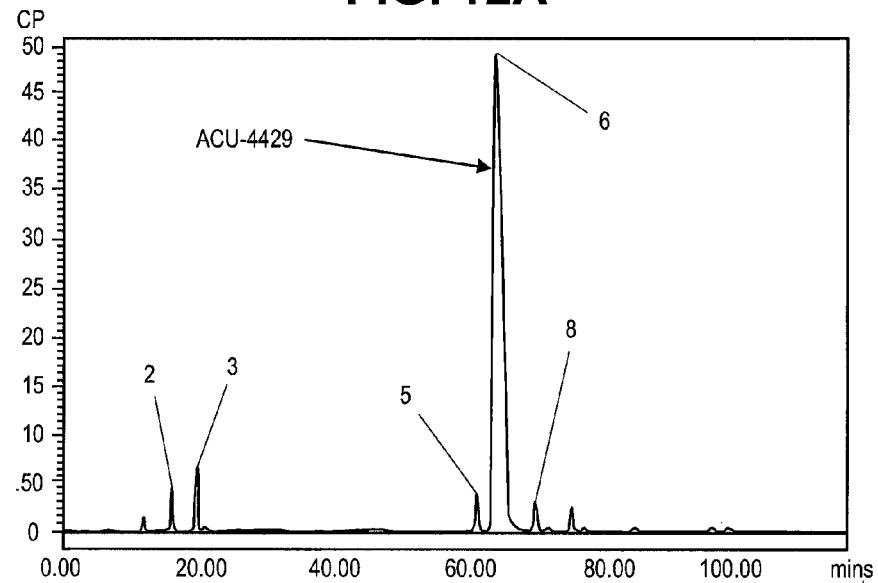
Figure 13:
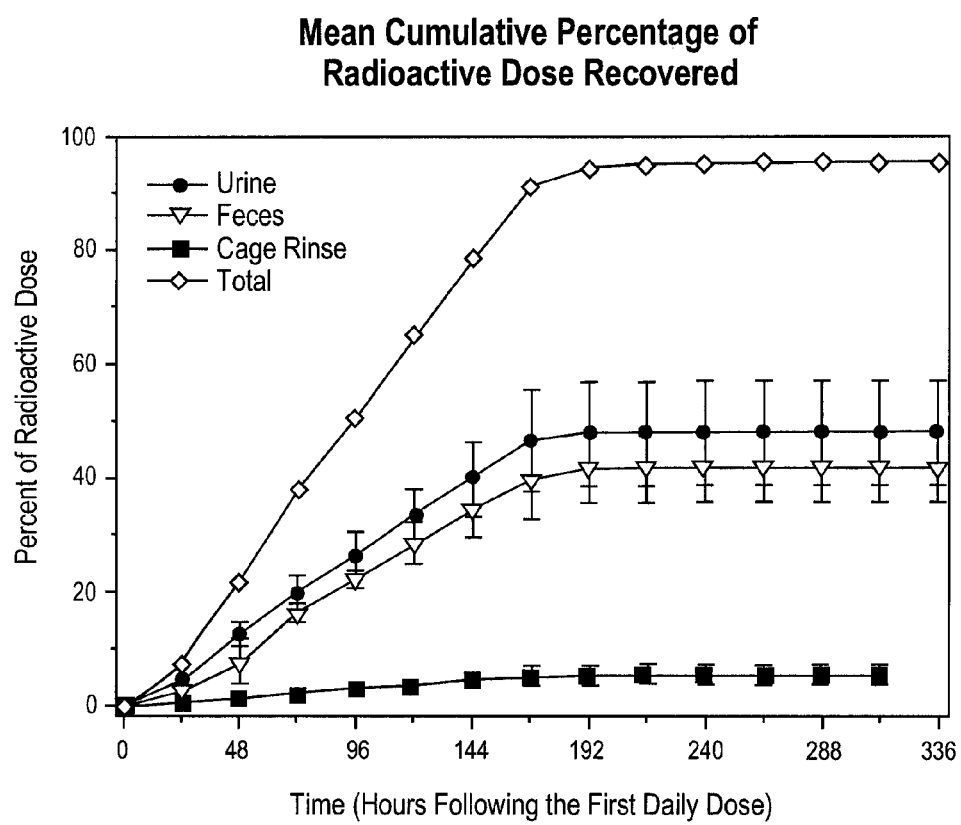
FIG. 13 is a graph illustrating mean cumulative percentage of radioactive dose recovered as described in Example 10.

In eye tissues, ACU-4429-$C_{max}$ was 278-fold higher than in plasma (930 vs. 3.34 ng-eq/g) after 7 consecutive days of oral dosing (FIG. 11).

REFERENCES

[1] Kubota et al., Retina, 2012, 32(1): 183-188.
[2] Sparrow et al., Vision Res., 2003, 43(28): 2983-2990; Travis et al., Ann. Rev. Pharmacol. Toxicol., 2007:47:469-512.

Example 11: VCMs as Inhibitors of Retinal Neovascularization

Under dark conditions, ion channels in the retina are open, allowing excess ions to flow into retinal cells. The retina requires energy and oxygen to pump out the excess flow of ions. Under normal healthy conditions, the blood supply to the retina is just barely sufficient to support this process, which produces more heat and consumes more oxygen than any function in other cells. If the blood supply is compromised, as often occurs in patients with diabetes, hypoxia can develop in the retina. The retina creates new, small, leaky vessels to compensate, leading to the proliferative diabetic retinopathy.

Figure 14:
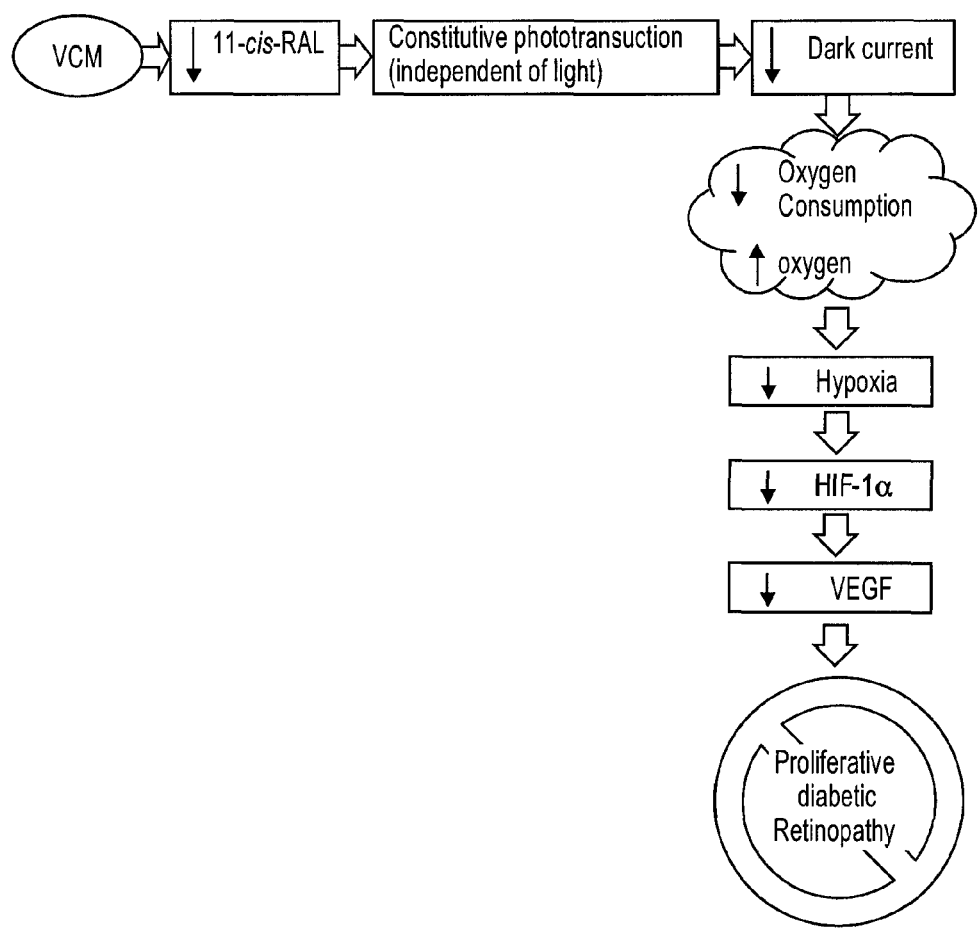
FIG. 14: Visual cycle modulators (VCMs), such as ACU-4420 and ACU-4935, inhibit the visual cycle isomerase, thereby mimicking a state of constitute phototransduction and decreasing the dark current.

Visual cycle modulators (VCMs), such as ACU-4420 and ACU-4935, inhibit the visual cycle isomerase, thereby mimicking a state of constitute phototransduction and decreasing the dark current (see FIG. 14). Without being bound by theory, it is believed that decreasing the dark current will reduce metabolic strain and associated oxygen requirements in the retina, which should reduce hypoxia, production of hypoxic inducible factor 1 (HIF-1α) and vascular endothelial growth factor (VEGF), and result in inhibition of new vessel growth.

This study evaluated the effects of the VCMs ACU-4429 and ACU-4935 on retinal neovascularization in a mouse model of oxygen-induced retinopathy (OIR).[3-5]

Figure 15:
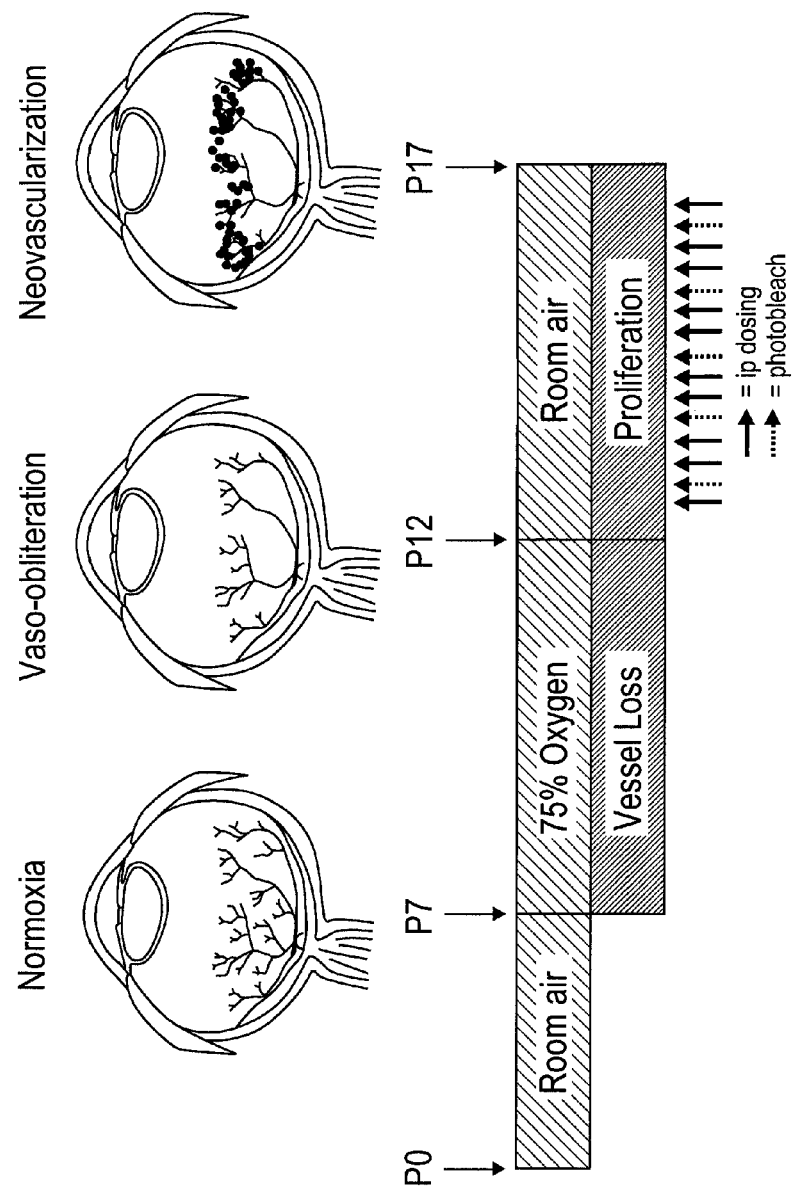
FIG. 15: Illustrates the protocol for treatment of 129 SvE mouse pups (PO) with ACU-4420 and ACU-4935.
Figure 16A:
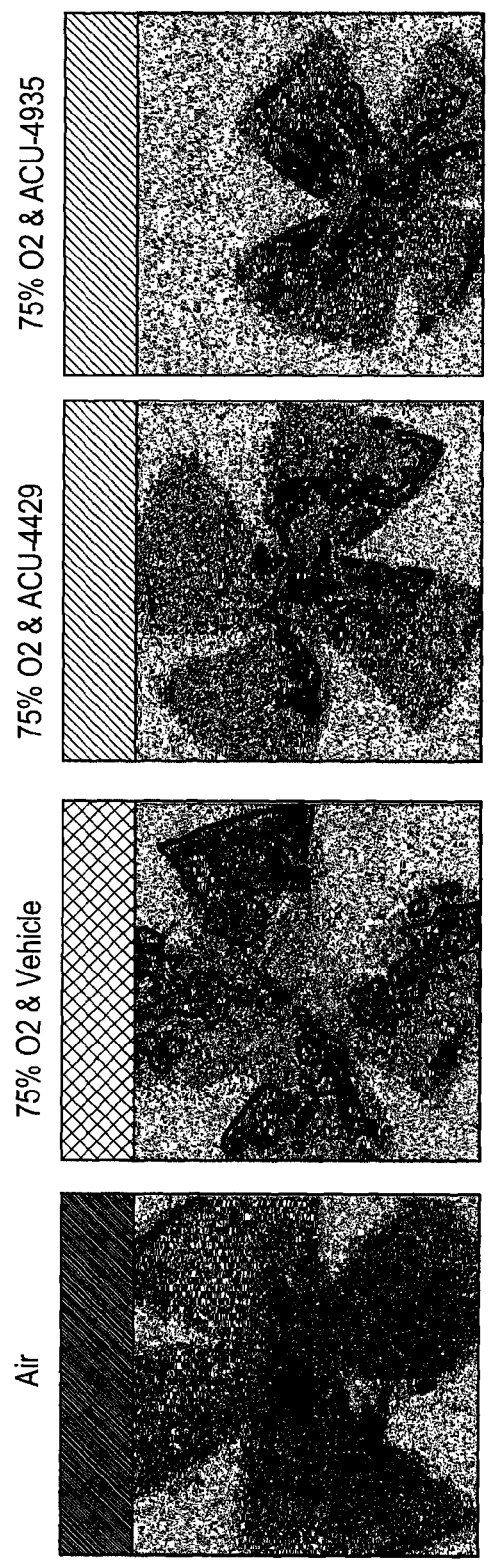
FIGS. 16A-16B demonstrate that VCMs inhibit neovascularization.
Figure 16B:
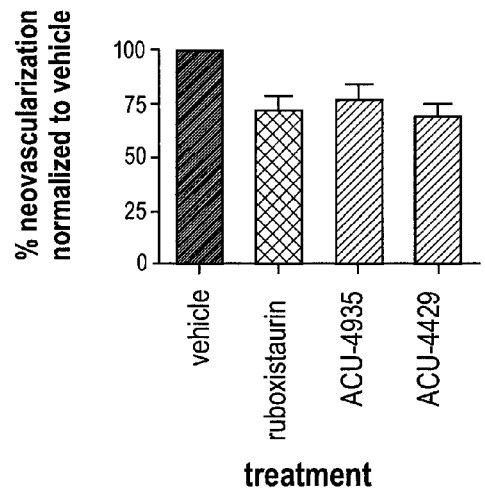
Figure 16C:
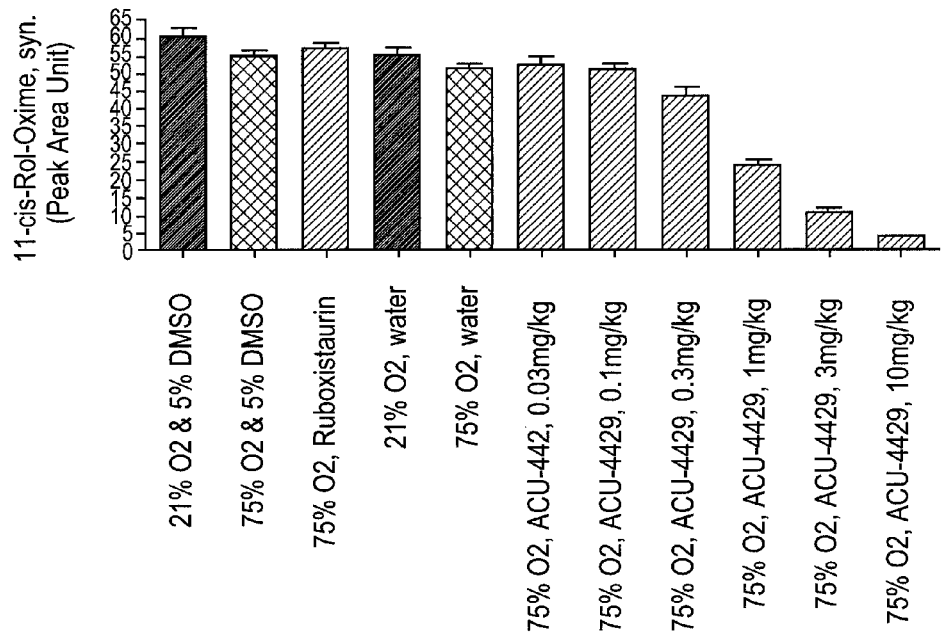
FIGS. 16C-16F demonstrate that ACU-4429 inhibited neovascularization and 11-cis-RAL in a dose-dependent manner.
Figure 16D:
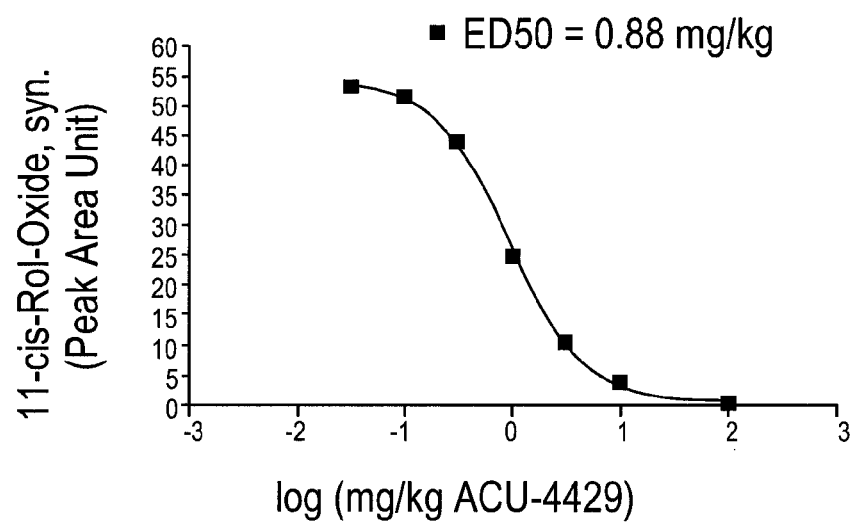
Figure 16E:
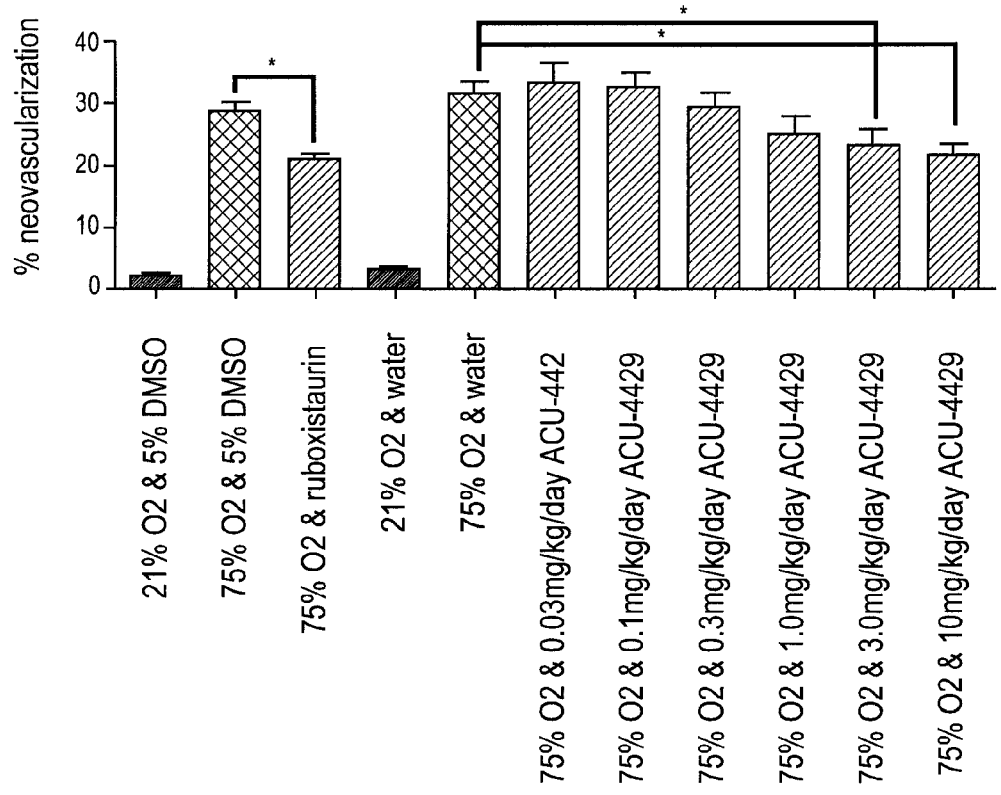
Figure 16F:
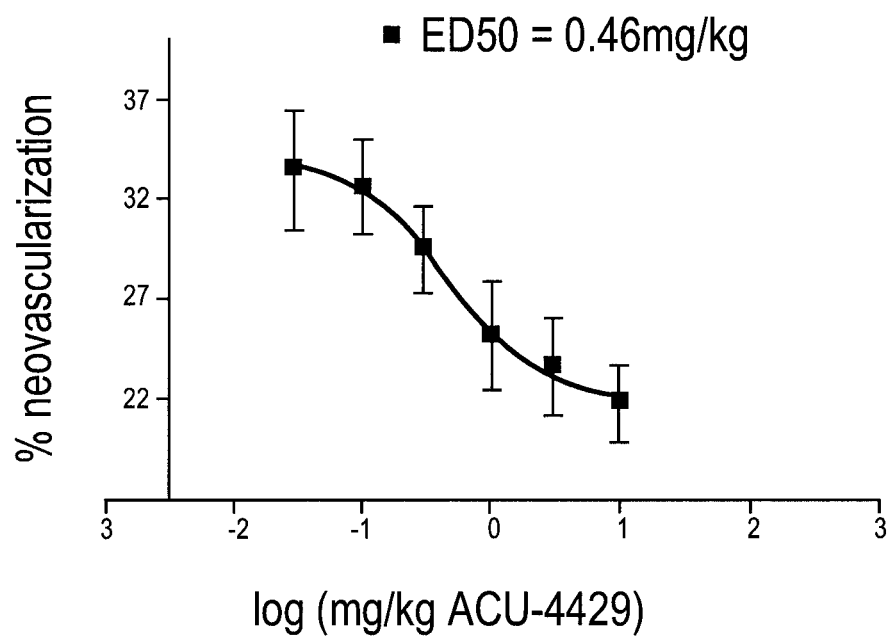
Figure 17:
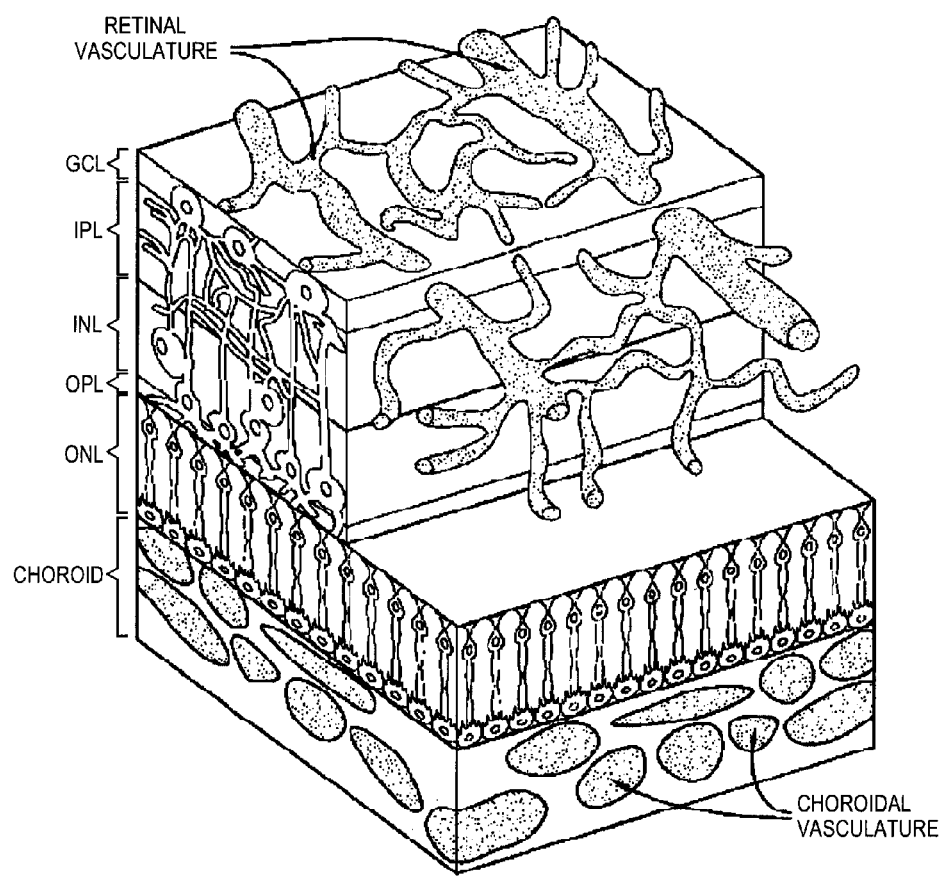
FIG. 17 is a diagram of the neural retina and its vascular supplies (not to scale). The layers of the neural retina (ganglion cell, inner plexiform, inner nuclear, outer plexiform, outer nuclear) are indicated. Blood flow through the choroidal vessels is swift. The retinal vasculature, visible by ophthalmosocopy, lies among the ganglion cells on the vitreal surface of the retina and extends capillary networks deep into the post-receptor layers. The caliber of the retinal arterioles adjusts to perturbations in blood oxygen levels ("autoregulation").
Figure 18:
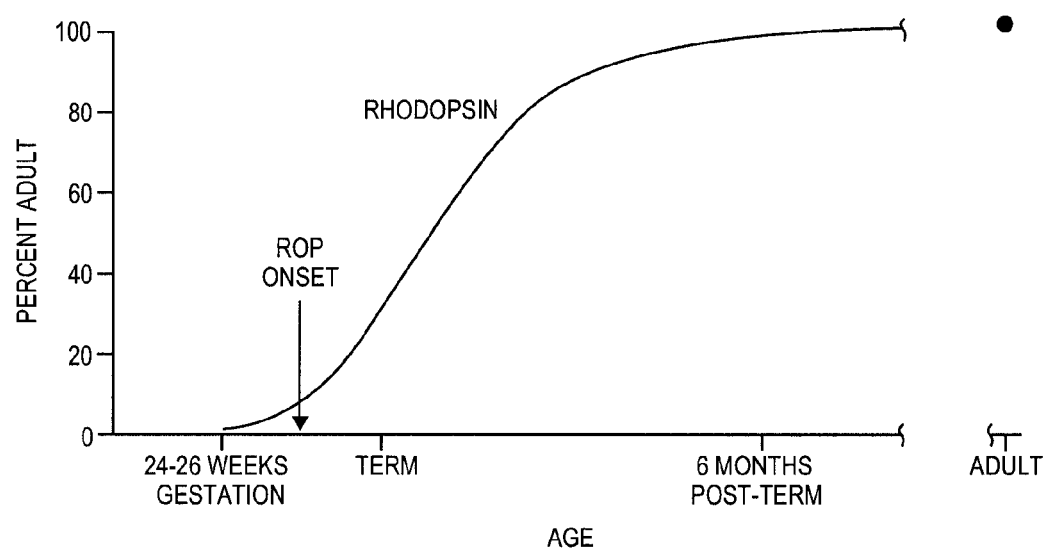
FIG. 18 illustrates logistic growth curve showing human rhodopsin content (Fulton et al., *Invest. Ophthalmol. Vis. Sci.*, (1999) 40: 1878-1883) as a function of age. The arrow indicates the age of ROP onset in preterm infants (Palmer et al. *Ophthalmology*, (1991) 98:1628-1640).

129 SvE mouse pups (PO) were treated as diagrammed in FIG. 15. ACU-4429 (0.03 to 10 mg/kg), ACU-4935 (0.3 mg/kg/day), positive controls (10 mg/kg/day Ruboxistaurin) or vehicle was administered intraperitoneally twice for 4 days.

Parameters for ACU-4429 and ACU-4935

| VCM | Chemical formula | $IC_{50}$ (in vitro isomerase activity) | $ED_{50}$ (in vivo isomerase assay single dose, mice) |
| --- | --- | --- | --- |
| ACU-4429 | $C_{16}H_{25}NO_2 \cdot HCl$ | 4.4 nM | 0.18 mg/kg |
| ACU-4935 | $C_{17}H_{29}NO_2$ | 5.2 nM | 0.0004 mg/kg |

Pups were euthanized on P17, when neovascularization was maximal and eyes were removed for analysis. When retinoids were to be extracted, mice were moved to a dark room on P16 and euthanized under a red light.

Areas of retinal neovascularization were visualized with isoelectin staining of flatmount preparations and quantified with the lasso tool in Adobe Photoshop; total area of neovascularization indicated the sum of individual areas across the retina, and % neovascularization was relative to the total area of the retina[4]. Retinoids were extracted from right eyes under red light and analyzed for 11-cis-ROL-oxime content to indicate 11-cis-ROL concentrations and as an indicator of cycle isomerase activity.

Statistical analyses were performed using GraphPad Prism software.

In mice with OIR, treatment with either ACU-4420 or ACU-4935 significantly reduced retinal neovascular area compared to treatment with vehicle. Retinal neovascular area was reduced by 32% with ACU-4429 (3 mg/kg/day), 23% with ACU-4935 (0.3 mg/kg/day), and 29% with Ruboxistaurin (10 mg/kg/day, positive control); the mean reduction was significantly (p<0.05) greater than with vehicle with both of the VCMs and did not differ significantly (p<0.05) from Ruboxistaurin.

ACU-4429 inhibited neovascularization and production of 11-cis-RAL in a dose dependent manner with ED50 values of 0.46 mg/kg and 0.88 mg/kg, respectively.

REFERENCES

1. Arden et al., Br. J. Opthalmol., 2005; 89(6): 764-769.
2. Kubota et al., Retina, 2012; 32(1): 183-188.
3. Chan et al., Lab. Invest., 2005; 85(6): 721-733.
4. Connor et al., Nat. Protoc., 2009; 4(100: 1565-1573.
5. Yoshida et al., FASEB J., 2010; 24(6): 1759-1767.

Example 12: Electroretinography Materials and Methods

Calibration of Light Flashes

ERG stimuli are delivered using an Espion $e^2$ with ColorDome Ganzfeld stimulator (Diagnosys LLC, Lowell, Mass.). The rate of photoisomerization per rod (R*) for the green LED flash is calculated by measuring the flux density incident upon an integrating radiometer (IL1700; International Light, Newburyport, Mass.) positioned at the location of the rat's cornea, and following the procedures detailed by Lyubarsky and Pugh (1996). The LED is treated as monochromatic with 1 equal to 530 nm. The intensity of the flash is given by $$i(\lambda) = Q(\lambda) \cdot T(\lambda) \cdot \frac{a_{pupil}}{a_{retina}} \cdot a_{rod}(\lambda) \tag{1}$$

where $i(\lambda)$ is R*, $Q(\lambda)$ is the calculated photon density at the cornea, $T(\lambda)$ is the transmissivity of the ocular-media and pre-receptor retina (~80% at 530 nm; Alpern et al., 1987), and $a_{pupil}$, $a_{retina}$ and $a_{rod}(\lambda)$ are respective estimates of the area of the dilated pupil~$mm^2$; Dodt and Echte, 1961), the area of the retinal surface (~50 $mm^2$; Hughes, 1979), and the end-on light collecting area of the rod photoreceptor (~1.5 $mm^2$ at 530 nm). $a_{rod}(\lambda)$ takes into account the length of the outer segment, the absorption spectrum of the rod, and the optical density of the photopigment, as well as the radius of the photoreceptor (Baylor et al., 1979). Since several of these parameter values are unknown for the rat rod that is affected by OIR, stimuli are expressed as the expected values in adult control rats. $Q(\lambda)$ is found by $$Q(\lambda) = \lambda \cdot \frac{P_\lambda}{h \cdot C} \tag{2}$$

where Pλ is the radiant flux (W), h is Plank's constant and c is the speed of light (Wyszecki and Stiles, 1982). To evaluate the intensity of 'white' xenon-arc flashes, an intensity series with interspersed green and white flashes is recorded and the equivalent light is estimated based on the shift of the stimulus/response curves for the scotopic b-wave.

Calibration of the Bleaching Light

The bleach is produced using an Ektagraphic III B slide projector (Eastman Kodak, Rochester, N.Y.) with an EXR 300 W halogen lamp (color temperature 3350°). To diffuse the light, a hemisected Ping-Pong ball is placed over the eye. The projector is positioned on a platform so that its lens is approximately 6 cm from the surface of the ball. The power of the light is measured using the radiometer, with the integration feature turned off, positioned under the Ping-Pong ball at the location of the rats' head. The calculation of the number of photons incident upon the photodetector (quanta cm$^{-2}$ s$^{-1}$) is calculated using eq. (2) and assuming λ=500 nm. The strength of the bleach is estimated by $$R_0(t) = \exp\left(-\frac{Q(\lambda) \cdot t}{Q_e}\right) \quad (3)$$

where 1−R$_0$ is the fraction of rhodopsin bleached at the termination of the light exposure, t is the duration (60 s) of the exposure, and Q$_e$ (quanta cm$^{-2}$), the inverse of photosensitivity, is the energy needed to leave 1/e of rhodopsin unbleached (Perlman, 1978). Earlier measurements indicate that the value of Q$_e$ in Sprague Dawley rats is approximately 15.8 log quanta cm$^{-2}$ (Fulton and Baker, 1984). Thus, the light, which produces approximately 15.9 log quanta cm$^{-2}$, bleached ~60% of the rhodopsin in the retina.

Preparations

Dark-adapted subjects are anesthetized with a loading dose of approximately 75 mg kg$^{-1}$ ketamine and 8 mg kg$^{-1}$ xylazine, injected intraperitoneally. This is followed by a booster dose (50% of loading dose) administered intramuscularly. The pupils are dilated with a combination of 1% phenylephrine hydrochloride and 0.2% cyclopentolate hydrochloride (Cyclomydril; Alcon, Fort Worth, Tex.). The corneas are anesthetized with one drop of 0.5% proparacaine hydrochloride. A Burian-Allen bipolar electrode (Hansen Laboratories, Coralville, Iowa) is placed on the cornea and the ground electrode is placed on the tail. The red light is extinguished, and the animals remain in total darkness for an additional 10 min to allow them to return to a fully dark-adapted state before experimentation commences.

The Activation of Phototransduction

At the first test date, animals are assigned half-hazard such that half of each litter (rounded up if odd in number) participates in studies of the activation and deactivation of phototransduction, and of post-receptor retinal function; the remainder participate in the bleaching experiments. Characteristics of the rod photoresponse are estimated from the ERG by fitting the parameters of the Hood and Birch (1992) formulation of the Lamb and Pugh (1992; Pugh and Lamb, 1993) model of the biochemical processes involved in the activation of phototransduction to the a-waves elicited by the five brightest flashes:

$$P_3(i,t) = Rm_{P3} \cdot (1 - \exp(-\tfrac{1}{2} \cdot i \cdot S \cdot (t - t_d)^2)) \quad 4$$

for t$_d$<t<20 ms.

In this model, i is the intensity of the flash (R*) and t is elapsed time (s). The values of the free parameters in the model, Rm$_{P3}$, S, and t$_d$, are optimized using a routine (fmins; MATLAB R11, The Math-works, Natick, Mass.) that minimizes the sum of squared deviates. Rm$_{P3}$ is the amplitude (μV) of the saturated rod response; it is proportional to the magnitude of the dark current and depends upon the number of channels available for closure by light in the ROS (Lamb and Pugh, 1992; Pugh and Lamb, 1993), which, under normal conditions, in turn depends directly upon the length of the ROS (Reiser et al., 1996). S is a sensitivity (R*$^{-1}$ s$^{-2}$) parameter that, if stimulus intensity is correctly specified, is related to the amplification constant, A, which summarizes the kinetics of the series of processes initiated by the photoisomerization of rhodopsin and resulting in closure of the channels in the plasma membrane of the photoreceptor. t$_d$ is a brief delay (s). Fitting of the model is restricted to the leading edge of the a-wave.

Deactivation of Phototransduction

In the same rats, using a double-flash paradigm, the time-course of the rod response to a 'green' (λmax 530 nm) conditioning flash (CF) producing approximately 150 R* is derived. This green flash, while eliciting an a-wave of less than half of the saturated rod response, is nevertheless sufficient to fully suppress the dark current. First, the response to the CF is recorded alone. Then, the amplitude of the response to an intense, rod-saturating (approximately 10,000 R*) 'white' xenon-arc probe flash is determined. The amplitude of the PF response, a$_{max}$ (μV), which is measured at 8 ms after presentation (just before the trough of the a-wave), is taken as proportional to the maximal rod dark current. Next, the CF and PF are presented together, separated by 10 predetermined inter-stimulus intervals (10 ms, 20 ms, 50 ms, 0.1 s, 0.15 s, 0.2 s, 0.4 s, 0.7 s, 1 s, and 1.4 s). In double-flash conditions, the response to the CF recorded alone served as the baseline for measuring the amplitude of the response to the PF at each inter-stimulus time t, a$_{sat,t}$. The proportion of the dark current suppressed by the CF at elapsed time t, SF$_t$, is, therefore, given by $$SF_t = 1 - \frac{a_{sat,t}}{a_{max}}, \quad (5)$$

To derive a value for the time-course of deactivation, the trough of the rod response is determined and a line is fit through the recovery phase. The latency to 50% recovery, (ms), is noted.

Post-Receptor Function

Rod-mediated, post-receptor function is evaluated, in the same animals, from the ERG b-wave. A series of 13 'green' flashes producing from approximately 0.075 to 300 R* is used to elicit b-wave responses. To the amplitudes (μV) of such responses, the parameters of the Naka-Rushton function, $$\frac{V(i)}{Vm} = \frac{i}{i + \sigma}, \quad (6)$$

are optimized. In this equation, V(i) is the amplitude of the response to a flash of i intensity (R*), Vm is the saturated amplitude of the b-wave, and a is the intensity that evokes a b-wave with amplitude of half Vm. The function is fit only up to those intensities at which a-wave intrusion is first observed. If i is correctly specified, log a is a measure of post-receptor sensitivity.

Recovery from a Bleach

In the second set of experiments, performed on cohorts, the recovery of the dark current from the bleach is assessed. The rod-saturating PF (10,000 R*), presented to the dark-adapted eye, is used to determine the magnitude of the dark current. Following the bleaching exposure, the response to the PF is monitored at 2 min intervals for approximately 40 min. At each time, the fraction of the dark current recovered (1−SFt) is calculated. The time to 50% recovery of the saturating rod photoresponse, $t_{50}$, is found by optimizing the parameters of the function $$t(P) = -t_0 \cdot \ln\left(\frac{P - P_0}{B}\right) \quad (7)$$

and then solving the equation for P=50%. In this equation, t(P) is the time required for the a-wave to reach P percent of its dark-adapted value, $t_0$ is the time constant of regeneration, $P_0$ is the normalized amplitude of the dark-adapted a-wave (100%), and B is a scalar. Often, $t_{50}$ is longer than the recording session and is therefore extrapolated.

Stimulus Delivery

The timing and intensity of the ERG stimuli are under computer control. The inter-stimulus interval and number of sweeps averaged for the intensity series used to assess receptor and post-receptor response sensitivities and amplitudes are detailed below. For deactivation experiments, the response to the conditioning flash is averaged eight times, the response to the probe flash is averaged four times and, in double-flash conditions, all traces are averages of two sweeps, recorded 1 min apart. In the bleaching experiment, the probe flash is delivered singly every 2 min.

ERG Intensity Series.

| Light source | Intensity[a] (R*) | Sweeps (minimum) | I.S.I. (s) |
|---|---|---|---|
| 'Green' LED | 0.075 | 32 | 0.35 |
|  | 0.15 | 24 | 0.40 |
|  | 0.30 | 24 | 0.45 |
|  | 0.60 | 18 | 0.50 |
|  | 1.0 | 18 | 0.60 |
|  | 2.5 | 14 | 0.75 |
|  | 5.0 | 14 | 1.0 |
|  | 9.5 | 11 | 1.5 |
|  | 20 | 11 | 2.0 |
|  | 40 | 8 | 2.5 |
|  | 75 | 8 | 4.0 |
|  | 150 | 6 | 5.5 |
|  | 300 | 6 | 8.0 |
| Xenon-arc | 1000 | 5 | 18 |
|  | 2500 | 4 | 27 |
|  | 5000 | 4 | 40 |
|  | 10,000 | 3 | 60 |
|  | 20,000 | 3 | 90 |

[a] The efficiency (R* cd$^{-1}$ s$^{-1}$ m$^2$) of the 'green' LED and xenon-arc flashes are respectively calculated at ~150 and ~75.

Analysis of Retinal Vessels

Vascular tortuosity is evaluated in both eyes of subjects using a noninvasive technique, a necessity in this longitudinal study. The OIR model employed in this study is characterized by a 100% incidence of NV; it is also characterized by tortuous retinal vessels. In patients, the posterior pole is the region most important to the diagnosis of high-risk ROP.

Correspondingly, following each ERG session, wide-field images of the ocular fundus showing the major vessels of the retina are obtained and composited to display a complete view of the posterior pole, defined here as the region within the circle bounded by the vortex veins and concentric to the optic nerve head; the vortex veins define the equator. The arterioles are identified and their tortuosity measured using RISA software, as previously described (Akula et al., 2007; Akula et al., 2008; Gelman et al., 2005; Hansen et al., 2008; Martinez-Perez et al., 2002, 2007). Briefly, each vessel is cropped from the main image and segmented individually. If necessary, the segmented image is manually edited to remove extraneous features such as the background choroidal vasculature. RISA constructed a skeleton and marked terminal and bifurcation points. The user then selected the vessel segments for analysis and RISA automatically calculated the integrated curvature, IC, for the selected segments of each vessel. IC captures any departure from linear course and is the sum of angles along the vessel, normalized by the vessel length (radians pixel$^{-1}$). Thus, a theoretical straight vessel has IC=0. High values of IC capture well vessels that a clinician would be likely to designate as tortuous. Arteriolar tortuosity, TA (radians pixel$^{-1}$), is calculated for each subject as the mean integrated curvature of all measurable arterioles in both eyes (median 10).

Example 13: Human Clinical Trial for Retinopathy of Prematurity

Purpose:

The main purpose of this study is to evaluate the safety of a clinical trial candidate when orally administered to newborns with ROP. Further objective of this study is to evaluate the efficacy of the clinical trial candidate to reduce the progression of ROP through serial ophthalmologic examinations planned at different intervals according to the severity of ROP, in comparison with what is observed in a control group receiving conventional treatment (treatment adopted by the ETROP Cooperative Group).

Methods:

An interventional pilot randomized controlled trial is conducted to evaluate the safety and efficacy of the clinical trial candidate when used in addition to the conventional approach (treatment adopted by the ETROP Cooperative Group) versus the conventional approach alone to treat preterm newborns (gestational age less than 32 weeks) with a stage 2 ROP (zone II-III without plus). Patients are excluded if any of the following exclusion criteria is met at enrollment in the study: (1) more than 10 episodes of bradycardia of prematurity/day (HR<90 bpm); (2) atrioventricular (A-V) block (2nd or 3rd degree); (3) significant congenital heart anomaly (not including patent ductus arteriosus, patent foramen ovale or small ventricular septal defect); (4) heart failure; (5) hypotension (mean blood pressure<45 mmHg); (6) hypoglycemia (<50 mg/dL); and (7) platelet count<100000/mm$^3$.

In order to compare the proportions of newborns that progresses to more-severe ROP in treated group and control group, the estimated sample size was calculated, considering normal distribution, an alpha error of 0.05 and a power of 80 percent. The sample size for each group is 22 participants. The incidence of progression from stage 2 ROP to higher stages increases with the decreasing of the gestational age. To ensure a homogeneous distribution of the gestational age in both groups (treated and controls), the recruited newborns will be randomized and stratified according to their gestational age in three different groups: group 1 (23-25 weeks), group 2 (26-28 weeks), and group 3 (29-32 weeks).

At the beginning of the study, patients in each gestational group are further divided into two groups, one receiving the clinical development candidate orally in suspension form at the dose of 0.5 mg/kg/6 hours, and the other receiving placebo in suspension form. In both treated and placebo groups, the convention treatment adopted by the ETROP Cooperative Group continues. Both the treated and placebo groups are subject to ophthalmological examinations at 40 weeks of gestational age. The ophthalmologists are blindfolded as to which patients receive the clinical development candidate and which patients receive placebo.

Assessment:

to evaluate the safety of the clinical development candidate, cardiac and respiratory parameters (heart frequency, blood pressure, oxygen saturation, respiratory support), are continuously monitored. Blood samplings are performed as soon as the stage 2 ROP will be diagnosed, to check renal, liver and metabolic balance. Kruskal-Wallis test is used to assess possible differences between newborns receiving the clinical development candidate and newborns receiving placebo. The safety is also evaluated by means of relative risk (RR). RR is calculated as the ratio between the probability of side effects in the treated group with respect to the control group. RR is also calculated as the ratio between the probability that ROP progresses to more-severe ROP in treated group with respect to the control group. In this case, values of RR lower than 1 are associated to the efficacy of the treatment. If necessary, RR for each gestational age group is obtained.

For efficacy, all newborns (treated and control groups) are evaluated at 40 weeks of gestational age by using a recently published battery of behavioral tests designed to assess various aspects of visual function (Ricci et al, *Early Hum Dev.* 2008 February; 84(2):107-13), which includes items that assess ocular movements (spontaneous behavior and in response to a target), the ability to fix and follow a black/white target (horizontally, vertically, and in an arc), the reaction to a colored target, the ability to discriminate between black and white stripes of increasing spatial frequency, and the ability to keep attention on a target that is moved slowly away from the infant. Visual function is evaluated again at 1, 4½, 12, 18 and 24 months corrected age (Ricci et al. *J Pediatr.* 2010 April; 156(4):550-5) with particular regards to visual acuity (binocular and monocular), measured by means of well known instruments based on preferential force choice (Teller acuity cards), stereopsis and ocular motricity.

Example 14: Human Clinical Trial for Choroidal Neovascularization

Purpose:

The main objective of this study is to evaluate the safety of a clinical development candidate when orally administered to patients with choroidal neovascularization (CNV) secondary to age-related macular degeneration (AMD). Further objective of this study is to evaluate the efficacy of the clinical development candidate for the treatment of choroidal neovascularization (CNV) secondary to age-related macular degeneration (AMD), in comparison with what is observed in a control group receiving placebo treatment.

Methods:

An interventional pilot randomized controlled trial is conducted to compare the safety and efficacy of the clinical development candidate versus placebo for patients with choroidal neovascularization (CNV) secondary to age-related macular degeneration (AMD). Patients are eligible if (1) they are male or female of 50 years of age or greater; (2) they are diagnosed with primary or recurrent subfoveal CNV secondary to AMD, including those with predominantly classic, minimally classic or active occult lesions with no classic component; (3) they have a BCVA score between 73 and 24 letters (approximately 20/40 to 20/320 Snellen equivalent), inclusively, in the study eye; (4) total area of CNV (including both classic and occult components) encompassed within the lesion is at least 50% of the total lesion area; and (5) total lesion area is no more than 12 disc areas.

Patients are ineligible if one of the following conditions are met: (1) patients who have in the fellow eye a Snellen equivalent below 20/200; (2) presence of angioid streaks, presumed ocular histoplasmosis syndrome, myopia (exceeding −8 diopters), or CNV secondary to causes other than AMD in the study eye; (3) subfoveal fibrosis or atrophy in the study eye; (4) vitreous hemorrhage, retinal tear or history of rhegmatogenous retinal detachment or macular hole (Stage 3 or 4) in the study eye; (5) active, or history of, ocular inflammation or infection in the study eye within the last 30 days prior to screening; (6) uncontrolled glaucoma in the study eye; (7) treatment in the study eye with verteporfin, external-beam radiation therapy, subfoveal focal laser photocoagulation, vitrectomy, submacular surgery, or transpupillary thermotherapy within 30 days prior to screening; (8) previous treatment with anti-angiogenic drugs (pegaptanib, ranibizumab, bevacizumab, anecortave acetate, corticosteroids, protein kinase C inhibitors, squalamine, siRNA, VEGF-Trap etc.) for neovascular AMD in the study eye; (9) history of intraocular surgery in the study eye including pars plana vitrectomy, except for uncomplicated cataract surgery more than 60 days prior to screening; History of YAG laser posterior capsulotomy in the study eye within 30 days prior to screening.

At the beginning of the study, patients are divided into six groups. The clinical development candidate is administered orally in tablet form at the dose of 2, 5, 7, 10, and 20 mg/day, respectively, to the first five groups of patients for 3 months. Placebo is administered orally in tablet form to the sixth group of patients during the same time period. Both the treated and placebo groups will be subject to ophthalmological examinations at the end of each month. The ophthalmologists are blindfolded as to which patients receive the clinical development candidate and which patients receive placebo.

Assessment:

To evaluate the safety of the clinical development candidate, cardiac and respiratory parameters (heart frequency, blood pressure, oxygen saturation, respiratory support) are monitored after oral administration of the clinical development candidate. Blood samplings are also performed to check renal, liver and metabolic balance. The safety of the clinical development candidate is further evaluated by means of relative risk (RR). RR will be calculated as the ratio between the probability of side effects in the treated group with respect to the control group. RR is also calculated as the ratio between the probability that DR progresses to more-severe DR in treated group with respect to the control group. In this case, values of RR lower than 1 will be associated to the efficacy of the treatment.

To evaluate the efficacy of the clinical development candidate, outcome measures include the incidence of ocular and nonocular adverse events, the percentage of patients gaining ≥15 letters of visual acuity (VA) at 3 months from baseline, the percentage of patients losing ≥15 letters of VA at 3 months from baseline, and mean change in VA and central retinal thickness (CRT) at 3 months from baseline.

Example 15: Human Clinical Trial for Retinal Neovascularization Associated with Uveitis Purpose:

The main objective of this study is to evaluate the safety of a clinical development candidate when orally administered to patients with retinal neovascularization (RNV) associated with uveitis. Further objective of this study is to evaluate the efficacy of the clinical development candidate for the treatment of with retinal neovascularization (RNV) associated with uveitis, in comparison with what is observed in a control group receiving placebo treatment.

Methods:

An interventional pilot randomized controlled trial is conducted to compare the safety and efficacy of the clinical development candidate versus placebo for patients with retinal neovascularization (RNV) associated with uveitis. Patients are eligible if (1) they are male and female patients with non-infectious intermediate or posterior uveitis or panuveitis in at least one eye, age 18 to 70 years of age inclusive, who are otherwise in good health; (2) macular edema with average central retinal thickness ≥250 µm; (3) a vitreous haze score ≥1, but ≤3 (based on the National Eye Institute grading system); (4) Best Corrected Visual Acuity no worse than 20/400 and no better than 20/40; and (5) Daily prednisone dose <1 mg/kg.

Patients are not eligible if one of the following conditions is met: (1) patients with choroidal neovascularization; (2) patients with Serpiginous choroidopathy, Acute multifocal placoid pigment epitheliopathy, or White dot retino-choroidopathies (e.g., multiple evanescent white dot syndrome (MEWDS) or multifocal choroiditis); (3) macular edema associated with other ocular disease (e.g., diabetic retinopathy); (4) patients who had a prior vitrectomy; (5) any eye condition that may affect the evaluation of visual acuity and retinal thickness; (6) concurrent use of certain immunosuppressive agents (specific washout periods for different agents are defined in the protocol); (7) use of systemic medications known to be toxic to the lens, retina, or optic nerve (e.g. deferoxamine, chloroquine, and ethambutol) currently or in the past 6 months; and (8) other protocol-defined inclusion/exclusion criteria may apply.

At the beginning of the study, patients are divided into six groups. The clinical development candidate is administered orally in tablet form at the dose of 2, 5, 7, 10, and 20 mg/day, respectively, to the first five groups of patients for 3 months. Placebo is administered orally in tablet form to the sixth group of patients during the same time period. Both the treated and placebo groups will be subject to ophthalmological examinations at the end of each month. The ophthalmologists are blindfolded as to which patients receive the clinical development candidate and which patients receive placebo.

Assessment:

To evaluate the safety of the clinical development candidate, cardiac and respiratory parameters (heart frequency, blood pressure, oxygen saturation, respiratory support) are monitored after oral administration of the clinical development candidate. Blood samplings are also performed to check renal, liver and metabolic balance. The safety of the clinical development candidate is further evaluated by means of relative risk (RR). RR will be calculated as the ratio between the probability of side effects in the treated group with respect to the control group. RR is also calculated as the ratio between the probability that DR progresses to more-severe DR in treated group with respect to the control group. In this case, values of RR lower than 1 will be associated to the efficacy of the treatment.

To evaluate the efficacy of the clinical development candidate, Best-corrected visual acuity (BCVA) and central retinal thickness (CRT) are assessed by certified examiners at scheduled monthly ophthalmological examinations. Outcome measures include the incidence of ocular and nonocular adverse events, the percentage of patients gaining ≥15 letters of visual acuity (VA) at 3 months from baseline, the percentage of patients losing ≥15 letters of VA at 3 months from baseline, and mean change in VA and central retinal thickness (CRT) at 3 months from baseline.

While certain embodiments of the present invention have been shown and described herein, it will be obvious to those skilled in the art that such embodiments are provided by way of example only. Numerous variations, changes, and substitutions may occur without departing from the scope of the embodiments. It should be understood that various alternatives to the embodiments described herein may be employed. It is intended that the following claims define the scope of the invention and that methods and structures within the scope of these claims and their equivalents be covered thereby.

What is claimed is:

1. A method for treating proliferative diabetic retinopathy in a patient having been previously diagnosed with proliferative diabetic retinopathy comprising administering to the patient a therapeutically effective amount of a composition comprising a compound, or stereoisomer, N-oxide or a pharmaceutically acceptable salt thereof, having the structure:

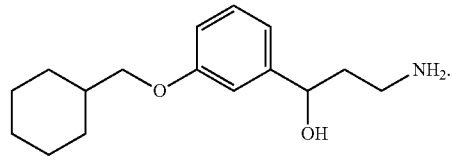 [SMILES: NCCC(O)c1cccc(OCC2CCCCC2)c1]

2. The method of claim 1, wherein the composition is administered to the patient orally.

3. The method of claim 1, wherein the composition is administered once per day, and the composition is administered in the evening or prior to going to sleep.

4. The method of claim 1, wherein treatment results in improvement of central vision in the patient.

5. The method of claim 1, 2, 3, or 4, wherein the (R)-3-amino-1-(3-(cyclohexylmethoxy)phenyl)propan-1-ol is administered as a daily dose of about 2 mg; about 5 mg; about 7 mg; or about 10 mg.

* * * * *